(12) United States Patent
Baker, Jr. et al.

(10) Patent No.: US 9,017,644 B2
(45) Date of Patent: Apr. 28, 2015

(54) METHODS OF TREATING AUTOIMMUNE DISORDERS AND/OR INFLAMMATORY DISORDERS

(75) Inventors: James R. Baker, Jr., Ann Arbor, MI (US); Larry A. Sternson, Berwyn, PA (US); David Repp, Ann Arbor, MI (US); Deborah Ladenheim, Dexter, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 982 days.

(21) Appl. No.: 13/126,633

(22) PCT Filed: Nov. 9, 2009

(86) PCT No.: PCT/US2009/063738
§ 371 (c)(1),
(2), (4) Date: Jul. 22, 2011

(87) PCT Pub. No.: WO2010/054321
PCT Pub. Date: May 14, 2010

(65) Prior Publication Data
US 2011/0268731 A1    Nov. 3, 2011

Related U.S. Application Data

(60) Provisional application No. 61/112,387, filed on Nov. 7, 2008.

(51) Int. Cl.
| A61K 47/48 | (2006.01) |
| A61K 49/12 | (2006.01) |
| A61K 49/00 | (2006.01) |
| A61K 49/08 | (2006.01) |

(52) U.S. Cl.
CPC ....... A61K 49/0043 (2013.01); A61K 47/48107 (2013.01); A61K 47/48169 (2013.01); A61K 49/085 (2013.01); A61K 49/124 (2013.01)

(58) Field of Classification Search
None
See application file for complete search history.

(56) References Cited

U.S. PATENT DOCUMENTS

| 4,161,948 A | 7/1979 | Bichon |
| 4,507,466 A | 3/1985 | Tomalia et al. |
| 4,558,120 A | 12/1985 | Tomalia et al. |
| 4,568,737 A | 2/1986 | Tomalia et al. |
| 4,587,329 A | 5/1986 | Tomalia et al. |
| 4,631,337 A | 12/1986 | Tomalia et al. |
| 4,694,064 A | 9/1987 | Tomalia et al. |
| 4,708,930 A | 11/1987 | Kortright et al. |
| 4,713,975 A | 12/1987 | Tomalia et al. |
| 4,737,550 A | 4/1988 | Tomalia et al. |
| 4,743,543 A | 5/1988 | Kortright |
| 4,827,945 A | 5/1989 | Groman |
| 4,857,599 A | 8/1989 | Tomalia et al. |
| 4,871,779 A | 10/1989 | Killat et al. |
| 4,892,935 A | 1/1990 | Yoshida et al. |
| 4,914,021 A | 4/1990 | Toth |
| 4,918,164 A | 4/1990 | Hellstrom et al. |
| 4,921,789 A | 5/1990 | Salem et al. |
| 4,921,790 A | 5/1990 | OBrien |
| 4,939,240 A | 7/1990 | Chu et al. |
| 4,946,778 A | 8/1990 | Ladner et al. |
| 4,963,484 A | 10/1990 | Kufe |
| 4,965,128 A | 10/1990 | Greidanus |
| 5,041,516 A | 8/1991 | Frechet et al. |
| 5,053,489 A | 10/1991 | Kufe |
| 5,110,911 A | 5/1992 | Samuel et al. |
| 5,270,163 A | 12/1993 | Gold et al. |
| 5,338,532 A | 8/1994 | Tomalia et al. |
| 5,354,308 A | 10/1994 | Simon et al. |
| 5,387,617 A | 2/1995 | Hedstrand et al. |
| 5,393,795 A | 2/1995 | Hedstrand et al. |
| 5,393,797 A | 2/1995 | Hedstrand et al. |
| 5,475,096 A | 12/1995 | Gold et al. |
| 5,512,443 A | 4/1996 | Schlom et al. |
| 5,527,524 A | 6/1996 | Tomalia et al. |
| 5,545,530 A | 8/1996 | Satomura et al. |
| 5,560,929 A | 10/1996 | Hedstrand et al. |
| 5,631,329 A | 5/1997 | Yin et al. |
| 5,661,025 A | 8/1997 | Szoka et al. |
| 5,674,192 A | 10/1997 | Sahatjian |
| 5,693,014 A | 12/1997 | Abele et al. |
| 5,693,763 A | 12/1997 | Codington et al. |
| 5,714,166 A | 2/1998 | Tomalia et al. |
| 5,733,303 A | 3/1998 | Israel |
| 5,755,722 A | 5/1998 | Barry |

(Continued)

FOREIGN PATENT DOCUMENTS

| CA | 2187921 | 11/1995 |
| CA | 2386998 | 4/2001 |

(Continued)

OTHER PUBLICATIONS

Thomas et al (Journal of Medicinal Chemistry, 2005, vol. 48, pp. 3729-3735).*
Chandrasekar et al (Biomaterials, 2007, vol. 28, pp. 504-512).*
Maini et al (Lancet, 1999, vol. 354, pp. 1932-1939).*
Huang, B., et al., "Copper-free click conjugation of methotrexate to a PAMAM dendrimer platform", Tetrahedron Letters, E-pub, Dec. 10, 2010, v. 52, pp. 1411-1414.
Dijk, M.V., et al., "Synthesis and Applications of Biomedical and Pharmaceutical Polymers via Click Chemistry Methodologies," Bioconjugate Chemistry, Nov. 2009, v. 20, No. 11, pp. 2011-2016.
Nimmo, C.M. et al., "Regenerative Biomaterials that 'Click': Simple, Aqueous-Based Protocols for Hydrogel Synthesis, Surface Immoboilization, and 3D Patterning" Bioconjugate Chemistry, Oct. 13, 2011, v. 22, pp. 2199-2209.

(Continued)

*Primary Examiner* — Karen Canella
(74) *Attorney, Agent, or Firm* — Casimir Jones S.C.

(57) ABSTRACT

The present invention relates to dendrimer compositions configured for treating inflammatory disorders and autoimmune disorders, and related methods of synthesis. Specifically, the present invention relates to methods for treating rheumatoid arthritis with PAMAM dendrimers having functional ligands configured for treating rheumatoid arthritis (e.g., therapeutic agents, pro-drugs, targeting agents, trigger agents, imaging agents) (e.g., methotrexate).

2 Claims, 30 Drawing Sheets

(56) References Cited

U.S. PATENT DOCUMENTS

| | | | |
|---|---|---|---|
| 5,773,527 | A | 6/1998 | Tomalia et al. |
| 5,792,105 | A | 8/1998 | Lin |
| 5,795,582 | A | 8/1998 | Wright |
| 5,800,391 | A | 9/1998 | Kontos |
| 5,800,508 | A | 9/1998 | Goicoechea et al. |
| 5,800,519 | A | 9/1998 | Sandock |
| 5,808,005 | A | 9/1998 | Codington et al. |
| 5,843,089 | A | 12/1998 | Sahatjian |
| 5,851,228 | A | 12/1998 | Pineheiro |
| 5,855,866 | A | 1/1999 | Thorpe |
| 5,855,881 | A | 1/1999 | Loike et al. |
| 5,857,998 | A | 1/1999 | Barry |
| 5,861,319 | A | 1/1999 | Lin |
| 5,866,561 | A | 2/1999 | Ungs |
| 5,868,719 | A | 2/1999 | Tsukernik |
| 5,876,445 | A | 3/1999 | Andersen |
| 5,892,019 | A | 4/1999 | Schlom |
| 5,892,020 | A | 4/1999 | Mezes |
| 5,898,005 | A | 4/1999 | Singh |
| 5,902,863 | A | 5/1999 | Dvornic et al. |
| 5,908,413 | A | 6/1999 | Lange |
| 5,913,894 | A | 6/1999 | Schmitt |
| 5,922,887 | A | 7/1999 | Dondio et al. |
| 5,933,145 | A | 8/1999 | Meek |
| 5,935,114 | A | 8/1999 | Jang |
| 6,051,429 | A | 4/2000 | Hawley-Nelson et al. |
| 6,054,444 | A | 4/2000 | Jackson |
| 6,267,987 | B1 | 7/2001 | Park et al. |
| 6,312,679 | B1 | 11/2001 | Tomalia et al. |
| 6,471,968 | B1 | 10/2002 | Baker et al. |
| 6,485,718 | B1 | 11/2002 | Parthasarathy |
| 6,585,956 | B2 | 7/2003 | Malik et al. |
| 6,869,772 | B2 | 3/2005 | Lichtman et al. |
| 7,078,461 | B2 | 7/2006 | Tomalia |
| 7,097,856 | B2 | 8/2006 | Frechet |
| 7,208,486 | B2 | 4/2007 | Burnett |
| 7,261,875 | B2 | 8/2007 | Li |
| 7,368,512 | B2 | 5/2008 | Newkome |
| 7,419,686 | B2 | 9/2008 | Kaiko et al. |
| 7,459,145 | B2 | 12/2008 | Bao |
| 7,572,459 | B2 | 8/2009 | Matthews |
| 7,745,229 | B2 | 6/2010 | Wang |
| 2001/0031498 | A1 | 10/2001 | Leclercq |
| 2002/0165179 | A1 | 11/2002 | Baker, Jr. |
| 2003/0180250 | A1 | 9/2003 | Chauhan et al. |
| 2004/0109842 | A1 | 6/2004 | Baker, Jr. |
| 2004/0120979 | A1 | 6/2004 | Roessler et al. |
| 2005/0214247 | A1 | 9/2005 | Shaunak |
| 2006/0057211 | A1 | 3/2006 | Chorny |
| 2007/0020620 | A1 | 1/2007 | Finn |
| 2007/0041934 | A1 | 2/2007 | William |
| 2007/0298006 | A1 | 12/2007 | Tomalia et al. |
| 2008/0045689 | A1 | 2/2008 | Stumbe et al. |
| 2008/0171067 | A1 | 7/2008 | Govindan et al. |
| 2008/0200562 | A1 | 8/2008 | Yin |
| 2008/0312344 | A1 | 12/2008 | Liskamp |
| 2009/0012035 | A1 | 1/2009 | Jacobson et al. |
| 2009/0053139 | A1 | 2/2009 | Shi |
| 2009/0069561 | A1 | 3/2009 | Fokin et al. |
| 2009/0082537 | A1 | 3/2009 | Hernandez et al. |
| 2009/0088376 | A1 | 4/2009 | Baker, Jr. |
| 2009/0104119 | A1 | 4/2009 | Majoros et al. |
| 2009/0208580 | A1 | 8/2009 | Shi |
| 2009/0287005 | A1 | 11/2009 | Baker, Jr. |
| 2010/0136614 | A1 | 6/2010 | Luo et al. |
| 2010/0158850 | A1 | 6/2010 | Baker, Jr. |
| 2010/0160299 | A1* | 6/2010 | Baker et al. .......... 514/221 |
| 2010/0183749 | A1 | 7/2010 | Brey |

FOREIGN PATENT DOCUMENTS

| | | |
|---|---|---|
| CN | 101267803 | 9/2008 |
| EP | 0099758 | 10/1984 |
| EP | 0271180 | 6/1988 |
| EP | 1941861 | 7/2008 |
| JP | 2002-265495 | 9/2002 |
| WO | 88/01178 | 2/1988 |
| WO | 90/02545 | 3/1990 |
| WO | 95/24221 | 9/1995 |
| WO | 95/28641 | 10/1995 |
| WO | 9707398 | 2/1997 |
| WO | 97/38134 | 10/1997 |
| WO | 98/33941 | 8/1998 |
| WO | 99/02651 | 1/1999 |
| WO | 99/07724 | 2/1999 |
| WO | 9961662 | 2/1999 |
| WO | 99/10362 | 3/1999 |
| WO | 99/58656 | 11/1999 |
| WO | 00/16807 | 3/2000 |
| WO | 01/87348 | 11/2001 |
| WO | 0102861 | 11/2001 |
| WO | 03/003975 | 1/2003 |
| WO | 03/011115 | 2/2003 |
| WO | 03/055935 | 7/2003 |
| WO | 2006/033766 | 3/2006 |
| WO | WO2006/033766 * | 3/2006 |
| WO | 2007/011967 | 1/2007 |
| WO | 2007012001 | 1/2007 |
| WO | 2007/034750 | 3/2007 |
| WO | 2007/080114 | 7/2007 |
| WO | 2008/008483 | 1/2008 |
| WO | 2011/002852 | 1/2011 |
| WO | 2011/028334 | 3/2011 |
| WO | 2011/053618 | 5/2011 |
| WO | 2011/059609 | 5/2011 |
| WO | 2011/072290 | 6/2011 |

OTHER PUBLICATIONS

Huang, B., et al., "The facile synthesis of multifunctional PAMAM dendrimer conjugates through copper-free click chemistry" Bioorganic & Medicinal Chemistry Letters, Mar. 21, 2012, v. 22, pp. 3152-3156.

International Search Report and Written Opinion mailed Mar. 29, 2013, International Patent Application No. PCT/US2012/066104.

Frechet, Jean M.J., et al., "Reversed-phase high-performance liquid chromatographyj of functionalized dendritic macromolecules," Journal of Chromatography A, 667 (1994), pp. 284-289.

Opsteen, et al., "Modular synthesis of block copolymers via cycloaddition of terminal azide and alkyne functionalized polymers", Chemical Communicaitons, vol. 1, pp. 57-59 (2005).

Yim, et al., "Versatile conjugation of octreotide to dendrimers by cycloaddition ("Click") chemistry to yield high-affinity mulivalent cyclic peptide dendrimers," Bioconjugate Chemistry, vol. 20, No. 7, pp. 1323-1331 (2009).

Damen, E.W.P., et al., Biorganic & Medicinal Chemistry (2002) 10(1), pp. 71-77.

Hay, M.P., et al., Journal of Medicinal Chemistry (2003) 46(25), pp. 5533-5545.

Hay, M.P., et al., Journal of the Chemical Society-Perkin Transactions 1 (1999 (19), pp. 2759-2770.

Daniels, T.R., et al., Clinical Immunology (2006) 121(2), pp. 144-176.

Smith, M.W., and M. Gumbleton, Journal of Drug Targeting (2006) 14(4), pp. 191-214.

Koch, 1990, Angew. Chem. Int. Ed. Engl., 29:183-5.

Tomalia, et al., Chem. Int. Ed. Engl. 29:5305 (1990).

Yin, et al., J. Am. Chem. Soc., 120:2678 (1998).

Carelli, V., et al., Bioorganic & Medicinal Chemistry Letters (2003) 13(21), pp. 3765-3769.

Christrup, L.L., et al., International Journal of Pharmaceutics (1997). 154(2): pp. 157-165.

Drustrup, J., et al., International Journal of Pharmaceutics (1991), 71(1-2), pp. 105-116.

Groth, L., et al., International Journal of Pharmaceutics (1997) 154(2), pp. 149-155.

Mignat, C., et al., Journal of Pharmaceutical Sciences (1996) 85(7), pp. 690-694.

Hay, M.P., W.R. Wilson and W.A. Denny, Tetrahedron (2000) 56(4):, pp. 645-657.

(56) References Cited

OTHER PUBLICATIONS de Groot, F.M.H., E.W.P. Damen, and H.W. Scheeren, Curr. Med. Chem.—Anti-Cancer Agents (2001) 8, pp. 1093-1122.
Dubowchik, G.M., and M.A. Walker, Pharmacology & Therapeutics (1999) 83, pp. 67-123.
Papot, S., et al., 2002, "Design of selectively activated anticancer prodrugs: elimination and cyclization strategies.", Curr Med Chem Anticancer Agents.; 2(2):155-85.
De Groot, F.M.H., et al., J. Org. Chem., 2001. 66, pp. 8815-8830.
Greenwald, R.B., et al., J. Med. Chem. (1999). 42: pp. 3657-3667.
Greenwald, R.B., et al., Bioconjugate Chem. (2003) 14, pp. 395-403.
Zhang, Z., et al., Pharmaceutical Research (2005) 22, pp. 381-389.
Antczak, C., et al., Bioorg. & Med. Chem (2001), 9: pp. 2843-2848.
Pohl, T., and H. Waldmann, J. Am. Chem. Soc. (1997), 119, pp. 6702-6710.
Sauerbrei, B., V. Jungmann, and H. Waldmann, Angew. Chem. Int. Ed. (1998), 37: pp. 1143-1146.
Leung, L.Y. and T.A. Baillie, J. Med. Chem. (1986), 29, pp. 2396-2399.
Woolf, T., et al., J. Org. Chem. (1984) 49. pp. 3305-3310.
Nudelman, A., R.J. McCaully and S.C. Bell, J. Pharm. Sci. (1974) 63, pp. 1880-1885.
Esfand, R. and D.A. Tomalila, Drug Discovery Today (2001). 6, pp. 427-436.
Jansen, J.F.G.A., E.M.M. de Brabander van den Berg and E.W. Maijer, Science (1994). 266, pp. 1226-1229.
Kolhe, P., et al., International Journal of Pharmaceutics (2003), 259, pp. 143-160.
Man, N., et al., European Journal of Medicinal Chemistry (2006), 41, pp. 670-674.
Morgan, M.T., et al., J. Am. Chem., Soc. (2003), 125(50): pp. 15485-15489.
Papagiannaros, A., et al., International Journal of Pharmaceutics (2005), 302, pp. 29-38.
Patri, A.K., J.F. Kukowska-Latallo, and J.R. Baker, Advanced Drug Delivery Reviews (2005) 57(15), pp. 2203-2214.
Patri, A.K., I.J Majoros and J.R. Baker Jr., Current Opinion in Chemical Biology (2002) 6, pp. 466-471.
Qiu, L.Y., and Y.H. Bae, Pharmaceutical Research (2006) 23, p. 1-30.
Schcharbin, D. and B.M., Biochmica et Biophysica Acta (2006) 1760, pp. 1021-1026.
Shi, X., et al., Electrophoresis (2006) 27(9), pp. 1758-1767.
Islam, M.T., I.J., Majoros and J.R. Baker, Journal of Chromatography B-Analytical Technologies in the Biomedical and Life Sciences (2005) 822(1-2): p. 21-26).
Islam, MT., et al., Analytical Chemistry (2005) 77(7): p. 2063-2070.
Shi, X., et al., Polymer (2005) 46: p. 3022-3034.
Shi, X., et al. Colloids Surf., A., (2006), 272, pp. 139-150.
Shi, X., I.J Majoros and J.R. Baker, Jr., Mol. Pharm (2005), 2, pp. 278-294.
Shi, X.Y., et al., Electrophoresis (2005) 26(15), pp. 2949-2959.
Shi, X.Y., et al., Analysis (2006) 131(7): p. 842-848.
Shi, X.Y., et al. Analysis (2006) 131(3), pp. 374-381.
Shi, X.Y. et al. Electrophoresis (2005) 26(15): pp. 2960-2967.
Kuracka, L., et al., Clinical Chemistry (1996) 42(5), pp. 756-760.
Orlovic, D., et al., Chromatographia (2000) 52(11/12), pp. 732-734.
Svensson, J., et al., Journal of Chromatography B: Biomedical Sciences and Applications (1982), 230(2), pp. 427-432.
Wangler, C., et al., "Antibody-dendrimer conjugates: the number, not the size of the dendrimers, determines the immunoreactivity," Bioconjug Chem., Apr. 2008, vol. 19(4), pp. 813-820.
Dirks, A. (Ton) J., et al., "Monitoring Protein—Polymer Conugation by a Fluorogenic (Cu(I)-Catalyzed Azide—Alkyne 1,3-Dipolar Cycloaddition," Bioconjugate Chemistry, vol. 20, No. 6, pp. 1129-1138 (Jun. 2009).
Lalwani, Sanjiv, et al., "Mimicking PAMAM Dendrimers with Amphoteric, Hybrid Triazine Dendrimers: A Comparison of Dispersity and Stability," Macromolecules, vol. 42, No. 17, pp. 6723-6732 (Aug. 12, 2009).
Majithia V, et al. Am. J. Med. (2007) 120 (11): 936-9.

Eichman et al. (2000) Pharm. Sci. Technolo. Today 3:232-245.
Lou et al. (2002) Macromol. 35:3456-3462.
Kobayashi et al. (2003) Bioconj. Chem. 14:388-394.
Svensson, J.-O, Journal of Chromatography B., Biomedical Sciences and Applications ()1986) 375, pp. 174-178.
Tebbett, I.R. Chromatographia (187) 23(5), pp. 377-378.
Stamford, J.A., Journal of Neuroscience Methods, (1990), 34(1-3), pp. 67-72.
Toner, C.C., and J.A. Stamford, Journal of Neuroscience Methods (1996) 67(2), pp. 133-140.
Toner, C.D. and J.A. Stamford, Neuroscience (1997), 81(4), pp. 999-1007.
Kimiskidis, V., et al., 2007, "Development and validation of a high performance liquid chromatographic method for the determination of oxcarbazepine and its main metabolites in human plasma and cerebrospinal fluid and its application to pharmacokinetic study", J Pharm Biomed Anal.; 43(2):763-8.
Achilli, G., et al., Journal of Chromatography, A. (1996) 729(1-2), pp. 273-277.
Horner, K.A., et al., Brain Research (2004) 1028(2): pp. 121-132.
Childers, S.R. and S.R. Childers, Life Sciences (1991) 48(21): pp. 1991-2003.
Adams, J.D., Jr., et al. Biomedical Mass Spectometry (1981) 8(11): pp. 527-538.
Millhorn et al, 1996, "Regulation of ionic conductances and gene expression by hypoxia in an oxygen sensitive cell line.", Adv Exp Med Biol. 410:135-42.
Cai, Y.C., et al., "Molecular Pharmacology," (1997) 51(4), pp. 583-587.
Franklin, R,B., et al., BMC Biochemistry (2006) 7: p. 10.
Kukanich, B., et al., Therapeutic Drug Monitoring (2005) 27(3), pp. 389-392.
Cucullo, L., et al., Current Opinion in Drug Discovery & Development (2005) 8(1), pp. 88-99.
Nambiar, M.P., et al., Toxicology and Applied Pharmacology (2007) 219(2-3), pp. 142-150.
Shih, T.M., T.C. Rowland and J.H. McDonough, Journal of Pharmacology and Experimental Therapeutics (2007) 320 (1), pp. 154-161.
Schulte, H., A. Sollevi and M. Segeradahl, Pain, (2005) 116(3), pp. 366-374.
Loetsch, J., et al., Clinical Pharmacology and Therapeutics (1996) 60(3): pp. 316-325.
Hill, H.F., et al., Pain (1990) 43(1), pp. 69-79.
Worek, F., et al., Toxicology (2008). 244: pp. 35-41.
Rheumatoid arthritis, Merck Manual Home Ed. Available at http://wwww.merckmanuals.com/home/print/sec05/ch066/ch066b.html (printed Apr. 19, 2011).
Sottosanti, "Calcium Sulfate: A Biodegradable and Biocompatible Barrier for Guided Tissue Regeneration," Compendium 13(3):226-8, 230, 232-4 (1992).
Springer et al., "Blood Group Tn-Active Macromolecules from Human . . . " Carbohydr. Res. 178:271-292 (1988).
Stoddart, "Gene Delivery with Dendrimers", Chemical Biology 2006.
Talanian et al., "Substrate Specificities of Caspase Family Proteases," J. Biol. Chem., 272:9677 (1997).
Tang et al., "In Vivo Gene Delivery by Degraded Polyamidoamine Dendrimers," Biocong Chem 7:703 (1996).
Tjandra et al., "Application of mammary serum antigen assay in the management of breast cancer: a preliminary report," Br. J. Surg. 75:811-817 (1988).
Tomalia et al., "Starburst Dendrimers: Molecular-Level Control of Size, Shape, Surface chemistry, Topology, and Flexibility from Atoms to Macroscopic Matter," Chem. Int. Ed. Engl., 29:138-175(1990).
Tomalia et al., "Comb-Burst Dendrimer Topology. New Macromolecular Architecture Derived from Dendritic Grating," Macromolecule 24:1435-1438 (1999).
Tomalia, "Starburst/Cascade Dendrimers: Fundamental Building Blocks for a New Nanoscopic Chemistry Set," Advanced Materials 6:529 (1994).

(56) References Cited

OTHER PUBLICATIONS

Tortora et al., "Synergistic Inhibition of Growth and Induction of Apoptosis by 8-Chloro-cAMP and Paclitaxel or Cisplatin in Human Cancer Cells," Cancer Research 57:5107 (1997).
Trainer, et al., "Gene delivery to the epidermis," Human Mol. Gen 6:1761 (1997).
Tuerk et al., "In vitro evolution of functional nucleic acids: high-affinity FNA ligands of HIV-1 proteins," Gene 137 (1):33-9 (1993).
Uppuluri et al., Tecto(Dendrimer) Core-Shell Molecules: . . . PMSE 80:55 (1999).
Urdea and Horn, "Dendrimer Development," Science 261:534 (1993).
Van Hest et al., "Polystyrene-Dendrimer Amphiphilic Block" Copolymers with a Generation-Dependent Aggregation, Science 268:1592-1595 (1995).
Vasey et al., "Phase I Clinicial and Pharmacokinetic Study of PK1 . . . ", Clin. Cancer Res. 5:83 (1999).
Wagner, "Effects of membrane-active agents in gene delivery," Journal of controlled Release 53:155-158 (1998).
Webber et al., "Characterisation of soluble, salt-loaded, degradable PLGA films and their release of tetracycline," J. Biomed Mater Res 41:18 (1998).
White, et al., "Viral Recptors of the Immunoglobulin Superfamily," Cell 56:725 (1989).
Wiener et al., "Dendrimer-Based Metal Chelates: A New Class of Magnetic Resonance Imaging Contrast Agents," Magn Reson. Med. 31:1 (1994).
Wiener et al., "Targeting Dendrimer-Chelates to Tumors and Tumor Cells Expressing the High-Affinity Folate Receptor," Invest. Radiol. 32:748 (1997).
Wies, et al., "Structure of the influenza virus haemagglutinin complexed with its recptor, sialic acid," Nature 333:426 (1988).
Wilbur et al., "Biotin Reagents for Antibody Pretargeting . . . " Bioconjugate Chem., 9:813 (1998).
Winter, "Formation of the Scab and the Rate of Epithelization of Superficial Wounds in the Skin of the Young Domestic Pig," Nature 193:293 (1962).
Wong et al., "Accuracy and Precision of In Vitro Volumetric Measurements by Three-Dimensional Sonography," Ivest. Rad.31:26 (1996).
Wu et al., "Metal-Chelate-Dendrimer-Antibody Constructs for Use in Radioimmunotherapy and Imaging," Bioorg. Med. Chem. Lett., 4:449 (1994).
Wyrick et al., "Entry of Genital *Chlamydia trachomatis* into Polarized Human Epithelial Cells," Infect. Imm. 57:2378 (1989).
Ye, et al., "Targeted gene correction: a new strategy for molecular medicine" Mol. Med. Today 4:431 (1998).
Yew et al., "Optimization of Plasmid Vectors for High-Level Expression in Lung Epithelial Cells," Human Gene Ther. 8:575 (1997).
Yin et al., "Architectural Copolymers: Rod-Shaped, Cylindrical Dendrimers," J. Am. Chem. Soc., 120:2678 (1998).
Yu, et al., "Overexpression of ErbB2 blocks Taxol-Induced Apoptosis by Upregulation of p21(cip1), which Inhibits p34 (Cdc2) Kinase," Molecular Cell, 2:581 (1998).
Zaffaroni et al., "Induction of apoptosis by taxol and cisplatin and effect on cell cycle-related proteins in cisplatin-sensitive and resistance human ovarian cancer cells," Brit. J. Cancer 77:1378 (1998).
Zhuo et al. 1999, In vitro release of 5-fluorouracil with cyclic core dendritic polymer, J. of Controlled Release 57:249-257.
Zimmerman et al., "Self-Assembling Dendrimers," Science 271:1095-1098 (1996).
Suzawa, et al., "Synthesis of a Novel Duocarmycin Derivative DU-257 . . . ", Bioorganic & Medicinal Chemistry 8 (2000) 2175-2184.
Yang, Cancer Research, 1997, vol. 53, pp. 4333-4339.
Wu et al., Anti-Cancer Agents in Medicinal Chemistry, Mar. 2006, vol. 6, pp. 167-184.
International Search Report dated Jan. 5, 2010, PCT/US2009/036992, filed Mar. 12, 2009.

Jesse B. Wolinsky and Mark W. Grinstaff, "Therapeutic and diagnostic application of dendrimers for cancer treatment," Advanced Drug Delivery Reviews, Mar. 4, 2008, vol. 60, pp. 1037-1055.
Ulrik Boas and Peter M. H. Heegaard, "Dendrimers in drug research," Chemical Society Review, 2004, vol. 33, pp. 43-63.
Istvan J. Majoros, et al., "Poly(amidoamine) dendrimer-based multifunctional engineered nanodevice for cancer therapy," Journal of Medicinal Chemistry, 2005, vol. 48, pp. 5892-5899.
Tooru Ooya, Jaehwei Lee and Kinam Park, "Hydrotropic dendrimers of generations 4 and 5: Synthesis, characterization and hydrotropic solubilization of paclitaxel," Bioconjugate Chemistry, 2004, vol. 15, pp. 1221-1229.
Anil K. Patri, et al., "Synthesis and in vitro testing of J591 antibody-dendrimer conjugates for targeted prostage cancer therapy," Bioconjugate Chemistry 2004, vol. 15, pp. 1174-1181.
Thomas, Thommey, et al., "Detection and Analysis of Tumor Fluorescence Using a Two-Photon Optical Fiber Probe," Biophysical Journal, vol. 86, Jun. 2004, pp. 3959-3965.
Kolb, et al. (2001) Angewandte Chemie Intl. Ed. 40:2004-2011.
Evans (2007) Australian J. Chem. 60:384-395.
Carlmark, et al. (2009) Chem. Soc. Rev. 38:352-362.
Allen, T.M., Nature Reviews Cancer (2002) 2, (1), pp. 750-763.
Peer, D., et al., Nature Nanotechnology (2007), 2, pp. 751-760.
Hong, S., et al., Chemistry & Biology (2007), 14 (1), pp. 105-113.
Mammen, M., et al., Angewandte Chemie-International Edition (1998), 37 (20), pp. 2755-2794.
Hong, S.P., et al., Bioconjugate Chmistry (2004) 15, (4), pp. 774-782.
Svenson, S., et al., Advanced Drug Delivery Reviews (2005), 57 (15), pp. 2106-2129.
Hong, S.P., et al., Bioconjugate Chmistry (2006) 17(3), pp. 728-734.
Leroueil, P.R., Acc. Chem. Res. 40(5) (2007) pp. 335-342.
Thomas, T.P., et al., Biomacromoledules (2004) 5, (6) pp. 2269-2274.
Shukla, R., et al., Bioconjugate Chemistry (2006), 17 (5), pp. 1109-1115.
Wu, G., et al., Molecular Cancer Therapeutics (2006) 5(1) pp. 52-59.
Wu, G., et al., Bioconjugate Chemistry (2004) 15(1), pp. 185-194.
Backer, M.V., et al., Molecular Cancer Therapeutics (2005) 4(9), pp. 1423-1429.
Shukla, R., et al., Chemical Communications (2005) 46, pp. 5739-5741.
Sheng, K.C., et al., European Journal of Immunology (2008), 38, pp. 424-436.
Baek, M.G., et al., Bioorganic & Medicinal Chemistry (2002) 10 (1) pp. 11-17.
Taite, L.J, et al., Journal of Biomaterials Science-Polymer Edition (2006) 17(10), pp. 1159-1172.
Kono, K., et al., Bioconjugate Chemistry (1999) 10(6), pp. 1115-1121.
Shukla, S., et al., Bioconjugate Chemistry (2003) 14(1), pp. 158-167.
Thomas, T.P., et al., Journal of Medicinal Chemistry (2005), 48 (11), pp. 3729-3735.
Myc, A., et al., Anti-Cancer Drugs (2008) 19, pp. 143-149.
Majoros, I.J., et al., Journal of Medicinal Chmistry (2005) 48 (19) pp. 5892-5899.
Kukowska-Latallo, J.F., et al., Cancer Research (2005) 65(12) pp. 5317-5324.
Myc, A., et al., Biomacromolecules (2007) 8, pp. 2986-2989.
Myc, A., et al., Biomacromolcules (2007) 8 (1), pp. 13-18.
Landmark, K.J., et al., ACS Nano (2008) 2 (4), pp. 773-783.
Mullen, D.G., Bioconjug. Chem. 19(9) (2008) pp. 1748-1752.
Choi, Y., Nanostructured Supramolecular Arrays Based on Dendrimers Using DNA: Desgin, Synthesis and Biological Evaluation. Biomed. Eng. (NY), vol. Ph.D., Dissertation, University of Michigan, Ann Arbor, MI (2005), p. 191.
Lee, J.W., Macromolecules 39(6) (2006), pp. 2418-2422.
Wu, P., Chem. Commun. (46) (2005), pp. 5775-5777.
Goyal, P., Chem. Eur. J. 13 (2007), pp. 8801-8810.
Yoon, K., Org. Letter 9(11) (2007), pp. 2051-2054.
Choi, Y.S., et al., Nano Letter 4(3) (2004), pp. 391-397.
Demattie, C.R., et al., Nano Letters 4(5) (2004), pp. 771-777.
Choi, Y., et al., Chem. Biol. 12(1) (2005), pp. 35-43.
Rostovtsev, V.V., et al., Angewandte Chemie-Inernational Edition (2002) 41 (14), p. 2596.

(56) References Cited

OTHER PUBLICATIONS

Wu, P., et al., Angewandte Chemie-International Edition (2004) 43 (30) pp. 3928-3932.
Wu, P., et al., Aldrichimica Acta 40(1) (2007), pp. 7-17.
Lee, J.W., et al., Bioconjugate Chemistry (2007) 18(2), pp. 579-584.
Lee, J.W., et al., Journal of Polymer Science Part a-Pollymer Chemistry (2008) 46, pp. 1083-1097.
Lee, J.W., et al., Tetrahedron (2006) 62(5), pp. 894-900.
Hoffman, R.E., Magn. Reson. Chem. (2006), 44, pp. 606-616.
De Groot, Franciscus, M.H., "Cascade-Release Dendrimers", Liberate All End Groups Upon a Single Triggering Event in the Dendritic Core, Angew. Chem. Int. Ed. (2003), vol. 42, pp. 4490-4494.
Lee, Cameron C., et al., "Designing Dendrimers for Biological Applications," Nature Biotechnology, Dec. 2005, vol. 23, No. 12, pp. 1517-1526.
Bloodworth, D., Phys. Med. Rehabil Clin. N. Am., (2006) 17(2), pp. 355-379.
Liu, J.K., et al., Neurobiology of Disease (2005) 1993), pp. 407-418.
Beall, H.D., et al., Journal of Medicinal Chemistry (1998) 41(24), pp. 4755-4766.
Ferrer, S., D.P. Naughton and M.D. Threadgill, Tetrahedron (2003) 59(19), pp. 3445-3454.
Naylor, M.A., et al., Journal of Medicinal Chemistry (1997) 40(15), pp. 2335-2346.
Phillips, R.M., et al., Journal of Medicinal Chemistry (1999) 42(20), pp. 4071-4080.
Zhang, Z., et al., Organic & Biomolecular Chemistry (2005) 3(10), pp. 1905-1910.
Abel et al., "The Selective Concentration of Sulpha-diazine and Related Compounds in Malignant Tissue," Eur. J. Cancer 9:4 (1973).
Abrams, et al., "Programmed cell death during *Drosophila* embryogenesis," Development 117:29 (1993).
Adlish et al., "Identification of a Putative Cell Receptor for Human Cytomegalovirus," Virology 176:337 (1990).
Akutsu et al., "Schedule-dependent Interaction Between Paclitaxel and Doxorubicin in Human Cancer Cell Lines in Vitro," Eur. J. Cancer 31A:2341 (1995).
Australian First Report on Application No. 2005287375 dated Jun. 10, 2008.
Babiuk, Shawn, Foldvari, Marianna, et al., "Cutaneous vaccination: the skin as an immunologically active tissue and the challenge of antigen delivery," Journal of Controlled Release, vol. 66 Issues 2-3, May 15, 2000 pp. 199-214.
Baker et al., "The Synthesis and Testing of Anti-Cancer Therapeutic Nanodevices," Kluwer Academic Publishers, Manufactured in the Netherlands 61-690 (2001).
Baldwin and Saltzman et al., "Materials for protein delivery in tissue engineering" 1998 Advanced Drug Delivery Reviews vol. 33, pp. 71-86.
Balogh and Tomalia, J. Am. Che. Soc. 120:7355 (1998).
Balogh et al., "Formation and Characterization of Dendrimer-Based Water Soluble Inorganic Nanocomposites," Proc. of ACS PMSE 77:118 (1997).
Banga et al., "Assessing the potential of skin electroporation for the delivery of protein- and gene-based drugs," Trends in Biotechnology vol. 16 Issue 10, Oct. 1, 1998 pp. 408-412.
Barker et al., "Utilization of Lipophilic Ionic Additives in Liquid Polymer Film Optodes for Selective Anion Activity Measurements," Anal. Chem. 69:990 (1997).
Barth et al., "Boron Neutron Capture Therapy of Brain Tumors: Past History, Current Status, and Future Potential," Cancer Invetigation 14:534 (1996).
Barth, et al., "Boronated Starburst Dendrimer-Monoclonal Antibody Immunoconjugates: Evaluation as a Potential Delivery System for Neutron Capture therapy," Bioconjugate Chem. 5:58 (1994).
Baumann et al., "Simultaneous Visualization of the Yellow and Green Forms of the Green Fluorescent Protein in Lving Cells," J. Histochem. Cytochem. 46:1073 (1998).
Bell, "Molecular Trees: A New Branch of Chemistry," Science 271:1077-1078 (1996).

Bielinska A. et al., "Regulation of in Vitro Gene Expression Using Antisense Oligonucleotides or . . . " Jun. 1, 1996 Nucleic Acids Research, Oxford University Press, Surrey, GB vol. 24 No. 11.
Bielinska et al. Bioconj Chem 10:843-850 (1999).
Bielinska et al., "Application of membrane-based dendrimer/DNA complexes for solid phase transfection in vitro and in vivo" May 2000 Biomaterials vol. 21, Issue 9, pp. 877-887.
Bielinska et al., "The interaction of plasmid DNA with polyamidoamine dendrimers: . . . " Biochimica et Biophysica Acta 1353:180-190 (1997).
Binkley et al., "RNA ligands to human nerve growth factor," Nuc. Acids Res. 23(16):3198-205 (1995).
Block, Lawrence, "Medicated Applications", Remington's Pharmaceutical Sciences, edited by Gennaro, 1990, 18th Edition, pp. 1596 and 1597.
Botchway, et al., "Novel Visible and Ultraviolet Light Photogeneration of . . . " Photochem., Photobiol. 67(7):635-40 (1998).
Bourassa et al., "Photochemistry of Roussin's Red Salt . . . " JACS 119:2853-60 (1997).
Bourne, et al., "Evaluation of the Effects of Intravascular MR Contrast Media (Gadolinium Dendrimer) on 3D Time of Flight Magnetic Resonance Angiography of the Body," J. Magn. Reson. Imag., 6:305 (1996).
Brandl et al., "Plastics from Bacteria and for Bacteria: . . . ", Adv. Biochem Eng Biotechnol, 41:77 (1990).
Brasseur et al., "Biological Activities of Phthalocyanines . . . " Photochem., Photobiol., 47:705-11 (1988).
Braunegg et al., "Polyhydroxyalkanoates, biopolyesters from renewable resources: Physiological and engineering aspects," J. Biotechnol 65(2-3):127 (1998).
Brazeau et al., "In vitro myotoxicity of selected cationic macromolecules used in non-viral gene delivery," Pharm Research 15:680-684 (1998).
Capale et al., "Boronated Epidermal Growth Factor as a Potential Targeting Agent for Boron Neutron Capture Therapy of Brain Tumors," Bioconjugate Chem., 7:7 (1996).
Carel et al., "Structural Requirements for C3d,g/Epstein-Barr Virus Receptor (CR2/CD21) Ligand Binding, Internalization, and Viral Infection," J. Biol. Chem. 265:12293 (1990).
Chan and Nie, "quantum Dot Bioconjugates for Ultrasensitive Nonisotopic Detection," Science 281:2016 (1998).
Chang, et al., "Synthetic Appropaches to Long-Wavelength Absorbing Photosensitizers: Porphyrinone and Derivatives," Proc. SPIE, 1203:281-86 (1990).
Chinese Office Action dated Jan. 16, 2009, CN Patent Application No. 200580034777.9.
Choate et al., "Direct Cutaneous Gene Delivery in Human Genetic Skin Disease," Human Gene Ther 8:1659 (1997).
Choi et al., "Poly(ethylene glycol)block-poly(L-lysine) Dendrimer: . . . ", Bioconjugate Chem. 10:62-65 (1999).
Cincotta, et al., "Novel Benzophenothiazinium Photosensitizers: Preliminary In-Vivo Results," SPIE Proc. SPIE 1203:202-10 (1990).
Co et al., "Isolation and biochemical characterization of the mammalian reovirus type 3 cell-surface receptor," Proc Natl. Acad. Sci 82:1494 (1985).
Cohen and Tohoku, Exp. Med. 168:351 (1992), Abstract printed on May 1, 2002 (1 page).
Cole et al., "The EBV-Hybridoma Technique and its Application to Human Lung Cancer," in Monoclonal Antibodies and Cancer Therapy, Alan R. Liss, Inc., pp. 77-96 (1985).
Cortese et al., "Identification of biologically active peptides using random libraries displayed on phage," Curr. Opin. Biotechol., 6:73 (1995).
Cote et al., "Generation of human monoclonal antibodies reactive with cellular antigens," Proc. Natl. Acad. Sci. U.S.A. 80:2026-2030 (1983).
Davies, "Synthetic materials for covering burn woulds: Progress towards perfection. Part I. Short term dressing materials," Burns 10:94 (1983).
De Leo and Ford, "Reversible Photolabilzation of NO from Chromium (III)-Coordinated Nitrite. A New Strategy for Nitric Oxide Delivery," JACS 121:1980-81 (1999).
Duncan and Malik, Control Rel. Bioact. Mater. 23:105 (1996).

(56) References Cited

OTHER PUBLICATIONS

Duncan and Sat, "Tumour targeting by enhanced permeability and retention (EPR) effect," Ann. Oncol. 9:39 (1998).
Duncan et al., "Polymer Conjugates for Anti-Cancer Agent and DNA Delivery," Polymer Preprints 39:180 (1998).
Dvornic and Tomalia, "Dendritic polymers divergent synthesis: starburst poly(amidoamine) dendrimers," in Salamone (ed.) The Polymeric Materials Encyclopedia: Synthesis, Proper.
EP Patent Application No. EP 01 935 316.8, Office Action dated Nov. 30, 2007.
Eppstein et al., "Epidermal growth factor receptor occupancy inhibits vaccinia virus infection," Nature 318:663 (1985).
CN Office Action mailed Aug. 14, 2013, CN Patent Application No. 201080059383.
Bhanja, et al., "Protective role of R-spondin1, an intestinal stem cell growth factor, against radiation-induced gastrointestinal syndrome in mice," Plos One, vol. 4, Issue 11, Article No. e8014, pp. 1-10 (Nov. 24, 2009).
Zhao, et al., "R-spondin1 protects mice from chemotheray or radiation-induced oral mucositis through the canonical Wnt/B-catein pathway," PNAS, vol. 106, No. 7, pp. 2331-2336 (Feb. 17, 2009).
Zhou, et al., "Slit-Robo signaling induces malignant transormation through Hakai-mediated E-cadher in degration during colorectal epithelial cell carcinogenesis", Cell Research, vol. 21, No. 4, pp. 609-626 (Feb. 1, 2011).
Wang, eet al., "Induction of tumor angiogenesis by Slit-Robo signaling and inhibition of cancer growth by blocking Robo activity," Cancer Cell, vol. 4, Issue 1, pp. 19-29 (Jul. 2003).
Takashima et al., "The Wnt agonist R-spondin1 regulates systemic graft-versus-host disease by protecting intestinal stem cells," The Journal of Experimental Medicine, vol. 208, No. 2, pp. 285-294 (Jan. 31, 2011).
Zhou, et al., "Induction of intestinal stem cells by R-spondin1 and slit2 augments chemoradioprotection," Nature, vol. 501, No. 7465, pp. 107-111 (Sep. 2013).
Esfand et al., "synthesis, Complexation and Pharmaceutical Applications of Tetra-directional Cascade Dendrimers," Pharm Sci., 2:157 (1996).
Farkas et al., "Microscopic and Mesoscopic Spectral Bio-Imaging," SPEI 2678:200 (1997).
Fidler et al., "The Implications of Angiogenesis for the Biology and Therapy of Cancer Metastatis," Cell, 79:185 (1994).
Firey and Rodgers, "Photo-Properties of a Silicon Naphthalo cyanine: . . . " Photochem. Photobiol., 45:535-38 (1997).
Folkman et al., "Antiogenesis," Journ. of Biol. Chem. 267(16):10931 (1992).
Folkman et al., "Angiogenic Factors," Science, 235:442 (1987).
Folkman, "Clinical Applications of Research on Angiogenesis," New Eng. J. Med. 333(26):1757 (1995).
Fracasso, et al., "Anti-tumor effects of toxins targeted to the prostate specific membrane antigen," The Prostate, 2002, 53: 9-23.
Frechet, et al., "Self-Condensing Vinyl Polymerization: An Approach to Dendritic Materials," Science 269:1080-1083 (1995).
Frechet, "Functional Polymers and Dendrimers: Reactivity, Molecular Architechture, and Interfacial Energy," Science 263:1710-1715 (1994).
Friedman, "Gene Therapy of Cancer Through Restoration of Tumor-Suppressor Functions?J" Cancer 70:1810 (1992).
Fujiwara et al., "Therapeutic Effect of a Retroviral Wild-Type p53 Expression Vector in an Orthotopic Lung Cancer Model," J. Natl. Cancer Inst., 86:458 (1994).
Gac et al., "Synthesis, Characterisation and In Vivo Behaviour of a Norfloxacin-Poly(L-Lysine Citramide Imide) Conjugate Beraing Mannosyl Residues," J. Drug Target 7(5):393 (2000).
Garcia-Contreras et al., "Biodegradable Cisplatin Microspheres for Direct Brain Injection: Preparation and Characterization," Pharm Dev Tech 2:53 (1997).
Gerwitz et al., "Nucleic Acid Therapeutics: State of the Art and Future Prospects," Blood 92:712 (1998).

Gibb, "Apoptosis as a Measure of Chemosensitivity to Cisplatin and Taxol Therapy in Ovarian Cancer Cell Lines," Gynecologoic Oncology 65:13 (1997).
Goodwin and Meares, Cancer (suppl.) 80:2675 (1996).
Haensler et al., "Polyamidoamine Cascade Polymers Mediate Efficient Transfection of Cells in Culture," Bioconjugate Chem. 4:373-379 (1993).
Hanisch et al., "Structural Studies on Oncofetal Carbohydrate . . . " Carbohydr. Res. 178:29-47 (1988).
Hawker et al., "Unimolecular Micelles and Globular Amphiphiles: Dendritic Macromolecules as Novel Recyclable Solubilization Agents," J. Chem. Soc. Perkins Trans. 12:1287-1297 (1993).
Hinoda et al., "Immunochemical Characterization of Adenocarcinoma-Associated Antigen YH206," Cancer J. 42:653-658 (1988).
Hockenbery et al., "Bcl-2 Functions in an Antioxidant Pathway to Prevent Apoptosis," Cell 75:241 (1993).
Holister et al., "Dendrimers" 2003 Technology White Papers pp. 1-15.
Huse, et al., "Generation of a Large Combinatorial Library of the Immunoglobulin Repertoire in Phage Lambda," Science 246:1275-1281 (1989).
International Search Report mailed Sep. 8, 2008, PCT/US2007/15976.
International Search Report dated Jul. 8, 2002, PCT/US01/15204.
International Search Report dated Nov. 20, 2001, PCT/US01/40824.
International Search Report mailed Jul. 17, 2006, PCT/US05/30278.
International Search Report PCT/US2001/15204 mailed Jul. 8, 2002.
International Search Report, PCT/Us2008/061023, dated Dec. 16, 2008.
Ishida et al., "Related Glycoproteins from Normal Secretory and Malignant Breast Cells," Tumor Biol. 10:12-22 (1989).
Jain et al., "Controlled Drug Delivery by Biodegradable Poly(Ester) Devices: Different Preparative Approaches," Drug Dev Ind Pharm 24:703 (1998).
Jane et al., "Vector development: a major obstacle in human gene therapy," Annals of Med 30:413 (1998).
Jansen et al., "The Dendritic Box: Shape-Selective Liberation of Encapsulated Guests," J. Am. Chem. Soc. 117:4417-4418 1995.
Jellinek, et al., "Inhibition of Receptor Binding by High-Affinity RNA Ligands to Vascular Endothelial Growth Factor," Biochem 83(34):10450-6 (1994).
Kaner et al., "Fibroblast Growth Factor Receptor is a Portal of Cellular Entry for Herpes Simplex Virus Type 1," Science 248:1410 (1990).
Kannon and Garrett, "Moist Wound Healing with Occlusive Dressings," Ermatol. Surg. 21:583 (1995).
Kerr et al., "Apoptosis: Its Significance in Cancer and Cancer Therapy," Cancer 73:2013 (1994).
Klatzman et al., "T-lymphocyte T4 molecule behaves as the receptor for human retrovirus LAV," Nature 312:767 (1984).
Kirpotin et al., "Sterically Stabilized Anti-HER2 Immunoliposomes: Design and Targeting to Human Breast Cancer Cells in Vitro," Biochem., 36:66 (1997).
Kjeldsen et al., "Preparation and Characterization of Monoclonal Antibodies Directed to the Tumor-associated O-linked . . . " Cancer Res. 48:2214-2220 (1988).
Kohler and Milstein, "Continuous cultures of fused cells secreting antibody of predefined specificity," Nature 256:495-497 (1975).
Kozbor et al. "the production of monoclonal antibodies from human lymphocytes," Immunol. Today 4:72 (1983).
Krah, "Characterization of Octyl Glucoside-Solubilized Cell Membrane Receptors for Binding Measles Virus," Virology 172:386 (1989).
Kuhlmann et al., "Reduction of cisplatin toxicity in cultured renal tubular cells by the bioflavonoid quercetin," Arch. Toxicol. 72:536 (1998).
Kukowska-Latallo et al., "Efficient transfer of genetic material into mammalian cells using Starburst polyamidoamine dendrimers," Proc. Natl. Acad. Sci. USA 93:4897-4902 (1996).
Lan et al., "Isolation and Properties of a Human Pancreatic Adenocarcinoma-associated . . . " Cancer Res. 45:305-310 (1985).

(56) References Cited

OTHER PUBLICATIONS

Lanni et al., "p53-independent apoptosis induced by paclitaxel througho an indirect mechanism," Proc. Natl. Acad. Sci., 94:9679 (1997).
Lentz, et al., "Is the Acetylcholine Rectpor a Rabies Virus Receptor," Science 215:182 (1982).
Lester et al., "Infrared Microspectroscopic Imaging of the Cerebellum of Normal and Cytarabine Treated Rats," Cell Mol. Biol. 44:29 (1998).
Wang, et al., "Synthesis and Application of Carbohydrate-Containing Polymers", Chem. Mater. (2002) 14, pp. 3232-3244.
Levi-Montalcini, "The Nerve Growth Factor Thirty-Five Years Later," In Vitro Cell., Devl. Biol. 23:227 (1987).
Liao, et al., "Chromophore-assisted laser inactivation of proteins is mediated by the photogeneration of free radicals," PNAS 91:2659 (1994).
Luck et al., "Plasma protein adsorption on biodegradable microspheres . . . " J. Control. Rel 55:107 (1998).
Madihally and Matthew, "Porous chitosan scaffolds for tissue engineering," Biomaterials 20(12):1133 (1999).
Majoros and Tomalia, Mar. 18, 2006 Abstract Only printed Apr. 20, 2009, "Synthesis and Characterization of Novel POPAM-PAMAM (POMAM) Hybrid Dendrimers as Reactive Modules for Nanodevice Construction" Eight Foresight Conference on Molecular Nanotechnology.
Majoros et al., "PAMAM Dendrimer-based multifunctional conjugate for cancer therapy: synthesis, characterization and functionality," Biomacromolecules, 2006, vol. 7, pp. 572-579.
Majoros, et al., "Acetylation of Poly(amidoamine) Dendrimers," Macromolecules 2003, 36, 5526-5529.
Malik et al., "A PAMAM Dendrimer-Platinate," Proc. Int'l Symp. Control. Rel. Bioact. Mater, 24:107 (1997).
Malik et al., "Dendrimers: Relationshipo between structure and biocompatibility in vitro, and preliminary studies on the biodistribution of (125)I-labelled polyamidoamine dendrimers in vivo," Journal of Controlled Relief 65:133-148 (2000).
Marlin et al., "A soluble form of intercellular adhesion molecule-1 inhibits rhinovirus infection," Nature 344:70 (1990).
Mayer et al., "Matrices for tissue engineering-scaffold structure for a bioartificial liver support system," J. Controlled Release 64(1-3):81 (2000).
Mendelsohn et al., "Cellular Receptor for Poliovirus: Molecular Cloning, . . . " Cell 56:855 (1989).
Monsigny et al., "Characterization and biological implications of membrane lectins in tumor, lymphoid and myeloid cells," Biochemie 70:1633 (1988).
Mosmann, "Rapid Colorimetric Assay for Cellular Growth and Survival: Application to Proliferation and Cytotoxity Assays," J. Immunol. Meth, 65:55 (1983).
Murphy, et al., "Photolytic Release of Nitric Oxide Modulates NMDA Receptor-mediated Transmission but Does not Induce Long-term Potentiation at Hippocampal Synapses," Neuropharm. 33:1375-85 (1994).
Naylor et al., Starburst Dendrimers. 5. Molecular Shape Control, J. Am. Chem. Soc. 111:2339-2341 (1989).
Niemiec et al., "Perifollicular Transgenic Expression of Human Interleukin-1 Rectpro Antagonist Protein following Topical Application of Novel Liposome-Plasmid DNA Formulations In Vivo," J. Pharm Sci. 86:701 (1997).
Orentas et al., "Detection of Epstein-Barr virus EBER sequence in post-transplant lymphoma patients with DNA dendrimers," Journal of Virological Methods 77:153-163 (1999).
Ottl, et al., "Preparation and Photoactivation of Caged Fluorophores and Caged Proteins Using a New Class of Heterobifunctional, Photocleavable Cross-Linking Reagents," Bioconjugate Chem. 9:143 (1998).
Page and Roy, "Synthesis and Biological Properties of Mannosylated Starburst Poly(amidoamine) Dendrimers," Bioconjugate Chem., 8:714 (1997).

Pan, et al., "Dendrimer modified magnetite nanoparticles for protein immobilization," Journal of Colloid and Interface Science, 2005, vol. 284, pp. 1-6.
Pandey, et al., "Chlorin and Porphyrine Derivatives as Potential Photosensitizers in Photodynamic Therapy," Photochem., Photobiol., 53:65-72 (1991).
Park et al., "Anti-HER2 immunoliposomes for targeted therapy of human tumors," Cancer Lett., 118:153 (1997).
Pasani et al., "Antitumor Complexes of Platinum with Carrier Molecules," Inorg. Chim. Acta 80:99 (1983).
Pavlova et al., "Biocompatible and biodegradable polyurethane polymers," Biomaterials 14(13):1024 (1993).
Pegrarn et al., Proc. Am. Soc. Clin. Oncol. 14:106 (1995).
Penault-Llorca et al., "Expression of FGF and FGF Receptor Genes in Human Breast Cancer," Int. J. Cancer 61:170 (1995).
Pillai V.N.R., "Photoremovable Protecting Groups in Organic Synthesis," Synthesis: 1-26 (1980).
Pratap Singh, "Terminal Groups in Starburst Dendrimers: Activation and Reaction with Proteins", 1998 Bioconnugate Chem. 9:54-63.
Press et al., "Expression of the HER-2/neu proto-oncogene in normal human adult and fetal tissues," Oncogene 5:953 (1990).
Quintana, et al., "Design and Function of a Dendrimer-Based Therapeutic Nanodevice Targeted to Tumor Cells Through the Folate Receptor," Pharmaceutical Research, vol. 19, No. 9, Sep. 2002.
Raczka et al., "The effect of synthetic surfactant Exosurf on gene transfer in mouse lung in vivo," Gene Ther 5:1333 (1998).
Riley, "Wound Healing," Am Fam. Physician 24:107 (1981).
Rinberg "Pnuematic capillary gun for ballistic delivery of microparticles" 2005 Applied Physics Letters vol. 87 pp. 1-3.
Roberts, et al., "Preliminary biological evaluation of oplyamidoamine (PAMAM) Starburst dendrimers," J. Biomed Mater res 30:53 (1996).
Roessler et al., "Substituted β-Cyclodextrins Interact with PAMAM Dendrimer-DNA Complexes and Modify Transfection Efficiency," Biochem. 124-129 (2001).
Ruff, et al., "CD4 receptor binding peptides that block HIV infectivity cause human monocyte chemotaxis," FEBS Letters 211:17 (1987).
Ruponen et al., "Interactions of polymeric and liposomal gene delivery systems with extracellular glycosaminoglycans: physicochemical and transfection studies," Biochmica ET Biophysica Acta 1415:331-341 (1999).
Sacerdote et al., "Vasoactive Intestinal Peptide 1-12: . . . " J. of Neuroscience Research 18:102 (1987).
Schneider, et al., "Distance-dependent fluorescence quenching on gold nanoparticles ensheathed with layer-by-layer assembled polyelectrolytes," Nano Letters, 2006, vol. 6, pp. 530-536.
Segura and Shea, "Materials for Non-Viral Gene Delivery" 2001 Annual Review of Materials Research, vol. 31 pp. 25-46.
Selman et al., "Copper Benzochlorin, a Novel Photosensitizer for Photodynamic Therapy . . . " Photochem. Photobio, 57:681-85 (1993).
Sessler et al., "Tripyrroledimethine-derived ("texaphyrine"-type) . . . " Proc. SPIE, 1426:318-29 (1991).
Sharon and Lis, "Lectins as Cell Recognition Molecules," Science 246:227 (1989).
Shchepinov et al., "Oligonucleotide dendrimers: synthesis and use as polylabelled DNA probes," Nucleic Acids Research 25:4447-4454 (1997).
Shea, "DNA delivery from polymer matrices for tissue engineering," Jun. 1999, Nature Biotechnology.
Shephey et al., "Monoclonal antibody identificaiton ofa 100-kDa membrane protein in HeLa cells and human spinal cord involved in poliovirus attachment," Proc. Natl. Acad. Sci. 85:7743 (1988).
Shortreed, et al., "Directed Energy Transfer Funnels in Dendrimetric Antenna Supermolecules," J. Phys. Chem. 101-6318 (1997).
Singh et al., "Starburst Dendrimers: Enhanced Performance and Flexibility for Immunoassays," Clin. Chem. 40:1845 (1994).
Sooklal, "A Blue-Emitting CdS/Dendrimer Nanocomposite," Adv. Mater, 10:1083 (1998).
Herrmann, A., et al.: "Peptide-functionalized polyphenylene dendrimers," Tetrahedron, Elsevier Science Publishers, Amsterdam, NL, vol. 59, No. 22, May 26, 2003, pp. 3925-3935.

(56) References Cited

OTHER PUBLICATIONS

EP Extended Search Report mailed Nov. 4, 2014, EP Patent Application No. 10814123.5.

Mullen, Douglas G., "A Quantitative Assessment of Nanoparticle—Ligand Distributions: Implications for Targeted Drug and Imaging Delivery in Dendrimer Conjugates," ACS Nano (2010), 4(2), pp. 657-670.

Mullen, et al., "Design, synthesis, and biological functionality of a dendrimer-based modular drug delivery platform," Bioconjugate Chemistry, vol. 22, No. 4, pp. 679-689 (Mar. 22, 2011).

* cited by examiner

FIGURE 17

|    | #1 | | #2 | | #3 | | #4 | | #5 | | #6 | |
|----|---|---|---|---|---|---|---|---|---|---|---|---|
|    | R | L | R | L | R | L | R | L | R | L | R | L |
| G1 | 0 | 0 | 0 | 0 | 0 | 0 |   |   |   |   |   |   |
| G2 | 3 | 3 | 3 | 3 | 3 | 3 | 4 | 4 | 3 | 3 |   |   |
| G3 | 1 | 1 | 1 | 1 | 1 | 1 | 1 | 1 | 0 | 0 | 0 | 0 |
| G4 | 0 | 0 | 0 | 0 | 1 | 1 | 1 | 1 | 1 | 1 | 0 | 1 |

G1 – negative control, G2 – RA-saline, G3 – MTX 0.25 mg/kg, G4 – MTX 0.75 mg/kg

FIGURE 24

|  | #1 | | #2 | | #3 | |
| --- | --- | --- | --- | --- | --- | --- |
|  | Right | Left | Right | Left | Right | Left |
| RA-saline | 3 | 3 | 3(4) | 3(4) | 3 | 3 |
| RA-G5-MTX | 1 | 1 | 0 | 0 | 1 | 1 |
| RA-G5-FA-MTX (new) | 1 | 1 | 0 | 0 | 1 | 1 |
| RA-G5-FA-MTX (old) | 1 | 1 | 1 | 2 | 1 | 1 |

SEQUENCE LISTING

<160> NUMBER OF SEQ ID NOS: 2

<210> SEQ ID NO 1
<211> LENGTH: 12
<212> TYPE: PRT
<213> ORGANISM: Artificial Sequence
<220> FEATURE:
<223> OTHER INFORMATION: Synthetic

<400> SEQUENCE: 1

His Leu Asn Ile Leu Ser Thr Leu Trp Lys Tyr Arg
1               5                   10

```
<210> SEQ ID NO 2
<211> LENGTH: 7
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: The residue at this position is linked to
      7-methoxycoumarin-4-yl acetyl
<220> FEATURE:
<221> NAME/KEY: MISC_FEATURE
<222> LOCATION: (7)..(7)
<223> OTHER INFORMATION: The residue at this position is linked to a
      2,4-dinitrophenyl group and NH2

<400> SEQUENCE: 2

Tyr Glu Val Asp Gly Trp Lys
1               5
```

METHODS OF TREATING AUTOIMMUNE DISORDERS AND/OR INFLAMMATORY DISORDERS

CROSS REFERENCE TO RELATED APPLICATION

This application is a US 371 national stage entry of pending International Patent Application No. PCT/U.S.2009/063738, International Filing Date, Nov. 9, 2009, which claims priority to U.S. Provisional Patent Application No. 61/112,387, filed on Nov. 7, 2008, the contents of which are hereby incorporated by reference in their entireties.

FIELD OF THE INVENTION

The present invention relates to dendrimer compositions configured for treating inflammatory disorders and autoimmune disorders, and related methods of synthesis. Specifically, the present invention relates to methods for treating rheumatoid arthritis with PAMAM dendrimers having functional ligands configured for treating rheumatoid arthritis (e.g., therapeutic agents, pro-drugs, targeting agents, trigger agents, imaging agents) (e.g., methotrexate).

BACKGROUND OF THE INVENTION

Rheumatoid arthritis (RA) is a chronic, systemic inflammatory disorder that may affect many tissues and organs, but principally attacks the joints producing an inflammatory synovitis that often progresses to destruction of the articular cartilage and ankylosis of the joints. Rheumatoid arthritis can also produce diffuse inflammation in the lungs, pericardium, pleura, and sclera, and also nodular lesions, most common in subcutaneous tissue under the skin. Although the cause of rheumatoid arthritis is unknown, autoimmunity plays a role in its chronicity and progression.

About 1% of the world's population is afflicted by rheumatoid arthritis, women three times more often than men. Onset is most frequent between the ages of 40 and 50, but people of any age can be affected. It can be a disabling and painful condition, which can lead to substantial loss of functioning and mobility. It is diagnosed chiefly on symptoms and signs, but also with blood tests (especially a test called rheumatoid factor) and X-rays. Diagnosis and long-term management are typically performed by a rheumatologist, an expert in the diseases of joints and connective tissues (see, e.g., Majithia V, and Geraci S A (2007) Am. J. Med. 120 (11): 936-9; herein incorporated by reference in its entirety).

Current treatments for rheumatoid arthritis include: non-steroidal anti-inflammatory drugs (NSAIDs), corticosteroids, gold therapy, methotrexate, tumor necrosis Factor Inhibitors such as etanercept (Enbrel®), adalimumab (Humira®), and infliximab (Remicade®), and other immunomodulatory and cytotoxic agents. While these treatments can be effective many require close supervision because of hazardous side effects. Response to treatment with these agents is variable and some patients still experience pain and joint degeneration. Thus, there is a need for additional compounds that can treat rheumatoid arthritis and related diseases.

SUMMARY OF THE INVENTION

Dendrimers are generally spherical, well defined, highly branched macromolecules with dense surface functional groups. There are many types of dendrimers including but not limited to hypercomb branched dendrimers, lysine based dendrimers, cascade molecules, arborols, and poly(amidoamine) dendrimers. Poly(amidoamine) (PAMAM) dendrimers are methodically constructed from an ethylenediamine (EDA) core through repetitive alkylation and amidation steps. The size and number of terminal ends may be controlled by the number of such steps used to synthesize the dendrimer. Dendrimers can be used as a platform to which effector molecules may be linked. Because the number of functional groups on the dendrimers can be controlled on the surface and within the interior, it provides a means for controlling the amount of carried material to be delivered per dendrimer.

Effector molecules may include molecules that, when used in bio-medical applications, direct the compound to a specific target in the body. For example: folic acid has been used to direct the dendrimer to cells which have a comparatively high number of folic acid receptors. Dendrimers have been studied extensively for potential bio-medical applications as delivery devices for drugs, nucleic acids and imaging agents. Procedures for the synthesis of G(5) PAMAM Dendrimers are known in the art (see for example: Dendrimers and other Dendritic Polymers, Edited by Jean M. J. Frechet and Donald A. Tomalia, U.S. Pat. No. 4,587,329).

Rheumatoid arthritis is a chronic disorder for which there is no known cure. Fortunately in the last few years, a shift in strategy toward the earlier institution of disease modifying drugs and the availability of new classes of medications have greatly improved the outcomes that can be expected by most patients. The goal of treatment now aims toward achieving the lowest possible level of arthritis disease activity and remission if possible, the minimization of joint damage, and enhancing physical function and quality of life.

Experiments conducted during the course of developing some embodiments of the present invention determined that PAMAM dendrimers comprising specific functional ligands were effective in the treatment of autoimmune disorders and inflammatory disorders such as, for example, arthritis. In particular, PAMAM dendrimers comprising functional ligands such as methotrexate and folate were shown to be effective in treating autoimmune disorders and inflammatory disorders. Examples of such disorders include, but are not limited to, arthritis (e.g., rheumatoid arthritis, psoriatic arthritis, osteoarthritis), ankylosing spondylitis, psoriasis, lupus erythematosus, Crohn's disease and sarcoidosis.

Accordingly, the present invention relates to dendrimer compositions configured for treating inflammatory disorders and autoimmune disorders such as arthritis, and related methods of synthesis. Specifically, the present invention relates to methods for treating arthritis (e.g., rheumatoid arthritis) with PAMAM dendrimers having functional ligands configured for treating such disorders (e.g., therapeutic agents, pro-drugs, targeting agents, trigger agents, imaging agents) (e.g., methotrexate).

The present invention is not limited to utilizing a particular type or form of dendrimer. Indeed, examples of dendrimers finding use in the present invention include, but are not limited to, a polyamideamine (PAMAM) dendrimer, a Baker-Huang PAMAM dendrimer (see, e.g., U.S. Provisional Patent Application No. 61/251,244, herein incorporated by reference in its entirety), a polypropylamine (POPAM) dendrimer, and a PAMAM-POPAM dendrimer. The type of dendrimer used is not limited by the generation number of the dendrimer. Dendrimer molecules may be generation 0, generation 1, generation 2, generation 3, generation 4, generation 5, generation 6, generation 7, or higher than generation 7. In some embodiments, half-generation dendrimers may be used. In certain embodiments, a generation 5 amine-terminated PAMAM dendrimer is used. In certain embodiments, a generation 5 alkyne-terminated PAMAM dendrimer is used. Dendrimers are not limited by their method of synthesis. The dendrimer may be synthesized by divergent synthesis methods or convergent synthesis methods. In certain embodiments of the present invention, dendrimer molecules may be modified. Modifications may include but are not limited to the addition of amine-blocking groups (e.g., acetyl groups), ligands, functional groups, conjugates, and/or linkers not originally present on the dendrimer. Modification may be partial or complete. In some embodiments, all of the termini of the dendrimer molecules are modified. In some embodiments, not all of the dendrimer molecules are modified. In preferred embodiments, methods and systems of the present invention permit identification and isolation of subpopulations of dendrimers with known numbers of ligand attachments (e.g., conjugations) per dendrimer molecule, thereby yielding samples or subpopulations of dendrimer compositions with high structural uniformity.

The present invention is not limited to particular ligand types (e.g., functional groups) (e.g., for conjugation with dendrimers). Examples of ligand types (e.g., functional groups) include but are not limited to therapeutic agents, targeting agents, trigger agents, and imaging agents. In some embodiments, the ligand is an alkyne ligand that includes an alkyne. In some embodiments, the ligand is an azide ligand that includes $N_3$. In some embodiments, the ligand includes an aromatic group. Methods, systems, and compositions of the present invention are not limited by the number of different ligand types used. There may be 1, 2, 3, 4, 5, 6, 7, 8, 9, 10, 50, 100 or more different types of ligands attached to a dendrimer molecule.

In some embodiments, conjugation between a ligand and a functional group or between functional groups is accomplished through use of a 1,3-dipolar cycloaddition reaction ("click chemistry"). 'Click chemistry' involves, for example, the coupling of two different moieties (e.g., a therapeutic agent and a functional group) (e.g., a first functional group and a second functional group) via a 1,3-dipolar cycloaddition reaction between an alkyne moiety (or equivalent thereof) on the surface of the first moeity and an azide moiety (or equivalent thereof) (or any active end group such as, for example, a primary amine end group, a hydroxyl end group, a carboxylic acid end group, a thiol end group, etc.) on the second moiety. 'Click' chemistry is an attractive coupling method because, for example, it can be performed with a wide variety of solvent conditions including aqueous environments. For example, the stable triazole ring that results from coupling the alkyne with the azide is frequently achieved at quantitative yields and is considered to be biologically inert (see, e.g., Rostovtsev, V. V.; et al., Angewandte Chemie-International Edition 2002, 41, (14), 2596; Wu, P.; et al., Angewandte Chemie-International Edition 2004, 43, (30), 3928-3932; each herein incorporated by reference in their entireties).

The present invention is not limited to particular therapeutic agents. Indeed, examples of therapeutic agents include, but are not limited to, chemotherapeutic agents, anti-oncogenic agents, anti-angiogenic agents, tumor suppressor agents, anti-microbial agents, expression constructs comprising a nucleic acid encoding a therapeutic protein, pain relief agents, pain relief agent antagonists, agents designed to treat inflammatory disease, agents designed to treat arthritis (e.g., rheumatoid arthritis), agents designed to treat inflammatory bowel disease, agents designed to treat an autoimmune disease, and agents designed to treat inflammatory pelvic disease.

Examples of therapeutic agents for treating arthritis include, but are not limited to, disease-modifying antirheumatic drugs (e.g., leflunomide, methotrexate, sulfasalazine, hydroxychloroquine), biologicals (e.g., rituximab, finfliximab, etanercept, adalimumab, golimumab), nonsteroidal anti-inflammatory drugs (e.g., ibuprofen, celecoxib, ketoprofen, naproxen, piroxicam, diclofenac), analgesics (e.g., acetaminophen, tramadol), immunomodulators (e.g., anakinra, abatacept), glucocorticoids (e.g., prednisone, methylprednisone), TNF-α inhibitors (e.g., adalimumab, certolizumab pegol, etanercept, golimumab, infliximab), an IL-1 inhibitor, and metalloprotease inhibitors. In some embodiments, the additional agents include, but are not limited to, infliximab, adalimumab, etanercept, parenteral gold or oral gold.

Functional ligands suitable for use in certain method embodiments of the present invention are not limited to a particular type or kind of targeting agent. While not limited to targeting a specific condition, disease and/or disorder, in some embodiments, the targeting agent is configured to target the composition to cells and/or tissue associated with an autoimmune disorder and/or inflammatory disorder (e.g., arthritis). In some embodiments, the targeting agent comprises folic acid. In some embodiments, the targeting agent binds a receptor selected from the group consisting of CFTR, EGFR, estrogen receptor, FGR2, folate receptor, IL-2 receptor, and VEGFR. In some embodiments, the targeting agent comprises an antibody that binds to a polypeptide selected from the group consisting of p53, Mucl, a mutated version of p53 that is present in breast cancer, HER-2, T and Tn haptens in glycoproteins of human breast carcinoma, and MSA breast carcinoma glycoprotein. In some embodiments, the targeting agent comprises an antibody selected from the group consisting of human carcinoma antigen, TP1 and TP3 antigens from osteocarcinoma cells, Thomsen-Friedenreich (TF) antigen from adenocarcinoma cells, KC-4 antigen from human prostrate adenocarcinoma, human colorectal cancer antigen, CA125 antigen from cystadenocarcinoma, DF3 antigen from human breast carcinoma, and p97 antigen of human melanoma, carcinoma or orosomucoid-related antigen. In some embodiments, the targeting agent is configured to permit the composition to cross the blood brain barrier. In some embodiments, the targeting agent is transferrin. In some embodiments, the targeting agent is configured to permit the composition to bind with a neuron within the central nervous system. In some embodiments, the targeting agent is a synthetic tetanus toxin fragment. In some embodiments, the synthetic tetanus toxin fragment comprises an amino acid peptide fragment. In some embodiments, the amino acid peptide fragment is HLNILSTLWKYR (SEQ ID NO:1). In some embodiments, the targeting agent is attached with the dendrimer via a linker. The present invention is not limited to a particular type or kind of linker. In some embodiments, the linker comprises a spacer comprising between 1 and 8 straight or branched carbon chains. In some embodiments, the straight or branched carbon chains are unsubstituted. In some embodiments, the straight or branched carbon chains are substituted with alkyls.

In some embodiments, the ligand comprises a trigger agent. The present invention is not limited to particular type or kind of trigger agent. In some embodiments, the trigger agent is configured to have a function such as, for example, a) a delayed release of a functional group from the dendrimer, b) a constitutive release of the therapeutic agent from the dendrimer, c) a release of a functional group from the dendrimer under conditions of acidosis, d) a release of a functional group from a dendrimer under conditions of hypoxia, and e) a release of the therapeutic agent from a dendrimer in the presence of a brain enzyme. Examples of trigger agents include, but are not limited to, an ester bond, an amide bond, an ether bond, an indoquinone, a nitroheterocyle, and a nitroimidazole. In some embodiments, the trigger agent is attached with the dendrimer via a linker. The present invention is not limited to a particular type or kind of linker. In some embodiments, the linker comprises a spacer comprising between 1 and 8 straight or branched carbon chains. In some embodiments, the straight or branched carbon chains are unsubstituted. In some embodiments, the straight or branched carbon chains are substituted with alkyls.

Ligands suitable for use in certain method embodiments of the present invention are not limited to a particular type or kind of imaging agent. In some embodiments, the imaging agent comprises fluorescein isothiocyanate (FITC) or 6-TAMARA. In some embodiments, the imaging agent comprises 3-azido-coumarine. In some embodiments, the imaging agent is attached with the dendrimer via a linker. The present invention is not limited to a particular type or kind of linker. In some embodiments, the linker comprises a spacer comprising between 1 and 8 straight or branched carbon chains. In some embodiments, the straight or branched carbon chains are unsubstituted. In some embodiments, the straight or branched carbon chains are substituted with alkyls.

In certain embodiments, the present invention provides compounds and/or pharmaceutical compositions configured for treating autoimmune disorders and/or inflammatory disorders (e.g., rheumatoid arthritis, ankylosing spondylitis, osteoarthritis, psoriatic arthritis, psoriasis, lupus erythematosus, Crohn's disease or sarcoidosis). In some embodiments, the compounds are described by formula 1:

groups, y is the average number of folates, and z is the average number of acetyl groups; wherein w is from 7 to 12, x is from 10-20, y is from 3-8 and z is from 65-108. In some embodiments, the average number of folates is from 3 to 6, or is from 4 to 6 or from 5 to 6, or is 4, 5, 6, 7 or 8. In some embodiments, the average number of methotrexates is from 8 to 10, or 7 to 10 or from 9 to 12 or is 7, 8, 9, 10, 11 or 12. In some embodiments, the present invention provides methods for synthesizing such compounds and/or pharmaceutical compositions configured for treating autoimmune disorders and/or inflammatory disorders (e.g., rheumatoid arthritis, ankylosing spondylitis, osteoarthritis, psoriatic arthritis, psoriasis, lupus erythematosus, Crohn's disease or sarcoidosis).

In some embodiments, the disorder is arthritis. The methods are not limited to a particular type of arthritis. Examples of arthritis include, but are not limited to, osteoarthritis, rheumatoid arthritis, septic arthritis, gout and pseudo-gout, juvenile idiopathic arthritis, Still's disease, and ankylosing spondylitis.

In certain embodiments, the present invention provides methods for treating subjects having autoimmune disorders and/or inflammatory disorders through administration of compositions comprising dendrimer compounds conjugated with functional ligands configured for treating such disorders. Examples of autoimmune disorders and/or inflammatory disorders include, but are not limited to, rheumatoid arthritis, ankylosing spondylitis, osteoarthritis, psoriatic arthritis, psoriasis, lupus erythematosus, Crohn's disease or sarcoidosis. Examples of arthritis include, but are not limited to, osteoarthritis, rheumatoid arthritis, septic arthritis, gout and pseudo-gout, juvenile idiopathic arthritis, Still's disease, and ankylosing spondylitis.

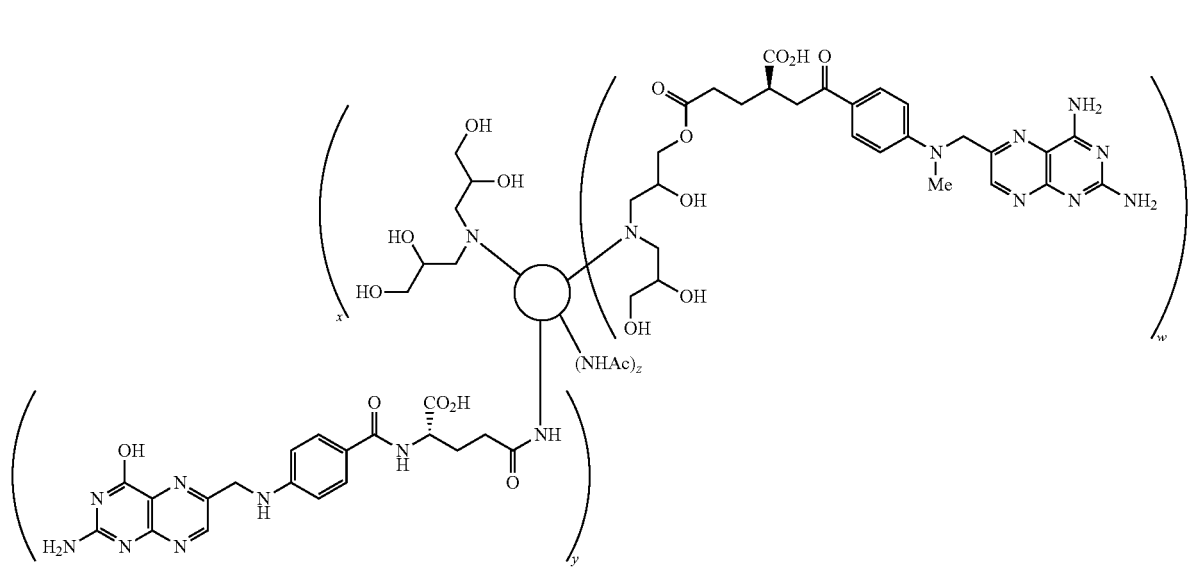

I wherein

represents a G5 PAMAM dendrimer wherein w is the average number of methotrexates, x is the average number of glycidol The methods are not limited to particular dendrimer compounds. In some embodiments, the dendrimers are PAMAM dendrimers. The compounds are not limited to particular functional ligands configured for treating autoimmune disorders and/or inflammatory disorders. In some embodiments, the dendrimer compounds are conjugated with methotrexate and folate. In some embodiments, the compounds are described by formula 1:

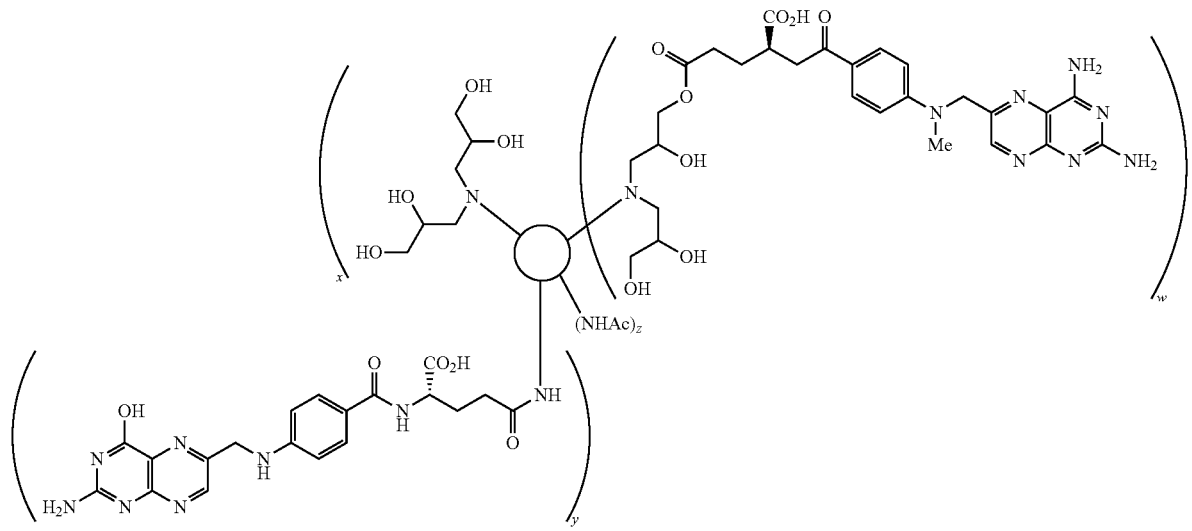

wherein

represents a G5 PAMAM dendrimer wherein w is the average number of methotrexates, x is the average number of glycidol groups, y is the average number of folates, and z is the average number of acetyl groups; wherein w is from 7 to 12, x is from 10-20, y is from 3-8 and z is from 65-108. In some embodiments, the average number of folates is from 3 to 6, or is from 4 to 6 or from 5 to 6, or is 4, 5, 6, 7 or 8. In some embodiments, the average number of methotrexates is from 8 to 10, or 7 to 10 or from 9 to 12 or is 7, 8, 9, 10, 11 or 12.

In some embodiments, the methods further comprise co-administering an effective amount of one or more additional agents configured for treating autoimmune disorders and/or inflammatory disorders. Examples of such additional agents include, but are not limited to, disease-modifying antirheumatic drugs (e.g., leflunomide, methotrexate, sulfasalazine, hydroxychloroquine), biologicals (e.g., rituximab, finfliximab, etanercept, adalimumab, golimumab), nonsteroidal anti-inflammatory drugs (e.g., ibuprofen, celecoxib, ketoprofen, naproxen, piroxicam, diclofenac), analgesics (e.g., acetaminophen, tramadol), immunomodulators (e.g., anakinra, abatacept), glucocorticoids (e.g., prednisone, methylprednisone), TNF-α inhibitors (e.g., adalimumab, certolizumab pegol, etanercept, golimumab, infliximab), an IL-1 inhibitor, and metalloprotease inhibitors. In some embodiments, the additional agents include, but are not limited to, infliximab, adalimumab, etanercept, parenteral gold or oral gold.

Additional embodiments will be apparent to persons skilled in the relevant art based on the teachings contained herein.

DESCRIPTION OF THE DRAWINGS

FIG. 17 shows blinded arthritis score for each rat where G2 are the rheumatoid arthritis rats treated with saline, G3 are the rheumatoid arthritis rats treated with methotrexate 0.25 mg/ml, G4 are the rheumatoid arthritis rats treated with methotrexate 0.75 mg/ml, and G1 is the negative control rats (no induced rheumatoid arthritis).

FIG. 24 shows blinded arthritis score for rheumatoid arthritis rats treated with saline, rheumatoid arthritis rats treated with G5-Ac-gly-MTX, rheumatoid arthritis rats treated with G5-Ac-FA-gly-MTX ("new batch"; less old than the "old batch"), rheumatoid arthritis rats treated with G5-Ac-FA-gly-MTX ("old batch"; older than the "new batch") and a negative control (no induced rheumatoid arthritis).

DEFINITIONS

Figure 1:
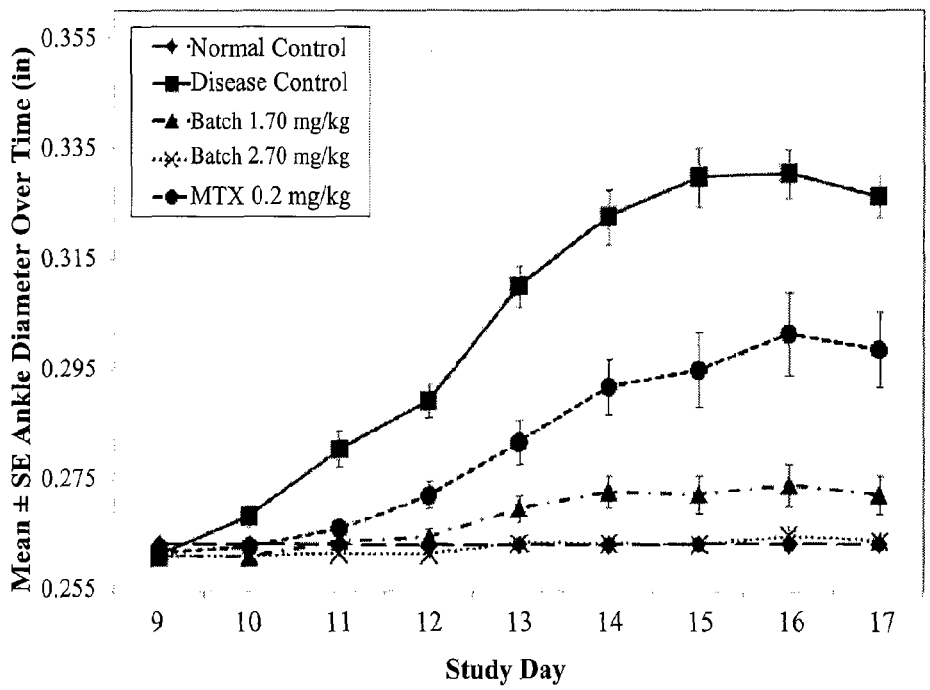
FIG. 1 depicts the time course of inhibition of ankle diameter in arthritic rats treated with ATI-101 Batch 1, Batch 2 or MTX as compared to disease controls.

To facilitate an understanding of the present invention, a number of terms and phrases are defined below:

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "non-human animals" refers to all non-human animals including, but not limited to, vertebrates such as rodents, non-human primates, ovines, bovines, ruminants, lagomorphs, porcines, caprines, equines, canines, felines, ayes, etc.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

As used herein, the term "drug" is meant to include any molecule, molecular complex or substance administered to an organism for diagnostic or therapeutic purposes, including medical imaging, monitoring, contraceptive, cosmetic, nutraceutical, pharmaceutical and prophylactic applications. The term "drug" is further meant to include any such molecule, molecular complex or substance that is chemically modified and/or operatively attached to a biologic or biocompatible structure.

As used herein, the term "purified" or "to purify" or "compositional purity" refers to the removal of components (e.g., contaminants) from a sample or the level of components (e.g., contaminants) within a sample. For example, unreacted moieties, degradation products, excess reactants, or byproducts are removed from a sample following a synthesis reaction or preparative method.

The terms "test compound" and "candidate compound" refer to any chemical entity, pharmaceutical, drug, and the like that is a candidate for use to treat or prevent a disease, illness, sickness, or disorder of bodily function (e.g., cancer). Test compounds comprise both known and potential therapeutic compounds. A test compound can be determined to be therapeutic by screening using screening methods known in the art.

As used herein, the term "nanodevice" or "nanodevices" refer, generally, to compositions comprising dendrimers of the present invention. As such, a nanodevice may refer to a composition comprising a dendrimer of the present invention that may contain one or more ligands, linkers, and/or functional groups (e.g., a therapeutic agent, a targeting agent, a trigger agent, an imaging agent) conjugated to the dendrimer.

As used herein, the term "degradable linkage," when used in reference to a polymer refers to a conjugate that comprises a physiologically cleavable linkage (e.g., a linkage that can be hydrolyzed (e.g., in vivo) or otherwise reversed (e.g., via enzymatic cleavage). Such physiologically cleavable linkages include, but are not limited to, ester, carbonate ester, carbamate, sulfate, phosphate, acyloxyalkyl ether, acetal, and ketal linkages (See, e.g., U.S. Pat. No. 6,838,076, herein incorporated by reference in its entirety). Similarly, the conjugate may comprise a cleavable linkage present in the linkage between the dendrimer and functional group, or, may comprise a cleavable linkage present in the polymer itself (See, e.g., U.S. Pat. App. Nos. 20050158273 and 20050181449, each of which is herein incorporated by reference in its entirety).

A "physiologically cleavable" or "hydrolysable" or "degradable" bond is a bond that reacts with water (i.e., is hydrolyzed) under physiological conditions. The tendency of a bond to hydrolyze in water will depend not only on the general type of linkage connecting two central atoms but also on the substituents attached to these central atoms. Appropriate hydrolytically unstable or weak linkages include but are not limited to carboxylate ester, phosphate ester, anhydrides, acetals, ketals, acyloxyalkyl ether, imines, orthoesters, peptides and oligonucleotides.

An "enzymatically degradable linkage" means a linkage that is subject to degradation by one or more enzymes.

As used herein, the term "NAALADase inhibitor" refers to any one of a multitude of inhibitors for the neuropeptidase NAALADase (N-acetylated-alpha linked acidic dipeptidase). Such inhibitors of NAALADase have been well characterizied. For example, an inhibitor can be selected from the group comprising, but not limited to, those found in U.S. Pat. No. 6,011,021, herein incorporated by reference in its entirety.

A "hydrolytically stable" linkage or bond refers to a chemical bond (e.g., typically a covalent bond) that is substantially stable in water (i.e., does not undergo hydrolysis under physiological conditions to any appreciable extent over an extended period of time). Examples of hydrolytically stable linkages include, but are not limited to, carbon-carbon bonds (e.g., in aliphatic chains), ethers, amides, urethanes, and the like.

As used herein, the term "click chemistry" refers to chemistry tailored to generate substances quickly and reliably by joining small modular units together (see, e.g., Kolb et al. (2001) Angewandte Chemie Intl. Ed. 40:2004-2011; Evans (2007) Australian J. Chem. 60:384-395; Carlmark et al. (2009) Chem. Soc. Rev. 38:352-362; each herein incorporated by reference in its entirety).

As used herein, an "ester coupling agent" refers to a reagent that can facilitate the formation of an ester bond between two reactants. The present invention is not limited to any particular coupling agent or agents. Examples of coupling agents include but are not limited to 2-chloro-1-methylpyridium iodide and 4-(dimethylamino) pyridine, or dicyclohexylcarbodiimide and 4-(dimethylamino) pyridine or diethyl azodicarboxylate and triphenylphosphine or other carbodiimide coupling agent and 4-(dimethylamino)pyridine.

As used herein, the term "glycidolate" refers to the addition of a 2,3-dihydroxylpropyl group to a reagent using glycidol as a reactant. In some embodiments, the reagent to which the 2,3-dihydroxylpropyl groups are added is a dendrimer. In some embodiments, the dendrimer is a PAMAM dendrimer. Glycidolation may be used generally to add terminal hydroxyl functional groups to a reagent.

As used herein, the term "ligand" refers to any moiety covalently attached (e.g., conjugated) to a dendrimer branch; in preferred embodiments, such conjugation is indirect (e.g., an intervening moiety exists between the dendrimer branch and the ligand) rather than direct (e.g., no intervening moiety exists between the dendrimer branch and the ligand). Indirect attachment of a ligand to a dendrimer may exist where a scaffold compound (e.g., triazine scaffold) intervenes. In preferred embodiments, ligands have functional utility for specific applications, e.g., for therapeutic, targeting, imaging, or drug delivery function(s). The terms "ligand", "conjugate", and "functional group" may be used interchangeably.

As used herein, the term "one-pot synthesis reaction" or equivalents thereof, e.g., "1-pot", "one pot", etc., refers to a chemical synthesis method in which all reactants are present in a single vessel. Reactants may be added simultaneously or sequentially, with no limitation as to the duration of time elapsing between introduction of sequentially added reactants.

As used herein, the term "amino alcohol" or "amino-alcohol" refers to any organic compound containing both an amino and an aliphatic hydroxyl functional group (e.g., which may be an aliphatic or branched aliphatic or alicyclic or hetero-alicyclic compound containing an amino group and one or more hydroxyl(s)). The generic structure of an amino alcohol may be expressed as $NH_2$—R—$(OH)_m$ wherein m is an integer, and wherein R comprises at least two carbon molecules (e.g., at least 2 carbon molecules, 10 carbon molecules, 25 carbon molecules, 50 carbon molecules).

As used herein, the term "Baker-Huang dendrimer" or "Baker-Huang PAMAM dendrimer" refers to a dendrimer comprised of branching units of structure:

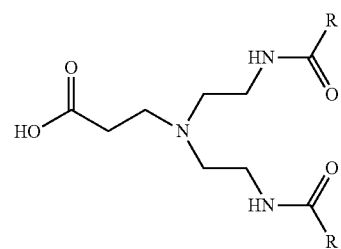

wherein R comprises a carbon-containing functional group (e.g., $CF_3$). In some embodiments, the branching unit is activated to its HNS ester. In some embodiments, such activation is achieved using TSTU. In some embodiments, EDA is added. In some embodiments, the dendrimer is further treated to replace, e.g., $CF_3$ functional groups with $NH_2$ functional groups; for example, in some embodiments, a $CF_3$-containing version of the dendrimer is treated with $K_2CO_3$ to yield a dendrimer with terminal $NH_2$ groups (for example, as shown in Scheme 2). In some embodiments, terminal groups of a Baker-Huang dendrimer are further derivatized and/or further conjugated with other moieties. For example, one or more functional ligands (e.g., for therapeutic, targeting, imaging, or drug delivery function(s)) may be conjugated to a Baker-Huang dendrimer, either via direct conjugation to terminal branches or indirectly (e.g., through linkers, through other functional groups (e.g., through an OH-functional group)). In some embodiments, the order of iterative repeats from core to surface is amide bonds first, followed by tertiary amines, with ethylene groups intervening between the amide bond and tertiary amines. In preferred embodiments, a Baker-Huang dendrimer is synthesized by convergent synthesis methods.

DETAILED DESCRIPTION OF THE INVENTION

Current treatments for rheumatoid arthritis include: non-steroidal anti-inflammatory drugs (NSAIDs), corticosteroids, gold therapy, methotrexate, tumor necrosis Factor Inhibitors such as etanercept (Enbrel®), adalimumab (Humira®), and infliximab (Remicade®), and other immunomodulatory and cytotoxic agents. While these treatments can be effective many require close supervision because of hazardous side effects. Response to treatment with these agents is variable and some patients still experience pain and joint degeneration. Thus, there is a need for additional forms of treatment that can treat rheumatoid arthritis and related diseases.

The present invention provides solutions for such issues. Indeed, experiments conducted during the course of developing some embodiments of the present invention determined that PAMAM dendrimers comprising specific functional ligands were effective in the treatment of autoimmune disorders and inflammatory disorders such as, for example, arthritis (e.g., rheumatoid arthritis). In particular, PAMAM dendrimers comprising functional ligands such as methotrexate and folate were shown to be effective in treating autoimmune disorders and inflammatory disorders. Examples of such disorders include, but are not limited to, rheumatoid arthritis, ankylosing spondylitis, osteoarthritis, psoriatic arthritis, psoriasis, lupus erythematosus, Crohn's disease and sarcoidosis.

In certain embodiments, the present invention provides compounds and/or pharmaceutical compositions configured for treating autoimmune disorders and/or inflammatory disorders (e.g., arthritis, ankylosing spondylitis, osteoarthritis, psoriatic arthritis, psoriasis, lupus erythematosus, Crohn's disease or sarcoidosis) with compounds described by formula 1:

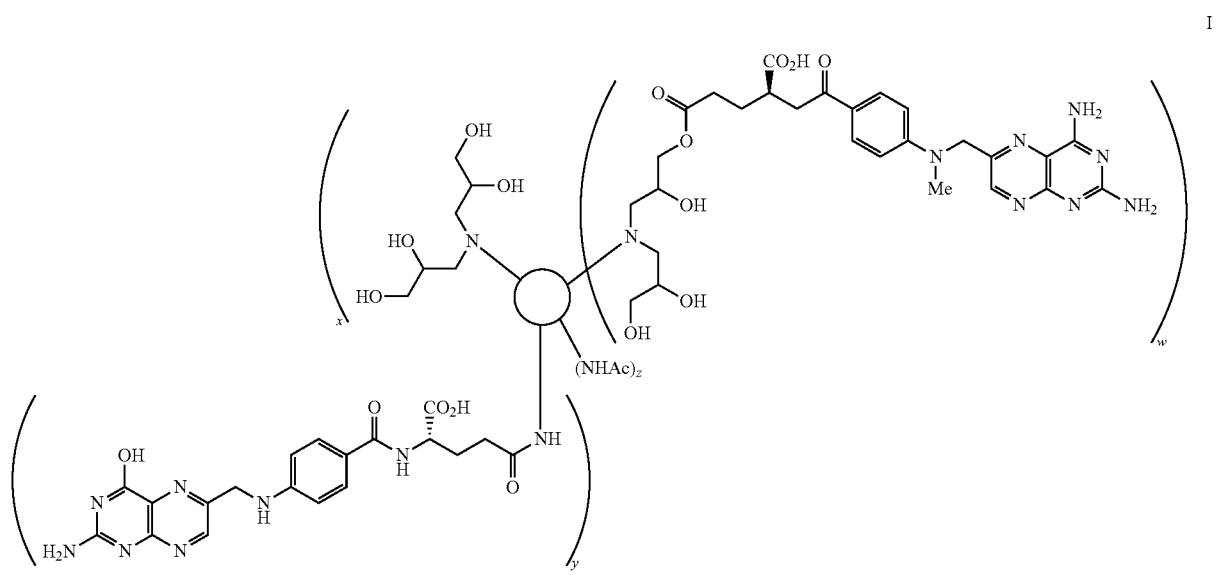

wherein represents a G5 PAMAM dendrimer wherein w is the average number of methotrexates, x is the average number of glycidol groups, y is the average number of folates, and z is the average number of acetyl groups; wherein w is from 7 to 12, x is from 10-20, y is from 3-8 and z is from 65-108. In some embodiments, the average number of folates is from 3 to 6, or is from 4 to 6 or from 5 to 6, or is 4, 5, 6, 7 or 8. In some embodiments, the average number of methotrexates is from 8 to 10, or 7 to 10 or from 9 to 12 or is 7, 8, 9, 10, 11 or 12. The compounds are not limited to treating a particular type of arthritis. Examples of arthritis include, but are not limited to, osteoarthritis, rheumatoid arthritis, septic arthritis, gout and pseudogout, juvenile idiopathic arthritis, Still's disease, and ankylosing spondylitis. The present invention provides methods for synthesizing such compounds and/or pharmaceutical compositions configured for treating autoimmune disorders and/or inflammatory disorders, as well as methods for treating subjects (e.g., human patients) suffering from autoimmune disorders and/or inflammatory disorders with such compounds.

Accordingly, the present invention relates to dendrimer compositions configured for treating inflammatory disorders and autoimmune disorders, and related methods of synthesis. Specifically, the present invention relates to methods for treating arthritis with PAMAM dendrimers having functional ligands configured for treating rheumatoid arthritis (e.g., therapeutic agents, pro-drugs, targeting agents, trigger agents, imaging agents) (e.g., methotrexate).

The present invention is not limited to the use of particular types and/or kinds of dendrimers. Indeed, dendrimeric polymers have been described extensively (See, e.g., Tomalia, Advanced Materials 6:529 (1994); Angew, Chem. Int. Ed. Engl., 29:138 (1990); incorporated herein by reference in their entireties). Dendrimer polymers are synthesized as defined spherical structures typically ranging from 1 to 20 nanometers in diameter. Methods for manufacturing a G5 PAMAM dendrimer with a protected core are known (U.S. patent application Ser. No. 12/403,179; herein incorporated by reference in its entirety). In preferred embodiments, the protected core diamine is $NH_2$—$CH_2$—$CH_2$—NHPG. Molecular weight and the number of terminal groups increase exponentially as a function of generation (the number of layers) of the polymer. In some embodiments of the present invention, half generation PAMAM dendrimers are used. For example, when an ethylenediamine (EDA) core is used for dendrimer synthesis, alkylation of this core through Michael addition results in a half-generation molecule with ester terminal groups; amidation of such ester groups with excess EDA results in creation of a full-generation, amine-terminated dendrimer (Majoros et al., Eds. (2008) Dendrimer-based Nanomedicine, Pan Stanford Publishing Pte. Ltd., Singapore, p. 42). Different types of dendrimers can be synthesized based on the core structure that initiates the polymerization process.

The dendrimer core structures dictate several characteristics of the molecule such as the overall shape, density and surface functionality (See, e.g., Tomalia et al., Chem. Int. Ed. Engl., 29:5305 (1990)). Spherical dendrimers can have ammonia as a trivalent initiator core or ethylenediamine (EDA) as a tetravalent initiator core. Recently described rod-shaped dendrimers (See, e.g., Yin et al., J. Am. Chem. Soc., 120:2678 (1998)) use polyethyleneimine linear cores of varying lengths; the longer the core, the longer the rod. Dendritic macromolecules are available commercially in kilogram quantities and are produced under current good manufacturing processes (GMP) for biotechnology applications.

Dendrimers may be characterized by a number of techniques including, but not limited to, electrospray-ionization mass spectroscopy, $^{13}C$ nuclear magnetic resonance spectroscopy, $^1H$ nuclear magnetic resonance spectroscopy, size exclusion chromatography with multi-angle laser light scattering, ultraviolet spectrophotometry, capillary electrophoresis and gel electrophoresis. These tests assure the uniformity of the polymer population and are important for monitoring quality control of dendrimer manufacture for GMP applications and in vivo usage.

Numerous U.S. Patents describe methods and compositions for producing dendrimers. Examples of some of these patents are given below in order to provide a description of some dendrimer compositions that may be useful in the present invention, however it should be understood that these are merely illustrative examples and numerous other similar dendrimer compositions could be used in the present invention.

U.S. Pat. Nos. 4,507,466, 4,558,120, 4,568,737, and 4,587,329 each describe methods of making dense star polymers with terminal densities greater than conventional star polymers. These polymers have greater/more uniform reactivity than conventional star polymers, i.e. 3rd generation dense star polymers. These patents further describe the nature of the amidoamine dendrimers and the 3-dimensional molecular diameter of the dendrimers.

U.S. Pat. No. 4,631,337 describes hydrolytically stable polymers. U.S. Pat. No. 4,694,064 describes rod-shaped dendrimers. U.S. Pat. No. 4,713,975 describes dense star polymers and their use to characterize surfaces of viruses, bacteria and proteins including enzymes. Bridged dense star polymers are described in U.S. Pat. No. 4,737,550. U.S. Pat. Nos. 4,857,599 and No. 4,871,779 describe dense star polymers on immobilized cores useful as ion-exchange resins, chelation resins and methods of making such polymers.

U.S. Pat. No. 5,338,532 is directed to starburst conjugates of dendrimer(s) in association with at least one unit of carried agricultural, pharmaceutical or other material. This patent describes the use of dendrimers to provide means of delivery of high concentrations of carried materials per unit polymer, controlled delivery, targeted delivery and/or multiple species such as e.g., drugs antibiotics, general and specific toxins, metal ions, radionuclides, signal generators, antibodies, interleukins, hormones, interferons, viruses, viral fragments, pesticides, and antimicrobials.

U.S. Pat. No. 6,471,968 describes a dendrimer complex comprising covalently linked first and second dendrimers, with the first dendrimer comprising a first agent and the second dendrimer comprising a second agent, wherein the first dendrimer is different from the second dendrimer, and where the first agent is different than the second agent.

Other useful dendrimer type compositions are described in U.S. Pat. Nos. 5,387,617, 5,393,797, and 5,393,795 in which dense star polymers are modified by capping with a hydrophobic group capable of providing a hydrophobic outer shell. U.S. Pat. No. 5,527,524 discloses the use of amino terminated dendrimers in antibody conjugates.

PAMAM dendrimers are highly branched, narrowly dispersed synthetic macromolecules with well-defined chemical structures. PAMAM dendrimers can be easily modified and conjugated with multiple functionalities such as targeting molecules, imaging agents, and drugs (Thomas et al. (2007) Poly(amidoamine) Dendrimer-based Multifunctional Nanoparticles, in Nanobiotechnology: Concepts, Methods and Perspectives, Merkin, Ed., Wiley-VCH; herein incorporated by reference in its entirety). They are water soluble, biocompatible, and cleared from the blood through the kidneys (Peer et al. (2007) Nat. Nanotechnol. 2:751-760; herein incorporated by reference in its entirety) which eliminates the need for biodegradability. Because of these desirable properties, PAMAM dendrimers have been widely investigated for drug delivery (Esfand et al. (2001) Drug Discov. Today 6:427-436; Patri et al. (2002) Curr. Opin. Chem. Biol. 6:466-471; Kukowska-Latallo et al. (2005) Cancer Res. 65:5317-5324; Quintana et al. (2002) Pharmaceutical Res. 19:1310-1316; Thomas et al. (2005) J. Med. Chem. 48:3729-3735; each herein incorporated by reference in its entirety), gene therapy (KukowskaLatallo et al. (1996) PNAS 93:4897-4902; Eichman et al. (2000) Pharm. Sci. Technolo. Today 3:232-245; Luo et al. (2002) Macromol. 35:3456-3462; each herein incorporated by reference in its entirety), and imaging applications (Kobayashi et al. (2003) Bioconj. Chem. 14:388-394; herein incorporated by reference in its entirety).

The use of dendrimers as metal ion carriers is described in U.S. Pat. No. 5,560,929. U.S. Pat. No. 5,773,527 discloses non-crosslinked polybranched polymers having a comb-burst configuration and methods of making the same. U.S. Pat. No. 5,631,329 describes a process to produce polybranched polymer of high molecular weight by forming a first set of branched polymers protected from branching; grafting to a core; deprotecting first set branched polymer, then forming a second set of branched polymers protected from branching and grafting to the core having the first set of branched polymers, etc.

U.S. Pat. No. 5,902,863 describes dendrimer networks containing lipophilic organosilicone and hydrophilic polyanicloamine nanscopic domains. The networks are prepared from copolydendrimer precursors having PAMAM (hydrophilic) or polyproyleneimine interiors and organosilicon outer layers. These dendrimers have a controllable size, shape and spatial distribution. They are hydrophobic dendrimers with an organosilicon outer layer that can be used for specialty membrane, protective coating, composites containing organic organometallic or inorganic additives, skin patch delivery, absorbants, chromatography personal care products and agricultural products.

U.S. Pat. No. 5,795,582 describes the use of dendrimers as adjuvants for influenza antigen. Use of the dendrimers produces antibody titer levels with reduced antigen dose. U.S. Pat. Nos. 5,898,005 and 5,861,319 describe specific immunobinding assays for determining concentration of an analyte. U.S. Pat. No. 5,661,025 provides details of a self-assembling polynucleotide delivery system comprising dendrimer polycation to aid in delivery of nucleotides to target site. This patent provides methods of introducing a polynucleotide into a eukaryotic cell in vitro comprising contacting the cell with a composition comprising a polynucleotide and a dendrimer polyeation non-covalently coupled to the polynucleotide.

Dendrimer-antibody conjugates for use in in vitro diagnostic applications have previously been demonstrated (See, e.g., Singh et al., Clin. Chem., 40:1845 (1994)), for the production of dendrimer-chelant-antibody constructs, and for the development of boronated dendrimer-antibody conjugates (for neutron capture therapy); each of these latter compounds may be used as a cancer therapeutic (See, e.g., Wu et al., Bioorg. Med. Chem. Lett., 4:449 (1994); Wiener et al., Magn. Reson. Med. 31:1 (1994); Barth et al., Bioconjugate Chem. 5:58 (1994); and Barth et al.).

Some of these conjugates have also been employed in the magnetic resonance imaging of tumors (See, e.g., Wu et al., (1994) and Wiener et al., (1994), supra). Results from this work have documented that, when administered in vivo, antibodies can direct dendrimer-associated therapeutic agents to antigen-bearing tumors. Dendrimers also have been shown to specifically enter cells and carry either chemotherapeutic agents or genetic therapeutics. In particular, studies show that cisplatin encapsulated in dendrimer polymers has increased efficacy and is less toxic than cisplatin delivered by other means (See, e.g., Duncan and Malik, Control Rel. Bioact. Mater. 23:105 (1996)).

Dendrimers have also been conjugated to fluorochromes or molecular beacons and shown to enter cells. They can then be detected within the cell in a manner compatible with sensing apparatus for evaluation of physiologic changes within cells (See, e.g., Baker et al., Anal. Chem. 69:990 (1997)). Finally, dendrimers have been constructed as differentiated block copolymers where the outer portions of the molecule may be digested with either enzyme or light-induced catalysis (See, e.g., Urdea and Hom, Science 261:534 (1993)). This allows the controlled degradation of the polymer to release therapeutics at the disease site and provides a mechanism for an external trigger to release the therapeutic agents.

The present invention is not limited to the use of particular therapeutic agents. In some embodiments, the therapeutic agents are effective in treating autoimmune disorders and/or inflammatory disorders (e.g., arthritis). Examples of such therapeutic agents include, but are not limited to, disease-modifying antirheumatic drugs (e.g., leflunomide, methotrexate, sulfasalazine, hydroxychloroquine), biologic agents (e.g., rituximab, infliximab, etanercept, adalimumab, golimumab), nonsteroidal anti-inflammatory drugs (e.g., ibuprofen, celecoxib, ketoprofen, naproxen, piroxicam, diclofenac), analgesics (e.g., acetaminophen, tramadol), immunomodulators (e.g., anakinra, abatacept), and glucocorticoids (e.g., prednisone, methylprednisone), TNF-$\alpha$ inhibitors (e.g., adalimumab, certolizumab pegol, etanercept, golimumab, infliximab), IL-1 inhibitors, and metalloprotease inhibitors. In some embodiments, the therapeutic agents include, but are not limited to, infliximab, adalimumab, etanercept, parenteral gold or oral gold.

In some embodiments, the therapeutic agents are effective in treating cancer (see, e.g., U.S. Pat. Nos. 6,471,968, 7,078, 461, and U.S. patent application Ser. Nos. 09/940,243, 10/431,682, 11,503,742, 11,661,465, 11/523,509, 12/403, 179, 12/106,876, 11/827,637, and 61/101,461; and U.S. Provisional Patent Application Ser. Nos. 61/256,759, 61/140, 840, 61/091,608, 61/097,780, 61/101,461, 61/237,172, 61/229,168, 61/221,596, and 61/251,244; each herein incorporated by reference in their entireties).

In some embodiments, the therapeutic agent is conjugated to a trigger agent. The present invention is not limited to particular types or kinds of trigger agents.

In some embodiments, sustained release (e.g., slow release over a period of 24-48 hours) of the therapeutic agent is accomplished through conjugating the therapeutic agent (e.g., directly) (e.g., indirectly through one or more additional functional groups) to a trigger agent that slowly degrades in a biological system (e.g., amide linkage, ester linkage, ether linkage). In some embodiments, constitutively active release of the therapeutic agent is accomplished through conjugating the therapeutic agent to a trigger agent that renders the therapeutic agent constitutively active in a biological system (e.g., amide linkage, ether linkage).

In some embodiments, release of the therapeutic agent under specific conditions is accomplished through conjugating the therapeutic agent (e.g., directly) (e.g., indirectly through one or more additional functional groups) to a trigger agent that degrades under such specific conditions (e.g., through activation of a trigger molecule under specific conditions that leads to release of the therapeutic agent). For example, once a conjugate (e.g., a therapeutic agent conjugated with a trigger agent and a targeting agent) arrives at a target site in a subject (e.g., a tumor, or a site of inflammation), components in the target site (e.g., a tumor associated factor, or an inflammatory or pain associated factor) interact with the trigger agent thereby initiating cleavage of the therapeutic agent from the trigger agent. In some embodiments, the trigger agent is configured to degrade (e.g., release the therapeutic agent) upon exposure to a tumor-associated factor (e.g., hypoxia and pH, an enzyme (e.g., glucuronidase and/or plasmin), a cathepsin, a matrix metalloproteinase, a hormone receptor (e.g., integrin receptor, hyaluronic acid receptor, luteinizing hormone-releasing hormone receptor, etc.), cancer and/or tumor specific DNA sequence), an inflammatory associated factor (e.g., chemokine, cytokine, etc.) or other moiety.

In some embodiments, the present invention provides a therapeutic agent conjugated with a trigger agent that is sensitive to (e.g., is cleaved by) hypoxia (e.g., indolequinone). Hypoxia is a feature of several disease states, including cancer, inflammation and rheumatoid arthritis, as well as an indicator of respiratory depression (e.g., resulting from analgesic drugs).

Advances in the chemistry of bioreductive drug activation have led to the design of various hypoxia-selective drug delivery systems in which the pharmacophores of drugs are masked by reductively cleaved groups. In some embodiments, the trigger agent is utilizes a quinone, N-oxide and/or (hetero)aromatic nitro groups. For example, a quinone present in a conjugate is reduced to phenol under hypoxia conditions, with spontaneous formation of lactone that serves as a driving force for drug release. In some embodiments, a heteroaromatic nitro compound present in a conjugate (e.g., a therapeutic agent conjugated (e.g., directly or indirectly) with a trigger agent) is reduced to either an amine or a hydroxylamine, thereby triggering the spontaneous release of a therapeutic agent. In some embodiments, the trigger agent degrades upon detection of reduced pO2 concentrations (e.g., through use of a redox linker).

The concept of pro-drug systems in which the pharmacophores of drugs are masked by reductively cleavable groups has been widely explored by many research groups and pharmaceutical companies (see, e.g., Beall, H. D., et al., Journal of Medicinal Chemistry, 1998. 41(24): p. 4755-4766; Ferrer, S., D. P. Naughton, and M. D. Threadgill, Tetrahedron, 2003. 59(19): p. 3445-3454; Naylor, M. A., et al., Journal of Medicinal Chemistry, 1997. 40(15): p. 2335-2346; Phillips, R. M., et al., Journal of Medicinal Chemistry, 1999. 42(20): p. 4071-4080; Zhang, Z., et al., Organic & Biomolecular Chemistry, 2005. 3(10): p. 1905-1910; each of which are herein incorporated by reference in their entireties). Several such hypoxia activated pro-drugs have been advanced to clinical investigations, and work in relevant oxygen concentrations to prevent cerebral damage. The present invention is not limited to particular hypoxia-activated trigger agents. In some embodiments, the hypoxia-activated trigger agents include, but are not limited to, indolequinones, nitroimidazoles, and nitroheterocycles (see, e.g., Damen, E. W. P., et al., Bioorganic & Medicinal Chemistry, 2002. 10(1): p. 71-77; Hay, M. P., et al., Journal of Medicinal Chemistry, 2003. 46(25): p. 5533-5545; Hay, M. P., et al., Journal of the Chemical Society-Perkin Transactions 1, 1999(19): p. 2759-2770; each herein incorporated by reference in their entireties).

In some embodiments, the trigger agent is sensitive to (e.g., is cleaved by) and/or associates with a tumor-associated enzyme. For example, in some embodiments, the trigger agent that is sensitive to (e.g., is cleaved by) and/or associates with a glucuronidase. Glucuronic acid can be attached to several anticancer drugs via various linkers. These anticancer drugs include, but are not limited to, doxorubicin, paclitaxel, docetaxel, 5-fluorouracil, 9-aminocamtothecin, as well as other drugs under development. These pro-drugs are generally stable at physiological pH and are significantly less toxic than the parent drugs.

In some embodiments, the trigger agent is sensitive to (e.g., is cleaved by) and/or associates with brain enzymes. For example, trigger agents such as indolequinone are reduced by brain enzymes such as, for example, diaphorase (DT-diaphorase) (see, e.g., Damen, E. W. P., et al., Bioorganic & Medicinal Chemistry, 2002. 10(1): p. 71-77; herein incorporated by reference in its entirety). For example, in such embodiments, the antagonist is only active when released during hypoxia to prevent respiratory failure.

In some embodiments, the trigger agent is sensitive to (e.g., is cleaved by) and/or associates with a protease. The present invention is not limited to any particular protease. In some embodiments, the protease is a cathepsin. In some embodiments, a trigger comprises a Lys-Phe-PABC moiety (e.g., that acts as a trigger). In some embodiments, a Lys-Phe-PABC moiety linked to doxorubicin, mitomycin C, and paclitaxel are utilized as a trigger-therapeutic conjugate in a dendrimer conjugate provided herein (e.g., that serve as substrates for lysosomal cathepsin B or other proteases expressed (e.g., overexpressed) in tumor cells. In some embodiments, utilization of a 1,6-elimination spacer/linker is utilized (e.g., to permit release of therapeutic drug post activation of trigger).

In some embodiments, the trigger agent is sensitive to (e.g., is cleaved by) and/or associates with plasmin. The serine protease plasmin is over expressed in many human tumor tissues. Tripeptide specifiers (e.g., including, but not limited to, Val-Leu-Lys) have been identified and linked to anticancer drugs through elimination or cyclization linkers.

In some embodiments, the trigger agent is sensitive to (e.g., is cleaved by) and/or associates with a matrix metalloprotease (MMP). In some embodiments, the trigger agent is sensitive to (e.g., is cleaved by) and/or that associates with β-Lactamase (e.g., a β-Lactamase activated cephalosporin-based pro-drug).

In some embodiments, the trigger agent is sensitive to (e.g., is cleaved by) and/or activated by a receptor (e.g., expressed on a target cell (e.g., a tumor cell)).

In some embodiments, the trigger agent that is sensitive to (e.g., is cleaved by) and/or activated by a nucleic acid. Nucleic acid triggered catalytic drug release can be utilized in the design of chemotherapeutic agents. Thus, in some embodiments, disease specific nucleic acid sequence is utilized as a drug releasing enzyme-like catalyst (e.g., via complex formation with a complimentary catalyst-bearing nucleic acid and/or analog). In some embodiments, the release of a therapeutic agent is facilitated by the therapeutic component being attached to a labile protecting group, such as, for example, cisplatin or methotrexate being attached to a photolabile protecting group that becomes released by laser light directed at cells emitting a color of fluorescence (e.g., in addition to and/or in place of target activated activation of a trigger component of a dendrimer conjugate). In some embodiments, the therapeutic device also may have a component to monitor the response of the tumor to therapy. For example, where a therapeutic agent of the dendrimer induces apoptosis of a target cell (e.g., a cancer cell (e.g., a prostate cancer cell)), the caspase activity of the cells may be used to activate a green fluorescence. This allows apoptotic cells to turn orange, (combination of red and green) while residual cells remain red. Any normal cells that are induced to undergo apoptosis in collateral damage fluoresce green.

In some embodiments, therapeutic agent is conjugated (e.g., directly or indirectly) to a targeting agent. The present invention is not limited to any particular targeting agent. In some embodiments, targeting agents are conjugated to the therapeutic agents for delivery of the therapeutic agents to desired body regions (e.g., to the central nervous system (CNS); to a tissue region associated with an inflammatory disorder and/or an autoimmune disorder (e.g., arthritis)). The targeting agents are not limited to targeting specific body regions.

In some embodiments, the targeting agent is a moiety that has affinity for a tumor associated factor. For example, a number of targeting agents are contemplated to be useful in the present invention including, but not limited to, RGD sequences, low-density lipoprotein sequences, a NAALADase inhibitor, epidermal growth factor, and other agents that bind with specificity to a target cell (e.g., a cancer cell)).

The present invention is not limited to cancer and/or tumor targeting agents. Indeed, multifunctional dendrimers can be targeted (e.g., via a linker conjugated to the dendrimer wherein the linker comprises a targeting agent) to a variety of target cells or tissues (e.g., to a biologically relevant environment) via conjugation to an appropriate targeting agent. For example, in some embodiments, the targeting agent is a moiety that has affinity for an inflammatory factor (e.g., a cytokine or a cytokine receptor moiety (e.g., TNF-α receptor)). In some embodiments, the targeting agent is a sugar, peptide, antibody or antibody fragment, hormone, hormone receptor, or the like.

In some embodiments of the present invention, the targeting agent includes but is not limited to an antibody, receptor ligand, hormone, vitamin, and antigen; however, the present invention is not limited by the nature of the targeting agent. In some embodiments, the antibody is specific for a disease-specific antigen. In some embodiments, the disease-specific antigen comprises a tumor-specific antigen. In some embodiments, the receptor ligand includes, but is not limited to, a ligand for CFTR, EGFR, estrogen receptor, FGR2, folate receptor, IL-2 receptor, glycoprotein, and VEGFR. In some embodiments, the receptor ligand is folic acid.

Antibodies can be generated to allow for the targeting of antigens or immunogens (e.g., tumor, tissue or pathogen specific antigens) on various biological targets (e.g., pathogens, tumor cells, normal tissue). Such antibodies include but are not limited to polyclonal, monoclonal, chimeric, single chain, Fab fragments, and an Fab expression library.

In some embodiments, the targeting agent is an antibody. In some embodiments, the antibodies recognize, for example, tumor-specific epitopes (e.g., TAG-72 (See, e.g., Kjeldsen et al., Cancer Res. 48:2214-2220 (1988); U.S. Pat. Nos. 5,892,020; 5,892,019; and 5,512,443; each herein incorporated by reference in their entireties); human carcinoma antigen (See, e.g., U.S. Pat. Nos. 5,693,763; 5,545,530; and 5,808,005; each herein incorporated by reference in their entireties); TP1 and TP3 antigens from osteocarcinoma cells (See, e.g., U.S. Pat. No. 5,855,866; herein incorporated by reference in its entirety); Thomsen-Friedenreich (TF) antigen from adenocarcinoma cells (See, e.g., U.S. Pat. No. 5,110,911; herein incorporated by reference in its entirety); "KC-4 antigen" from human prostrate adenocarcinoma (See, e.g., U.S. Pat. Nos. 4,708,930 and 4,743,543; each herein incorporated by reference in their entireties); a human colorectal cancer antigen (See, e.g., U.S. Pat. No. 4,921,789; herein incorporated by reference in its entirety); CA125 antigen from cystadenocarcinoma (See, e.g., U.S. Pat. No. 4,921,790; herein incorporated by reference in its entirety); DF3 antigen from human breast carcinoma (See, e.g., U.S. Pat. Nos. 4,963,484 and 5,053,489; each herein incorporated by reference in their entireties); a human breast tumor antigen (See, e.g., U.S. Pat. No. 4,939,240: herein incorporated by reference in its entirety); p97 antigen of human melanoma (See, e.g., U.S. Pat. No. 4,918,164: herein incorporated by reference in its entirety); carcinoma or orosomucoid-related antigen (CORA)(See, e.g., U.S. Pat. No. 4,914,021; herein incorporated by reference in its entirety); a human pulmonary carcinoma antigen that reacts with human squamous cell lung carcinoma but not with human small cell lung carcinoma (See, e.g., U.S. Pat. No. 4,892,935; herein incorporated by reference in its entirety); T and Tn haptens in glycoproteins of human breast carcinoma (See, e.g., Springer et al., Carbohydr. Res. 178:271-292 (1988); herein incorporated by reference in its entirety), MSA breast carcinoma glycoprotein termed (See, e.g., Tjandra et al., Br. J. Surg. 75:811-817 (1988); herein incorporated by reference in its entirety); MFGM breast carcinoma antigen (See, e.g., Ishida et al., Tumor Biol. 10:12-22 (1989); herein incorporated by reference in its entirety); DU-PAN-2 pancreatic carcinoma antigen (See, e.g., Lan et al., Cancer Res. 45:305-310 (1985); herein incorporated by reference in its entirety); CA125 ovarian carcinoma antigen (See, e.g., Hanisch et al., Carbohydr. Res. 178:29-47 (1988); herein incorporated by reference in its entirety); YH206 lung carcinoma antigen (See, e.g., Hinoda et al., (1988) Cancer J. 42:653-658 (1988); herein incorporated by reference in its entirety).

In some embodiments, the targeting agents target the central nervous system (CNS). In some embodiments, where the targeting agent is specific for the CNS, the targeting agent is transferrin (see, e.g., Daniels, T. R., et al., Clinical Immunology, 2006. 121(2): p. 159-176; Daniels, T. R., et al., Clinical Immunology, 2006. 121(2): p. 144-158; each herein incorporated by reference in their entireties). Transferrin has been utilized as a targeting vector to transport, for example, drugs, liposomes and proteins across the blood-brain barrier (BBB) by receptor mediated transcytosis (see, e.g., Smith, M. W. and M. Gumbleton, Journal of Drug Targeting, 2006. 14(4): p. 191-214; herein incorporated by reference in its entirety). In some embodiments, the targeting agents target neurons within the central nervous system (CNS). In some embodiments, where the targeting agent is specific for neurons within the CNS, the targeting agent is a synthetic tetanus toxin fragment (e.g., a 12 amino acid peptide (Tet 1) (HLNILSTL-WKYR) (SEQ ID NO:1)) (see, e.g., Liu, J. K., et al., Neurobiology of Disease, 2005. 19(3): p. 407-418; herein incorporated by reference in its entirety).

In some embodiments, the dendrimer is conjugated (e.g., directly or indirectly) to an imaging agent. A multiplicity of imaging agents find use in the present invention. In some embodiments, a multifunctional dendrimer comprises at least one imaging agent that can be readily imaged. The present invention is not limited by the nature of the imaging component used. In some embodiments of the present invention, imaging modules comprise surface modifications of quantum dots (See e.g., Chan and Nie, Science 281:2016 (1998)) such as zinc sulfide-capped cadmium selenide coupled to biomolecules (Sooklal, Adv. Mater., 10:1083 (1998)).

In some embodiments, once a component(s) of a targeted multifunctional dendrimer has attached to (or been internalized into) a target cell (e.g., tumor cell and or inflammatory cell), one or more modules serves to image its location. In some embodiments, chelated paramagnetic ions, such as Gd(III)-diethylenetriaminepentaacetic acid (Gd(III)-DTPA), are conjugated to the multifunctional dendrimer. Other paramagnetic ions that may be useful in this context include, but are not limited to, gadolinium, manganese, copper, chromium, iron, cobalt, erbium, nickel, europium, technetium, indium, samarium, dysprosium, ruthenium, ytterbium, yttrium, and holmium ions and combinations thereof.

Dendrimeric gadolinium contrast agents have even been used to differentiate between benign and malignant breast tumors using dynamic MRI, based on how the vasculature for the latter type of tumor images more densely (Adam et al., Ivest. Rad. 31:26 (1996)). Thus, MRI provides a particularly useful imaging system of the present invention.

Multifunctional dendrimers allow functional microscopic imaging of tumors and provide improved methods for imaging. The methods find use in vivo, in vitro, and ex vivo. For example, in one embodiment, dendrimer functional groups are designed to emit light or other detectable signals upon exposure to light. Although the labeled functional groups may be physically smaller than the optical resolution limit of the microscopy technique, they become self-luminous objects when excited and are readily observable and measurable using optical techniques. In some embodiments of the present invention, sensing fluorescent biosensors in a microscope involves the use of tunable excitation and emission filters and multiwavelength sources (See, e.g., Farkas et al., SPEI 2678:

200 (1997); herein incorporated by reference in its entirety). In embodiments where the imaging agents are present in deeper tissue, longer wavelengths in the Near-infrared (NMR) are used (See e.g., Lester et al., Cell Mol. Biol. 44:29 (1998); herein incorporated by reference in its entirety). Biosensors that find use with the present invention include, but are not limited to, fluorescent dyes and molecular beacons.

In some embodiments of the present invention, in vivo imaging is accomplished using functional imaging techniques. Functional imaging is a complementary and potentially more powerful techniques as compared to static structural imaging. Functional imaging is best known for its application at the macroscopic scale, with examples including functional Magnetic Resonance Imaging (fMRI) and Positron Emission Tomography (PET). However, functional microscopic imaging may also be conducted and find use in in vivo and ex vivo analysis of living tissue. Functional microscopic imaging is an efficient combination of 3-D imaging, 3-D spatial multispectral volumetric assignment, and temporal sampling: in short a type of 3-D spectral microscopic movie loop. Interestingly, cells and tissues autofluoresce. When excited by several wavelengths, providing much of the basic 3-D structure needed to characterize several cellular components (e.g., the nucleus) without specific labeling. Oblique light illumination is also useful to collect structural information and is used routinely. As opposed to structural spectral microimaging, functional spectral microimaging may be used with biosensors, which act to localize physiologic signals within the cell or tissue. For example, in some embodiments, biosensor-comprising pro-drug complexes are used to image upregulated receptor families such as the folate or EGF classes. In such embodiments, functional biosensing therefore involves the detection of physiological abnormalities relevant to carcinogenesis or malignancy, even at early stages. A number of physiological conditions may be imaged using the compositions and methods of the present invention including, but not limited to, detection of nanoscopic biosensors for pH, oxygen concentration, $Ca^{2+}$concentration, and other physiologically relevant analytes.

In some embodiments, the present invention provides multifunctional dendrimers having a biological monitoring component. The biological monitoring or sensing component of a multifunctional dendrimer is one that can monitor the particular response in a target cell (e.g., tumor cell) induced by an agent (e.g., a therapeutic agent provided by a multifunctional dendrimer). While the present invention is not limited to any particular monitoring system, the invention is illustrated by methods and compositions for monitoring cancer treatments. In preferred embodiments of the present invention, the agent induces apoptosis in cells and monitoring involves the detection of apoptosis. In some embodiments, the monitoring component is an agent that fluoresces at a particular wavelength when apoptosis occurs. For example, in a preferred embodiment, caspase activity activates green fluorescence in the monitoring component. Apoptotic cancer cells, which have turned red as a result of being targeted by a particular signature with a red label, turn orange while residual cancer cells remain red. Normal cells induced to undergo apoptosis (e.g., through collateral damage), if present, will fluoresce green.

In these embodiments, fluorescent groups such as fluorescein are employed in the imaging agent. Fluorescein is easily attached to the dendrimer surface via the isothiocyanate derivatives, available from MOLECULAR PROBES, Inc. This allows the multifunctional dendrimer or components thereof to be imaged with the cells via confocal microscopy. Sensing of the effectiveness of the multifunctional dendrimer or components thereof is preferably achieved by using fluorogenic peptide enzyme substrates. For example, apoptosis caused by the therapeutic agent results in the production of the peptidase caspase-1 (ICE). CALBIOCHEM sells a number of peptide substrates for this enzyme that release a fluorescent moiety. A particularly useful peptide for use in the present invention is: MCA-Tyr-Glu-Val-Asp-Gly-Trp-Lys-(DNP)-$NH_2$ (SEQ ID NO: 2) where MCA is the (7-methoxy-coumarin-4-yl)acetyl and DNP is the 2,4-dinitrophenyl group (See, e.g., Talanian et al., J. Biol. Chem., 272: 9677 (1997); herein incorporated by reference in its entirety). In this peptide, the MCA group has greatly attenuated fluorescence, due to fluorogenic resonance energy transfer (FRET) to the DNP group. When the enzyme cleaves the peptide between the aspartic acid and glycine residues, the MCA and DNP are separated, and the MCA group strongly fluoresces green (excitation maximum at 325 nm and emission maximum at 392 nm). In some embodiments, the lysine end of the peptide is linked to pro-drug complex, so that the MCA group is released into the cytosol when it is cleaved. The lysine end of the peptide is a useful synthetic handle for conjugation because, for example, it can react with the activated ester group of a bifunctional linker such as Mal-PEG-OSu. Thus the appearance of green fluorescence in the target cells produced using these methods provides a clear indication that apoptosis has begun (if the cell already has a red color from the presence of aggregated quantum dots, the cell turns orange from the combined colors).

Additional fluorescent dyes that find use with the present invention include, but are not limited to, acridine orange, reported as sensitive to DNA changes in apoptotic cells (see, e.g., Abrams et al., Development 117:29 (1993); herein incorporated by reference in its entirety) and cis-parinaric acid, sensitive to the lipid peroxidation that accompanies apoptosis (see, e.g., Hockenbery et al., Cell 75:241 (1993); herein incorporated by reference in its entirety). It should be noted that the peptide and the fluorescent dyes are merely exemplary. It is contemplated that any peptide that effectively acts as a substrate for a caspase produced as a result of apoptosis finds use with the present invention.

In some embodiments, conjugation between a dendrimer (e.g., terminal arm of a dendrimer) and a functional group or between functional groups is accomplished through use of a 1,3-dipolar cycloaddition reaction ("click chemistry"). 'Click chemistry' involves, for example, the coupling of two different moieties (e.g., a therapeutic agent and a functional group) (e.g., a first functional group and a second functional group) via a 1,3-dipolar cycloaddition reaction between an alkyne moiety (or equivalent thereof) on the surface of the first moeity and an azide moiety (e.g., present on a triazine composition of the present invention) (or equivalent thereof) (or any active end group such as, for example, a primary amine end group, a hydroxyl end group, a carboxylic acid end group, a thiol end group, etc.) on the second moiety. 'Click' chemistry is an attractive coupling method because, for example, it can be performed with a wide variety of solvent conditions including aqueous environments. For example, the stable triazole ring that results from coupling the alkyne with the azide is frequently achieved at quantitative yields and is considered to be biologically inert (see, e.g., Rostovtsev, V. V.; et al., Angewandte Chemie-International Edition 2002, 41, (14), 2596; Wu, P.; et al., Angewandte Chemie-International Edition 2004, 43, (30), 3928-3932; each herein incorporated by reference in their entireties).

In some embodiments, conjugation between a dendrimer (e.g., a terminal arm of a dendrimer) and a functional ligand is accomplished during a "one-pot" reaction. The term "one-pot synthesis reaction" or equivalents thereof, e.g., "1-pot", "one pot", etc., refers to a chemical synthesis method in which all reactants are present in a single vessel. Reactants may be added simultaneously or sequentially, with no limitation as to the duration of time elapsing between introduction of sequentially added reactants. In some embodiments, a one-pot reaction occurs wherein a hydroxyl-terminated dendrimer (e.g., HO-PAMAM dendrimer) is reacted with one or more functional ligands (e.g., a therapeutic agent, a pro-drug, a trigger agent, a targeting agent, an imaging agent) in one vessel, such conjugation being facilitated by ester coupling agents (e.g., 2-chloro-1-methylpyridinium iodide and 4-(dimethylamino) pyridine) (see, e.g., U.S. Patent App. No. 61/226,993, herein incorporated by reference in its entirety).

The present invention is not limited by the type of therapeutic agent delivered via multifunctional dendrimers of the present invention. For example, a therapeutic agent may be any agent selected from the group comprising, but not limited to, autoimmune disorder agent and/or an inflammatory disorder agent. Additional examples of therapeutic agents include, but are not limited to, a pain relief agent, a pain relief agent antagonist, a chemotherapeutic agent, an anti-oncogenic agent, an anti-angiogenic agent, a tumor suppressor agent, an anti-microbial agent, or an expression construct comprising a nucleic acid encoding a therapeutic protein.

It is contemplated that components of multifunctional dendrimers of the present invention provide therapeutic benefits to patients suffering from autoimmune disorders and/or inflammatory disorders. Indeed, in some embodiments of the present invention, methods and compositions are provided for the treatment of inflammatory diseases (e.g., dendrimers conjugated with therapeutic agents configured for treating inflammatory diseases). Inflammatory diseases include but are not limited to arthritis, rheumatoid arthritis, psoriatic arthritis, osteoarthritis, degenerative arthritis, polymyalgia rheumatic, ankylosing spondylitis, reactive arthritis, gout, pseudogout, inflammatory joint disease, systemic lupus erythematosus, polymyositis, and fibromyalgia. Additional types of arthritis include achilles tendinitis, achondroplasia, acromegalic arthropathy, adhesive capsulitis, adult onset Still's disease, anserine bursitis, avascular necrosis, Behcet's syndrome, bicipital tendinitis, Blount's disease, brucellar spondylitis, bursitis, calcaneal bursitis, calcium pyrophosphate dihydrate deposition disease (CPPD), crystal deposition disease, Caplan's syndrome, carpal tunnel syndrome, chondrocalcinosis, chondromalacia patellae, chronic synovitis, chronic recurrent multifocal osteomyelitis, Churg-Strauss syndrome, Cogan's syndrome, corticosteroid-induced osteoporosis, costosternal syndrome, CREST syndrome, cryoglobulinemia, degenerative joint disease, dermatomyositis, diabetic finger sclerosis, diffuse idiopathic skeletal hyperostosis (DISH), discitis, discoid lupus erythematosus, drug-induced lupus, Duchenne's muscular dystrophy, Dupuytren's contracture, Ehlers-Danlos syndrome, enteropathic arthritis, epicondylitis, erosive inflammatory osteoarthritis, exercise-induced compartment syndrome, Fabry's disease, familial Mediterranean fever, Farber's lipogranulomatosis, Felty's syndrome, Fifth's disease, flat feet, foreign body synovitis, Freiberg's disease, fungal arthritis, Gaucher's disease, giant cell arteritis, gonococcal arthritis, Goodpasture's syndrome, granulomatous arteritis, hemarthrosis, hemochromatosis, Henoch-Schonlein purpura, Hepatitis B surface antigen disease, hip dysplasia, Hurler syndrome, hypermobility syndrome, hypersensitivity vasculitis, hypertrophic osteoarthropathy, immune complex disease, impingement syndrome, Jaccoud's arthropathy, juvenile ankylosing spondylitis, juvenile dermatomyositis, juvenile rheumatoid arthritis, Kawasaki disease, Kienbock's disease, Legg-Calve-Perthes disease, Lesch-Nyhan syndrome, linear scleroderma, lipoid dermatoarthritis, Lofgren's syndrome, Lyme disease, malignant synovioma, Marfan's syndrome, medial plica syndrome, metastatic carcinomatous arthritis, mixed connective tissue disease (MCTD), mixed cryoglobulinemia, mucopolysaccharidosis, multicentric reticulohistiocytosis, multiple epiphyseal dysplasia, mycoplasmal arthritis, myofascial pain syndrome, neonatal lupus, neuropathic arthropathy, nodular panniculitis, ochronosis, olecranon bursitis, Osgood-Schlatter's disease, osteoarthritis, osteochondromatosis, osteogenesis imperfecta, osteomalacia, osteomyelitis, osteonecrosis, osteoporosis, overlap syndrome, pachydermoperiostosis Paget's disease of bone, palindromic rheumatism, patellofemoral pain syndrome, Pellegrini-Stieda syndrome, pigmented villonodular synovitis, piriformis syndrome, plantar fasciitis, polyarteritis nodos, Polymyalgia rheumatic, polymyositis, popliteal cysts, posterior tibial tendinitis, Pott's disease, prepatellar bursitis, prosthetic joint infection, pseudoxanthoma elasticum, psoriatic arthritis, Raynaud's phenomenon, reactive arthritis/Reiter's syndrome, reflex sympathetic dystrophy syndrome, relapsing polychondritis, retrocalcaneal bursitis, rheumatic fever, rheumatoid vasculitis, rotator cuff tendinitis, sacroiliitis, salmonella osteomyelitis, sarcoidosis, saturnine gout, Scheuermann's osteochondritis, scleroderma, septic arthritis, seronegative arthritis, shigella arthritis, shoulder-hand syndrome, sickle cell arthropathy, Sjogren's syndrome, slipped capital femoral epiphysis, spinal stenosis, spondylolysis, staphylococcus arthritis, Stickler syndrome, subacute cutaneous lupus, Sweet's syndrome, Sydenham's chorea, syphilitic arthritis, systemic lupus erythematosus (SLE), Takayasu's arteritis, tarsal tunnel syndrome, tennis elbow, Tietse's syndrome, transient osteoporosis, traumatic arthritis, trochanteric bursitis, tuberculosis arthritis, arthritis of Ulcerative colitis, undifferentiated connective tissue syndrome (UCTS), urticarial vasculitis, viral arthritis, Wegener's granulomatosis, Whipple's disease, Wilson's disease, and yersinial arthritis.

In some embodiments, the dendrimer conjugates configured for treating autoimmune disorders and/or inflammatory disorders (e.g., rheumatoid arthritis) are co-administered to a subject (e.g., a human suffering from an autoimmune disorder and/or an inflammatory disorder) a therapeutic agent configured for treating autoimmune disorders and/or inflammatory disorders (e.g., rheumatoid arthritis). Examples of such agents include, but are not limited to, disease-modifying anti-rheumatic drugs (e.g., leflunomide, methotrexate, sulfasalazine, hydroxychloroquine), biologic agents (e.g., rituximab, infliximab, etanercept, adalimumab, golimumab), nonsteroidal anti-inflammatory drugs (e.g., ibuprofen, celecoxib, ketoprofen, naproxen, piroxicam, diclofenac), analgesics (e.g., acetaminophen, tramadol), immunomodulators (e.g., anakinra, abatacept), and glucocorticoids (e.g., prednisone, methylprednisone).

The present invention also includes methods involving co-administration of the multifunctional dendrimers and components thereof described herein with one or more additional active agents. Indeed, it is a further aspect of this invention to provide methods for enhancing prior art therapies and/or pharmaceutical compositions by co-administering multifunctional dendrimers of this invention. In co-administration procedures, the agents may be administered concurrently or sequentially. In some embodiments, the multifunctional dendrimers described herein are administered prior to the other active agent(s). The agent or agents to be co-administered depends on the type of condition being treated. For example, when the condition being treated is arthritis, the additional agent can be an agent effective in treating arthritis (e.g., TNF-α inhibitors such as anti-TNF α monoclonal antibodies (such as REMICADE®, CDP-870 and HUMIRATM (adalimumab) and TNF receptor-immunoglobulin fusion molecules (such as ENBREL®)(entanercept), IL-1 inhibitors, receptor antagonists or soluble IL-1R α (e.g. KINERET™ or ICE inhibitors), nonsteroidal anti-inflammatory agents (NSAIDS), piroxicam, diclofenac, naproxen, flurbiprofen, fenoprofen, ketoprofen ibuprofen, fenamates, mefenamic acid, indomethacin, sulindac, apazone, pyrazolones, phenylbutazone, aspirin, COX-2 inhibitors (such as CELEBREX® (celecoxib), VIOXX® (rofecoxib), BEXTRA® (valdecoxib) and etoricoxib, (preferably MMP-13 selective inhibitors), NEUROTIN®, pregabalin, sulfasalazine, low dose methotrexate, leflunomide, hydroxychloroquine, d-penicillamine, auranofin or parenteral or oral gold). The additional agents to be co-administered can be any of the well-known agents in the art, including, but not limited to, those that are currently in clinical use. The determination of appropriate type and dosage of radiation treatment is also within the skill in the art or can be determined with relative ease.

Where clinical applications are contemplated, in some embodiments of the present invention, the dendrimer conjugates are prepared as part of a pharmaceutical composition in a form appropriate for the intended application. Generally, this entails preparing compositions that are essentially free of pyrogens, as well as other impurities that could be harmful to humans or animals. However, in some embodiments of the present invention, a straight dendrimer formulation may be administered using one or more of the routes described herein.

In preferred embodiments, the dendrimer conjugates are used in conjunction with appropriate salts and buffers to render delivery of the compositions in a stable manner to allow for uptake by target cells. Buffers also are employed when the dendrimer conjugates are introduced into a patient. Aqueous compositions comprise an effective amount of the dendrimer conjugates to cells dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. Except insofar as any conventional media or agent is incompatible with vectors, cells, or tissues, its use in therapeutic compositions is contemplated. Supplementary active ingredients may also be incorporated into the compositions.

In some embodiments of the present invention, the active compositions include classic pharmaceutical preparations. Administration of these compositions according to the present invention is via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection.

The active dendrimer conjugates may also be administered parenterally or intraperitoneally or intratumorally. Solutions of the active compounds as free base or pharmacologically acceptable salts are prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

In some embodiments, a therapeutic agent is released from dendrimer conjugates within a target cell (e.g., within an endosome). This type of intracellular release (e.g., endosomal disruption of a linker-therapeutic conjugate) is contemplated to provide additional specificity for the compositions and methods of the present invention. The present invention provides dendrimers with multiple (e.g., 100-150) reactive sites for the conjugation of linkers and/or functional groups comprising, but not limited to, therapeutic agents, targeting agents, imaging agents and biological monitoring agents.

The compositions and methods of the present invention are contemplated to be equally effective whether or not the dendrimer conjugates of the present invention comprise a fluorescein (e.g. FITC) imaging agent. Thus, each functional group present in a dendrimer composition is able to work independently of the other functional groups. Thus, the present invention provides dendrimer conjugates that can comprise multiple combinations of targeting, therapeutic, imaging, and biological monitoring functional groups.

The present invention also provides a very effective and specific method of delivering molecules (e.g., therapeutic and imaging functional groups) to the interior of target cells (e.g., cancer cells). Thus, in some embodiments, the present invention provides methods of therapy that comprise or require delivery of molecules into a cell in order to function (e.g., delivery of genetic material such as siRNAs).

The pharmaceutical forms suitable for injectable use include sterile aqueous solutions or dispersions and sterile powders for the extemporaneous preparation of sterile injectable solutions or dispersions. The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it may be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Upon formulation, dendrimer conjugates are administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution is suitably buffered, if necessary, and the liquid diluent first rendered isotonic with sufficient saline or glucose. These particular aqueous solutions are especially suitable for intravenous, intramuscular, subcutaneous and intraperitoneal administration. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). In some embodiments of the present invention, the active particles or agents are formulated within a therapeutic mixture to comprise about 0.0001 to 1.0 milligrams, or about 0.001 to 0.1 milligrams, or about 0.1 to 1.0 or even about 10 milligrams per dose or so. Multiple doses may be administered.

Additional formulations that are suitable for other modes of administration include vaginal suppositories and pessaries. A rectal pessary or suppository may also be used. Suppositories are solid dosage forms of various weights and shapes, usually medicated, for insertion into the rectum, vagina or the urethra. After insertion, suppositories soften, melt or dissolve in the cavity fluids. In general, for suppositories, traditional binders and carriers may include, for example, polyalkylene glycols or triglycerides; such suppositories may be formed from mixtures containing the active ingredient in the range of 0.5% to 10%, preferably 1%-2%. Vaginal suppositories or pessaries are usually globular or oviform and weighing about 5 g each. Vaginal medications are available in a variety of physical forms, e.g., creams, gels or liquids, which depart from the classical concept of suppositories. In addition, suppositories may be used in connection with colon cancer. The dendrimer conjugates also may be formulated as inhalants for the treatment of lung cancer and such like.

EXAMPLES

The following examples are provided in order to demonstrate and further illustrate certain preferred embodiments and aspects of the present invention and are not to be construed as limiting the scope thereof.

Example 1

Previous experiments involving dendrimer related technologies are located in U.S. Pat. Nos. 6,471,968, 7,078,461, and U.S. patent application Ser. Nos. 09/940,243, 10/431,682, 11,503,742, 11,661,465, 11/523,509, 12/403,179, 12/106,876, 11/827,637, and 61/101,461; and U.S. Provisional Patent Application Ser. Nos. 61/256,759, 61/140,840, 61/091,608, 61/097,780, 61/101,461, 61/237,172, 61/229, 168, 61/221,596, and 61/251,244; each herein incorporated by reference in their entireties.

Example 2

SYNTHESIS OF G(5) PAMAM dendrimer

Scheme 1

Step 1: Synthesis of G(-0.5) PAMAM Dendrimer

Ethylene diamine (5 g) in methanol (20 ml) was added dropwise to a stirred solution of methyl acrylate (35 g) in methanol (20 ml) at 0° C. under nitrogen over 2 hours. The mixture was stirred for 30 min at 0° C. and then allowed to warm to room temperature (~25° C.) and stirred for a further 24-48 hours. The solvent was removed under reduced pressure at 40° C. using a rotary evaporator and the resulting colorless oil dried under vacuum overnight to give G(-0.5).

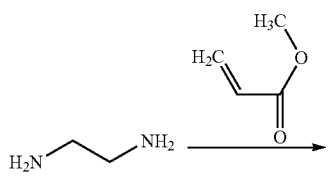

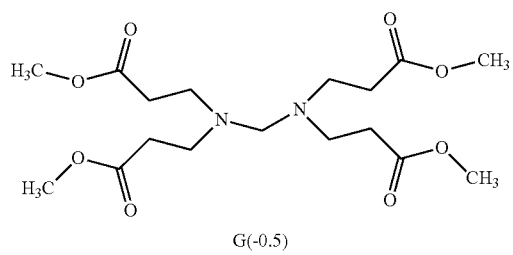

G(-0.5)

Step 2: Synthesis of G(0) PAMAM Dendrimer

A solution of G(-0.5) was reacted with an excess of ethylene diamine in MeOH at 0° C. The rate of addition was such that temperature rise was kept to a minimum. The reaction was continued until no ester groups were detectable by NMR. The solvent was removed under reduced pressure maintaining the temperature below 40° C. Excess EDA was removed using an azeotropic mixture of toluene and methanol (9:1). The remaining toluene was removed by azeotropic distillation using MeOH. Removal of the remaining MeOH under vacuum (10-1 mm) gave G(0).

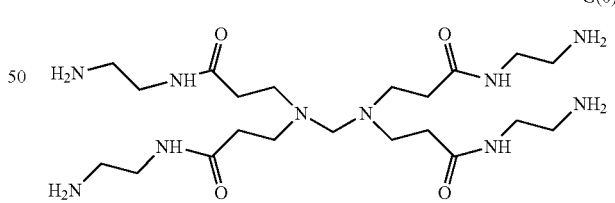

G(0)

Step 3: Synthesis of G(0.5) PAMAM Dendrimer

A solution of G(0) in MeOH was reacted with excess methyl acrylate in MeOH under Michael addition conditions to form an adduct having terminal methyl ester moities. The solvent was removed under pressure at 40° C. using a rotary evaporator and the resulting colorless oil dried under vacuum overnight to give G(0.5).

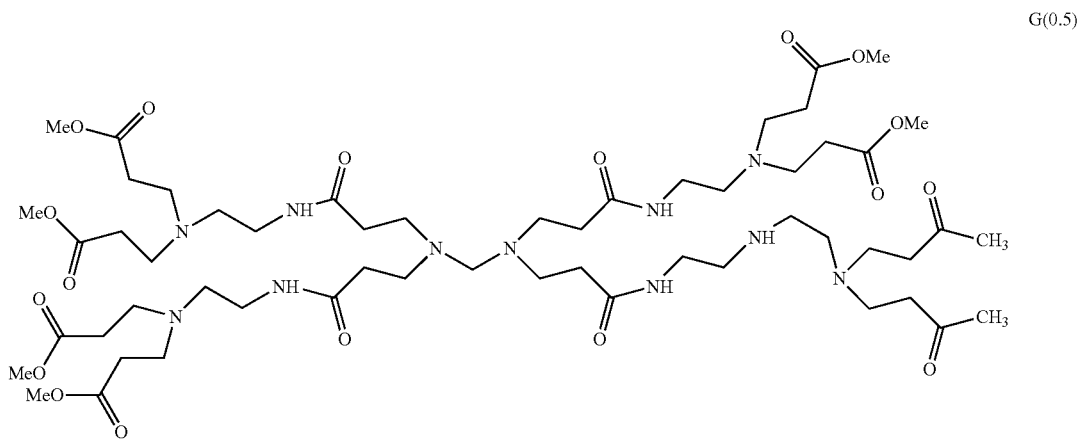 [SMILES: COC(=O)CCN(CCNC(=O)CCN(CCC(=O)NCCNCCN(CCC(C)=O)CCC(C)=O)CN(CCC(=O)NCCN(CCC(=O)OC)CCC(=O)OC)CCC(=O)NCCN(CCC(=O)OC)CCC(=O)OC)CCC(=O)OC]

G(0.5)

Step 4: Synthesis of G(1) PAMAM Dendrimer

A solution of G(0.5) was reacted with an excess of ethylene diamine in MeOH at 0° C. The rate of addition was such that temperature rise was kept to a minimum. The reaction was continued until no ester groups were detectable by NMR. The solvent was removed under reduced pressure maintaining the temperature below 40° C. Excess EDA was removed using an azeotropic mixture of toluene and methanol (9:1). The remaining toluene was removed by azeotropic distillation using MeOH. Removal of the remaining MeOH under vacuum (10-1 mm) gave G(1).

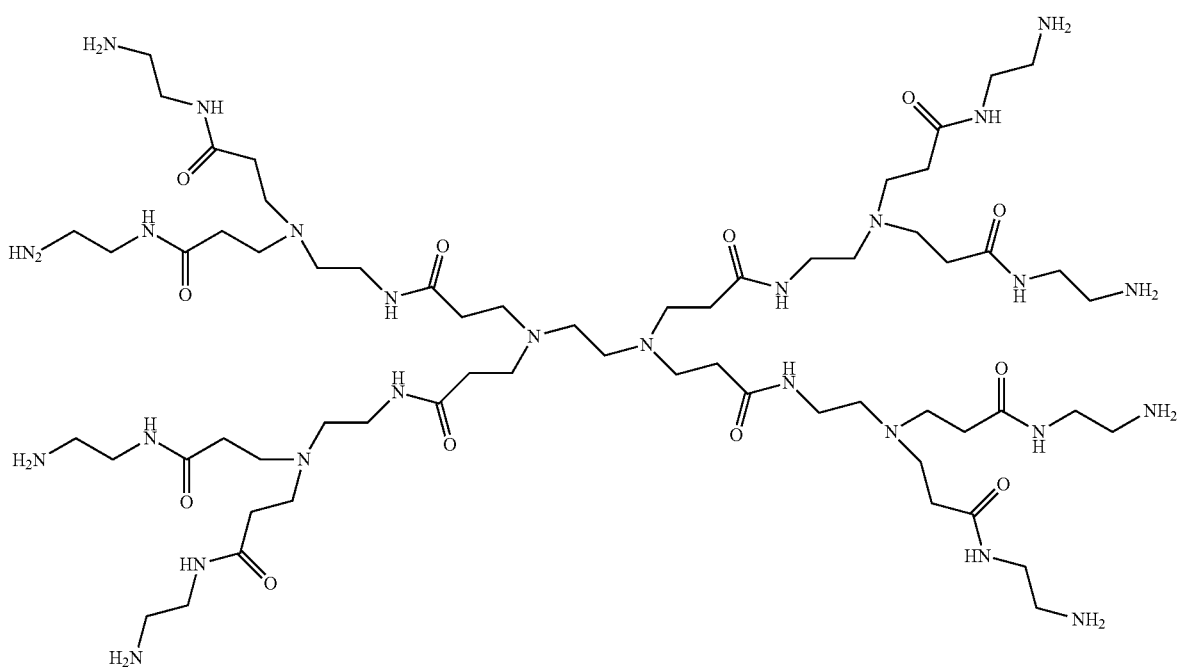

G(1)

Steps 5-12

The alternating reactions with methyl acrylate and ethylene diamine were repeated based on the steps above to give G(5).

Scheme 2

Step 1: Acetylation of the G(5) PAMAM Dendrimer

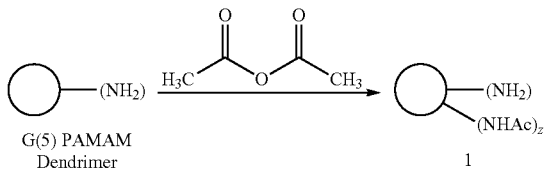

G(5) PAMAM dendrimer was dissolved in methanol and treated with sufficient acetic anhydride to acetylate between 60 and 80% of the primary amines on the surface of the dendrimer. After the reaction was complete, the resulting compound 1 was treated with a basic anion exchange resin to remove the acetic acid by-product of the reaction. After removing the resin by filtration, the reaction mixture was stripped to dryness.

This material was analyzed by 1H NMR to determine the number of acetyl groups by integrations. A small sample of this material was treated with excess propionic anhydride, and the product of this reaction analyzed by 1H NMR. Integration of the acetyl methyl group and propionyl methyl group confirmed the ratio of acetylated primary amines and free amines (which are propionylated for the NMR experiment).

Step 2: Conjugation of Folic Acid and glycidolation

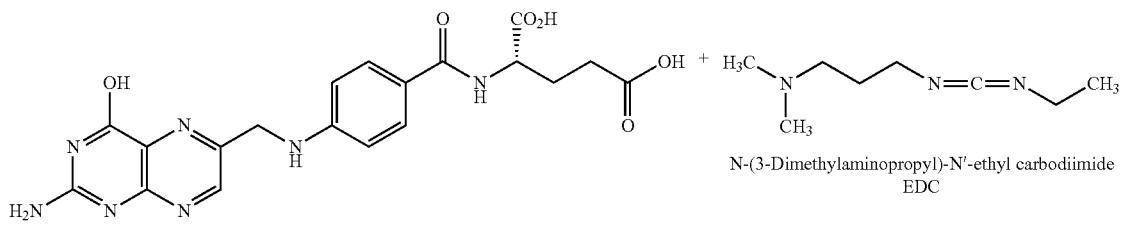

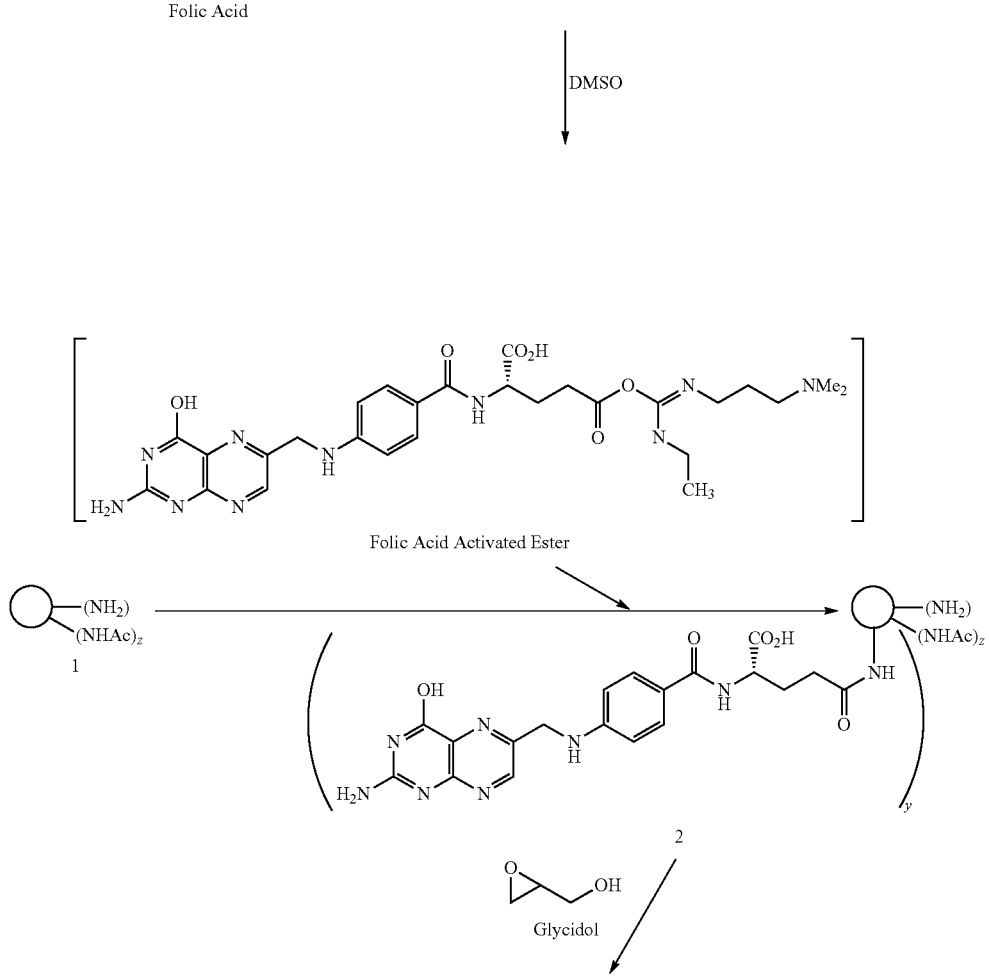

-continued

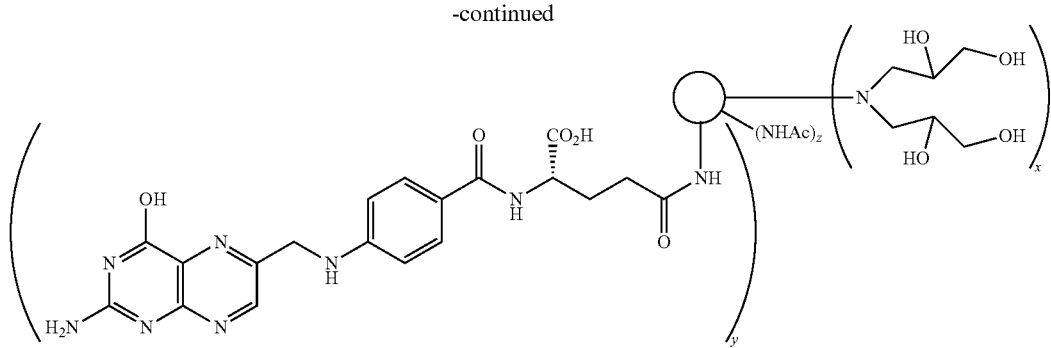

3

Folic acid (FA) was dissolved in DMSO and treated with a slight excess of the coupling agent EDC. This DMSO solution of the folic acid activated ester was slowly added to an aqueous solution of (1) dissolved in deionized water to yield compound 2. After the FA conjugation reaction was complete, glycidol was added to the reaction mixture and stirred until the glycidolation complete. The reaction mixture was filtered, concentrated and lyopholized to a powder to yield compound 3 wherein z is a number from 65 to 108, y is a number from 3 to 8, and x is a number from 10 to 20.

This material was analyzed by HPLC for free folic acid, 1H NMR for ID, and UV-Vis to determine the average number of folic acids conjugated on the dendrimer surface.

Step 3: Conjugation of Methotrexate to the Dendrimer

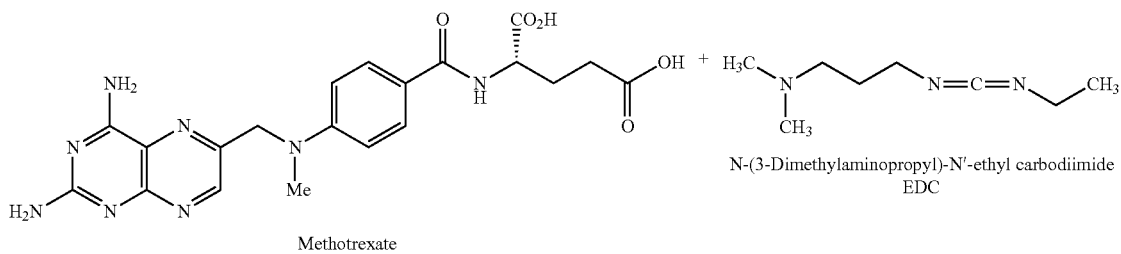

N-(3-Dimethylaminopropyl)-N'-ethyl carbodiimide
EDC

Methotrexate

↓ DMSO

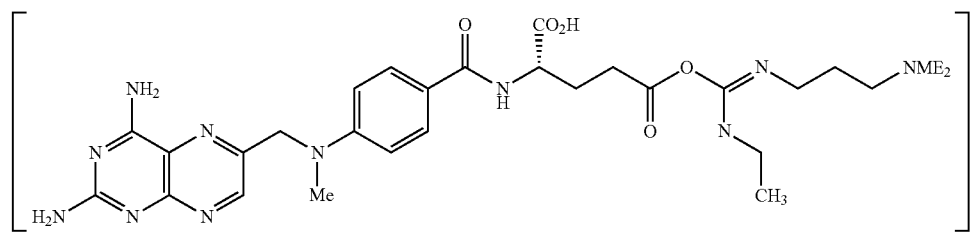

Methotrexate Activated Ester

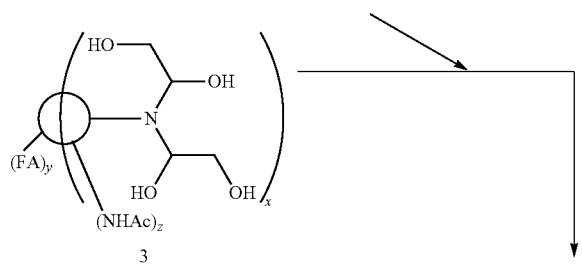

3

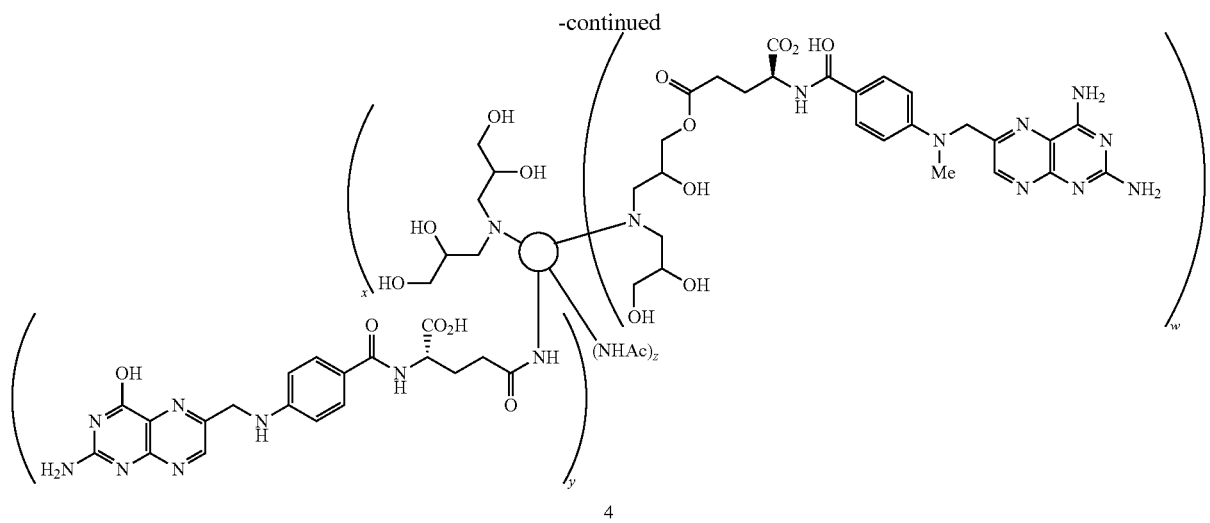

4

Methotrexate (22.5 g, 0.050 moles) was dissolved in DMSO (600 mL) and treated with EDC (9.0 g, 0.047 moles) and stirred until the activation complete. This activated ester of methotrexate was slowly added to a solution of 3 (150 g, 0.00416 moles) in DMSO (2500 mL). After stirring for about 2 hours, the reaction was diluted with water (38 L) and concentrated using tangential flow filtration equipped with 10 kD cellulose membrane filters. The retentate was treated with phosphate buffer, and purified using tangential flow filtration (TFF) to remove any low molecular weight impurities. The retentate was lyophylized to yield compound 4 wherein z is a number from 65 to 108, y is a number from 3 to 8, and x is a number from 10 to 20, w is a number from 7 to 12. Compound 4 is referred to herein as ATI-101.

Example 3

The efficacy of ATI-101 was evaluated using the rat collagen arthritis model in a series of experiments described below. Rat collagen induced arthritis is an experimental model of polyarthritis that has been widely used for preclinical testing of numerous anti-arthritic agents. Rat type II collagen arthritis results when rats are immunized against homologous or heterologous type II collagen. The resulting arthritis was characterized by reliable onset and progression of robust, easily measurable, polyarticular inflammation, marked cartilage destruction in association with pannus formation and mild to moderate bone resorption and periosteal bone proliferation. For all examples below statistical analysis of body/paw weights, paw AUC parameters and histopathologic parameters were evaluated using a Student's t-test with significance set at the 5% significance level. As used herein "significant" means that $p \leq 0.05$. Unless specified as "normal control" or "disease control" reference to "animal" means a rat with developing type II collagen arthritis.

Percent inhibition of paw weight and AUC is calculated using the following formula:

% Inhibition=$(A-B/A \times 100)$; $A$=(Mean Disease Control−Mean Normal); $B$=(Mean Treated−Mean Normal).

Bovine Type II collagen (Sigma) was diluted with 0.1N acetic acid to a concentration of 4 mg/ml. and emulsified with an equal volume of Freund's incomplete adjuvant (Sigma). Female Lewis rats (Charles River) were randomized by weigh into 5 study groups as shown in Table 1.

TABLE 1

| Treatment groups | | Arthritis + Prophylactic |
| --- | --- | --- |
| Group | n | IV, Treatment, M, W, F Day 0-16, 2 ml/kg |
| 1 | 4 | Normal controls + saline vehicle |
| 2 | 10 | Arthritis + saline vehicle |
| 3 | 10 | Arthritis + Batch 1 70 mg/kg of ATI-101 |
| 4 | 10 | Arthritis + Batch 2 70 mg/kg of ATI-101 |
| 5 | 10 | Arthritis + methotrexate 0.2 mg/kg |

Batch 1 and Batch 2 represent ATI-101 generated from two manufacturing campaigns in which two different batches of dendrimer starting material were employed and where ATI-101 from the two batches was released to a common set of specifications.

The rats were anesthetized and given collagen injections spread over 3 subcutaneous sites on back on day 0 and day 6. Animals were dosed intravenously 3 times weekly (3×/week) on Monday, Wednesday, and Friday (dose days 0, 2, 4, 7, 9, 11, 14, 16) with Vehicle (saline), 70 mg/kg Batch 1, 70 mg/kg Batch 2, or 0.2 mg/kg Methotrexate (MTX). Animals were euthanized on study day 17. Efficacy evaluation was based on ankle caliper measurements, area under the curve (AUC), terminal hind paw weights, and histopathologic evaluation of ankles and knees. All animals survived to study termination.

Histologic assessment of knee and ankle joints is performed by assigning scores from 0 to 5 for multiple characteristics noted microscopically based on pre-determined criteria by a board-certified veterinary pathologist. For example, a score of 0 for inflammation, pannus, cartilage damage and bone resorption would reflect scores for a healthy normal joint devoid cartilage or bone destruction and devoid of inflammation. Conversely, a score of 5 for inflammation reflects the presence of severe infiltrates of inflammatory cells (neutrophils, lymphocytes, and/or macrophages) usually in conjunction with severe edema. A pannus score of 5 reflects severe infiltration of the cartilage surface with altered proteinic material which covers more than 75% of the joint surface. A cartilage damage score of 5 is associated with diffuse loss of toluidine blue (cartilage matrix) staining with severe loss of chondrocytes (cartilage cells) and/or collagen involving the full thickness of cartilage. A bone resorption score of 5 would be ascribed to a section with severe loss of cortical bone and distortion of the remaining cortical surface. This is typically associated with loss of medullary bone (bony spicules in deep bone regions), presence of numerous osteoclasts (cells associated with bone matrix digestion) and severe distortion of overall architecture. Most tissue sections will have scores between the extremes above. Criteria-based semi-quantitative scoring is a well-accepted technique allowing for precise, reproducible, highly descriptive scoring of the degree of pathologic change in knee and ankle joints in this model.

FIG. 1 shows the ankle diameter measurement over the 17 days of the study. Significant inhibition of ankle diameter was seen in rats treated with Batch 1(significant days 10-17), Batch 2 (d10-17), or MTX (d10-17), as compared to disease controls. (p<0.05 to disease control animals).

Figure 2:
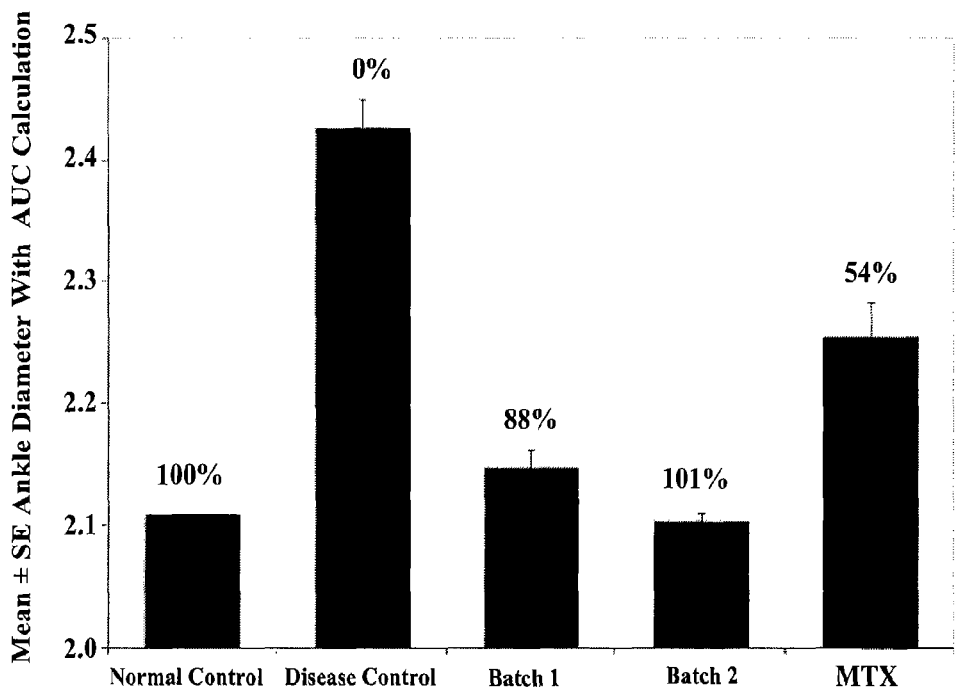
FIG. 2 depicts the inhibition of ankle diameter in arthritic rats treated with ATI-101 Batch 1, Batch 2 or MTX as compared to disease controls expressed as AUC.

These data are also reflected in FIG. 2 which shows the area under the curve (AUC) based on the graph shown in FIG. 1. Significant inhibition of ankle diameter AUC was seen in rats treated with Batch 1 (88% inhibition), Batch (101%), or MTX (54%), as compared to disease controls. The data shown in these graphs reflects the significant inhibition of ankle diameter as compared to animals in which arthritis was induced by collagen administration and were treated with the vehicle used for administration of drug (disease controls). (*p≤0.05 to disease control animals).

Figure 3:
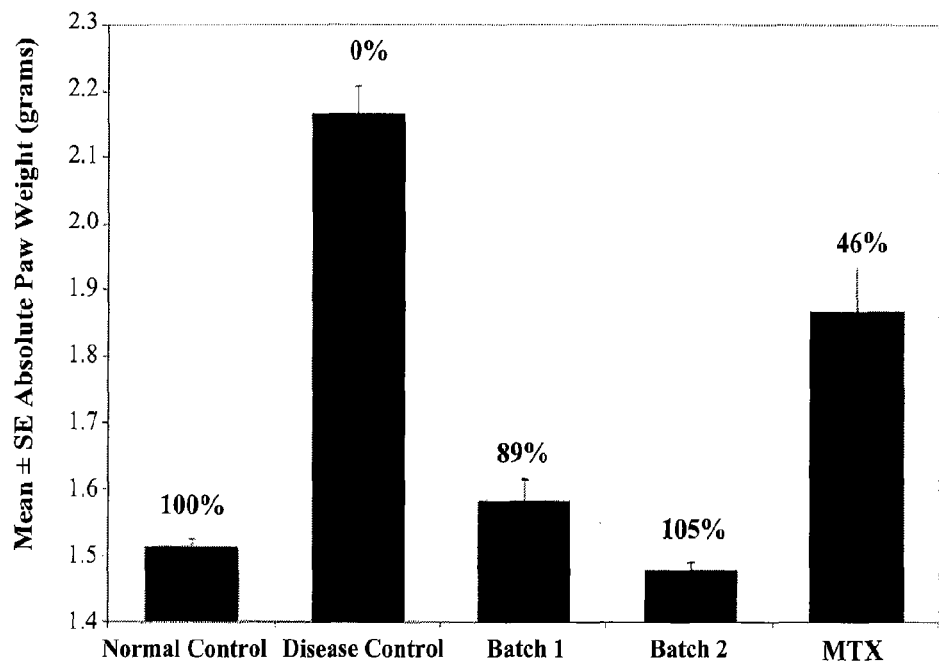
FIG. 3 depicts final paw weights following treatment with Batch 1, Batch 2, or MTX as compared to disease controls.

As depicted in FIG. 3, final paw weights were significantly inhibited by treatment with Batch 1 (89% inhibition), Batch 2 (105%), or MTX (46%), as compared to disease controls. The treatment is shown on the x-axis and the paw weight (grams) on the y-axis. The efficacy of the two different batches was comparable. (*p≤0.05 to disease control animals).

Preserved and decalcified (5% formic acid) ankle and knee joints were cut in half longitudinally (ankles) or in the frontal plane (knees), processed through graded alcohols and a clearing agent, infiltrated and embedded in paraffin, sectioned, and stained with Toluidine Blue.

All vehicle treated disease control rats had marked to severe synovitis and periarticular inflammation in at least one and usually both, ankle joints with no to moderate pannus and bone resorption and no to marked cartilage damage. In contrast, all ankle histopathology parameters were reduced in treated animals with Batch 1 and Batch 2 showing significantly greater reduction in ankle and knee histopathology when compared with MTX. (*p≤0.05 to disease control animals).

Figure 4:
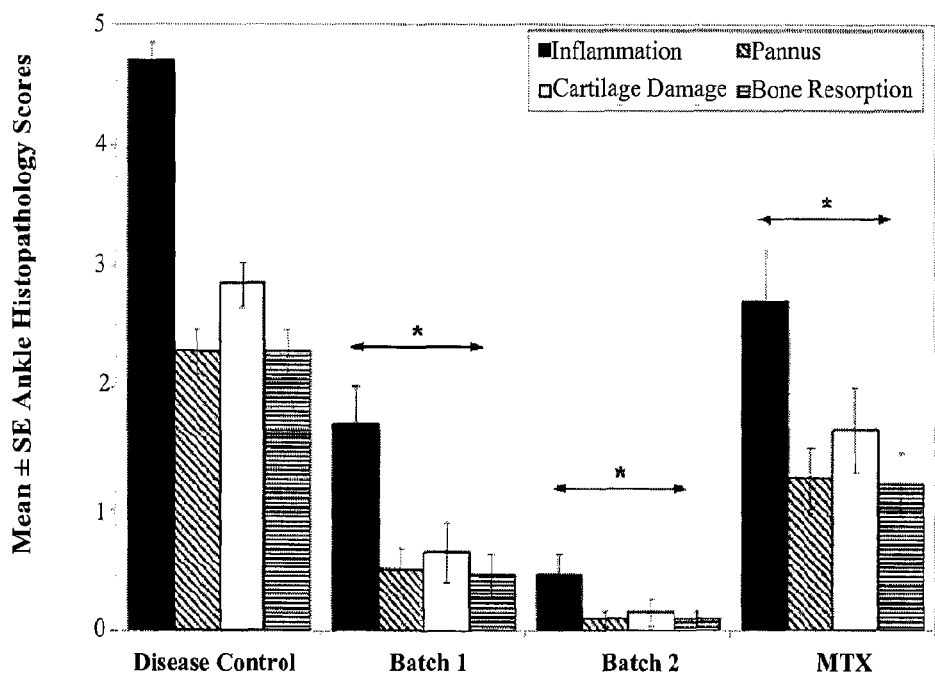
FIGS. 4A and B depict the results for these parameter based on ankle histopathology scores of the ankle and knee respectively from arthritic rats treated with control vehicle, Batch 1, Batch 2 or MTX.
Figure 4:
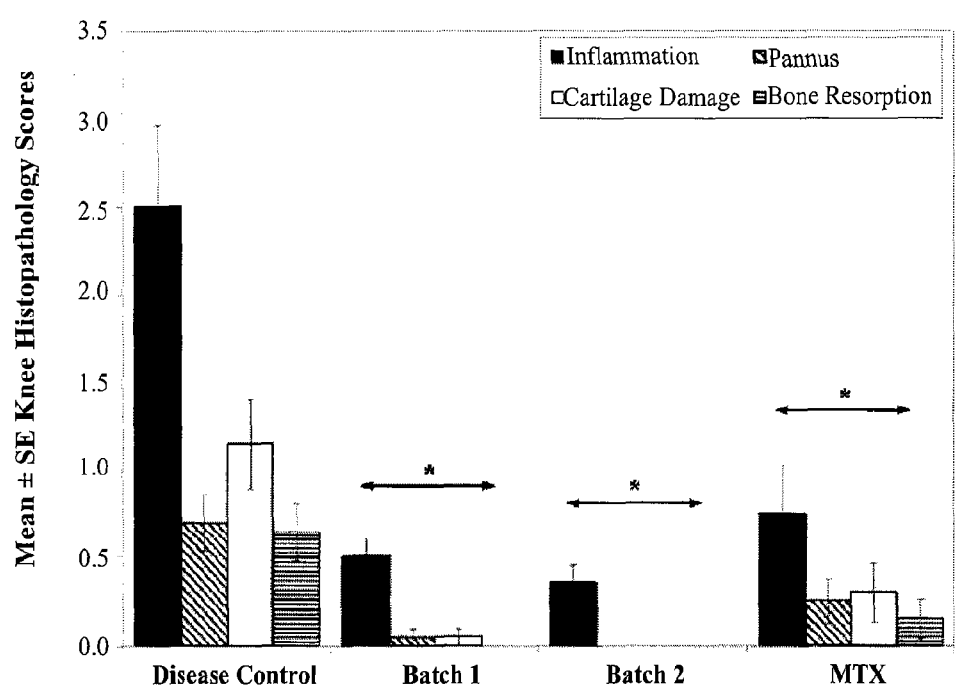

FIGS. 4A and 4B reflect the clinical outcomes with respect to inflammation, pannus, cartilage damage and bone resorption. FIG. 4A shows the results for these parameters based on ankle histopathology scores of the ankle.

FIG. 4B shows the results for these parameters based on knee histopathology scores of the knee.

Figure 5:
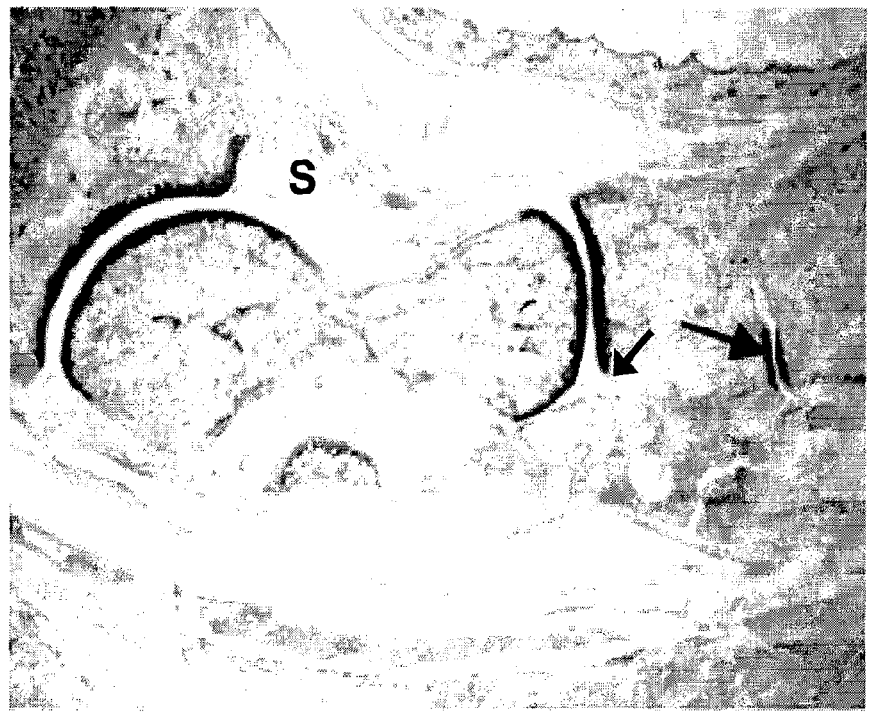
FIGS. 5A-E are photomicrographs of ankle cross sections from arthritic rats treated with control vehicle, Batch 1, Batch 2 or MTX.
Figure 5:
Figure 5:
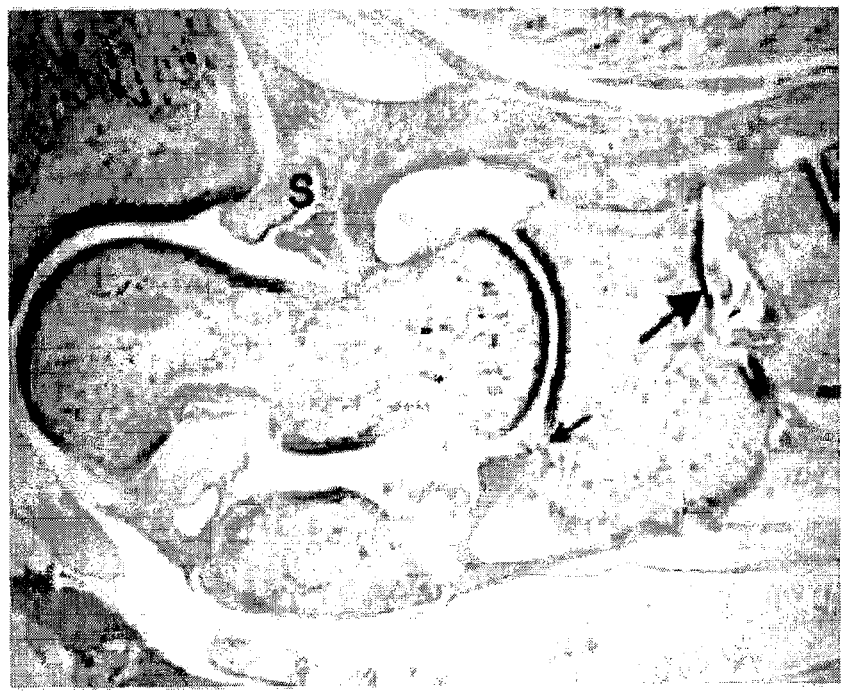
Figure 5:
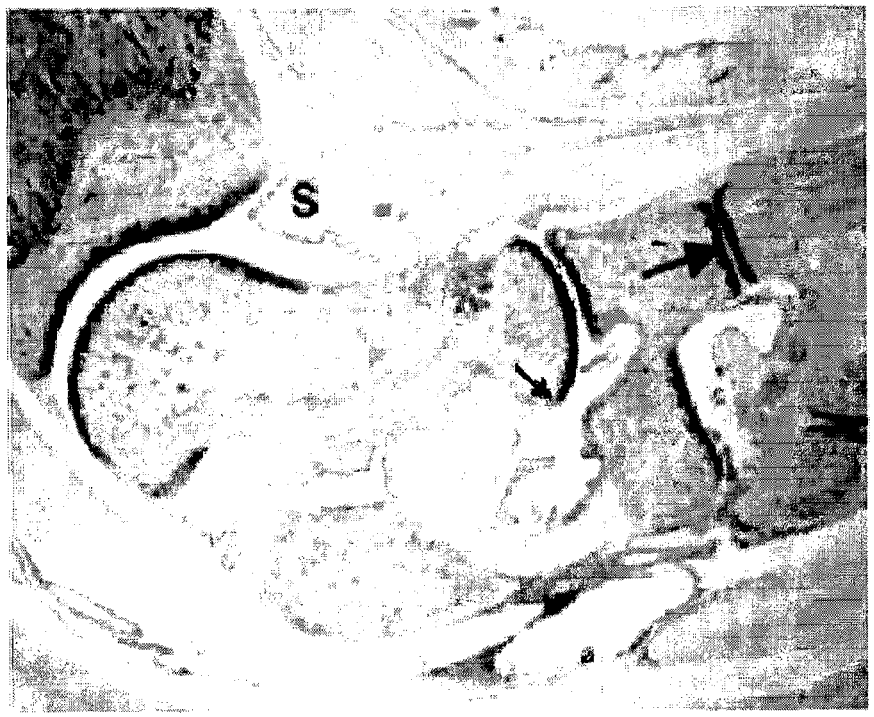
Figure 5:

FIGS. 5A-E show photomicrographs of ankle cross sections that are representative of the group. FIG. 5A shows the ankle of a normal rat treated with vehicle and shows normal synovium (S) and normal cartilage (large arrow) with no pannus or bone destruction (small arrow). FIG. 5B shows the ankle of an arthritic rat treated with vehicle showing severe synovitis, i.e. severely thickened synovial lining containing dense populations of inflammatory cells (S) and moderate cartilage damage (large arrow) with mild pannus and bone destruction (small arrow). FIG. 5C shows the ankle of an arthritic rat treated with 70 mg/kg batch 1 with minimal synovitis (S) based on ruffling of the lining surface and no cartilage damage (large arrow) with no pannus or bone destruction (small arrow). FIG. 5D shows the ankle of an arthritic rat treated with 70 mg/kg batch 2 with minimal synovitis (S) and no cartilage damage (large arrow) with no pannus or bone destruction (small arrow). FIG. 5E shows the ankle of an arthritic rat treated with 0.2 mg/kg methotrexate with moderate synovitis (S) based on moderate synovial thickening with inflammatory cells and minimal cartilage damage (large arrow) with minimal pannus and bone destruction (small arrow).

Figure 6:
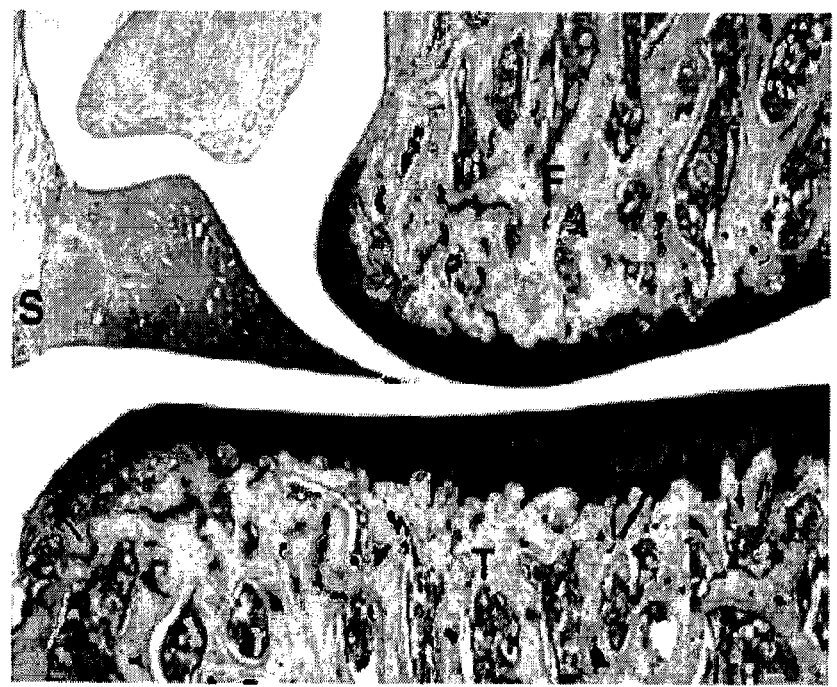
FIGS. 6A-D are photomicrographs of knee cross sections from arthritic rats treated with control vehicle, Batch 1, Batch 2 or MTX.
Figure 6:
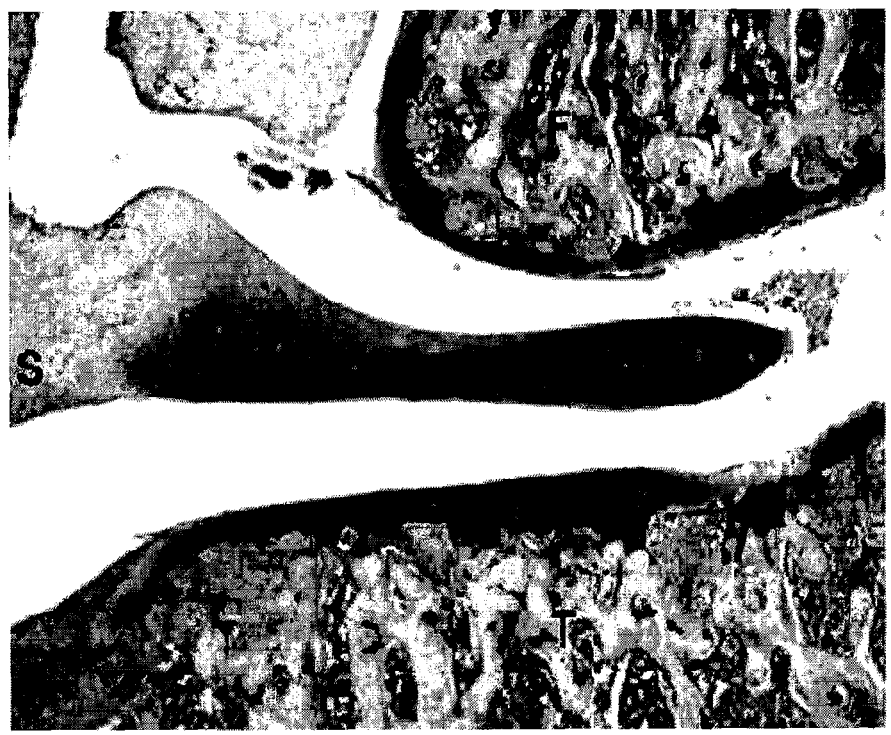
Figure 6:
Figure 6:
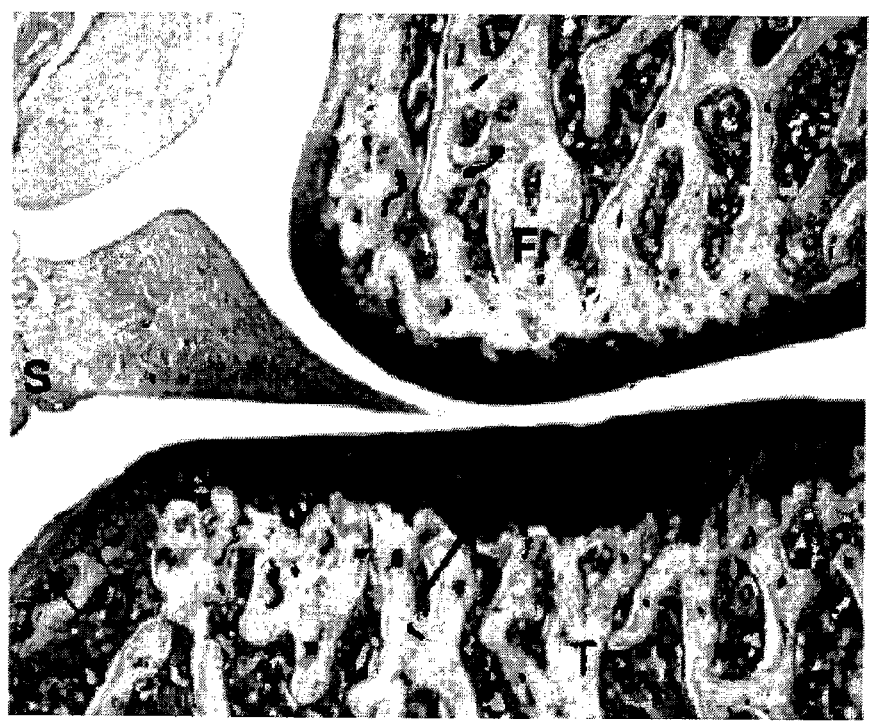

FIGS. 6A-D show photomicrographs of knee cross section that have high scores for the group. The femur is identified with "F" and the tibia with "T". FIG. 6A shows the knee from a normal rat treated with vehicle showing no synovitis (S), cartilage damage (large arrow), pannus, or bone resorption (small arrow). FIG. 6B shows the knee from an arthritic rat treated with vehicle showing severe synovitis (S), marked cartilage damage (large arrow) and moderate pannus and bone resorption, i.e. collapse of the surface due to loss of bony matrix. (small arrow) FIG. 6C shows the knee from an arthritic rat treated with 70 mg/kg Batch 1 showing minimal synovitis (S), minimal cartilage damage (large arrow), minimal pannus and no resorption (small arrow). FIG. 6D shows a knee from an arthritic rat treated with 70 mg/kg Batch 2 showing no synovitis (S), cartilage damage (large arrow), pannus or resorption (small arrow).

Example 4

The study described below was done to determine the dose responsive efficacy and toxicity of ATI-101 administered intravenously (IV) or subcutaneously (SC) or the efficacy of methotrexate administered intravenously twice weekly for inhibition of inflammation that occurs in developing type II collagen arthritis in rats.

Bovine Type II collagen (Sigma) was diluted with 0.1N acetic acid to a concentration of 4 mg/ml. and emulsified with an equal volume of Freund's incomplete adjuvant (Sigma). Female Lewis rats (Charles River) were randomized by weigh into study groups as shown in Table 2. Animals in satellite groups 5s and 12s were included for PK sampling and analysis.

TABLE 2

| Treatment groups | | Arthritis + Prophylactic |
|---|---|---|
| Group | N | IV, Treatment, 2X/week Day 0-16, 5 ml/kg except group 8 which is 6 ml/kg |
| 1 | 4 | Normal controls + saline vehicle, IV |
| 2 | 10 | Arthritis + saline vehicle, IV |
| 3 | 10 | Arthritis + 160 mg/kg ATI-101, IV |
| 4 | 10 | Arthritis + 100 mg/kg ATI-101, IV |
| 5 | 10 | Arthritis + 65 mg/kg ATI-101, IV |
| 5s | 6 | Arthritis + 65 mg/kg ATI-101, IV |
| 6 | 10 | Arthritis + 20 mg/kg ATI-101, IV |
| 7 | 10 | Arthritis + 5 mg/kg ATI-101, IV |
| 8 | 10 | Arthritis + .75 mg/kg MTX, IV |
| 9 | 10 | Arthritis + .5 mg/kg MTX, IV |
| 10 | 10 | Arthritis + .25 mg/kg MTX, IV |
| 11 | 10 | Arthritis + saline vehicle, SC |
| 12 | 10 | Arthritis + 65 mg/kg ATI-101, SC |
| 12s | 6 | Arthritis + 65 mg/kg ATI-101, SC |

The rats were anesthetized and given collagen injections spread over 3 subcutaneous sites on back on day 0 and day 6. Animals were treated intravenously (IV), 2 times weekly (2x/week) on Monday and Thursday (dose days 0, 3, 7, 10, 14, 17) with vehicle (saline), ATI-101 (5, 20, 65, 100 or 160 m/kg) or Methotrexate (MTX)(0.25, 0.5, or 0.75 mg/kg), or subcutaneously (SC) with vehicle or ATI-101 (65 mg/kg).

Rats were weighed on days 0, 3, 6, and 9-18 of the study, and caliper measurements of ankles were taken every day beginning on day 9 (or day 0 of arthritis). After final body weight measurement on day 18, animals were euthanized, blood was drawn for serum (for clinical chemistries) and CBC analysis and tissues were collected. No clinical chemistry or CBC analysis was done for groups 5s and 12s, however these groups were sampled for drug levels for pharmacokinetic analysis. All animals survived to study termination.

Figure 7:
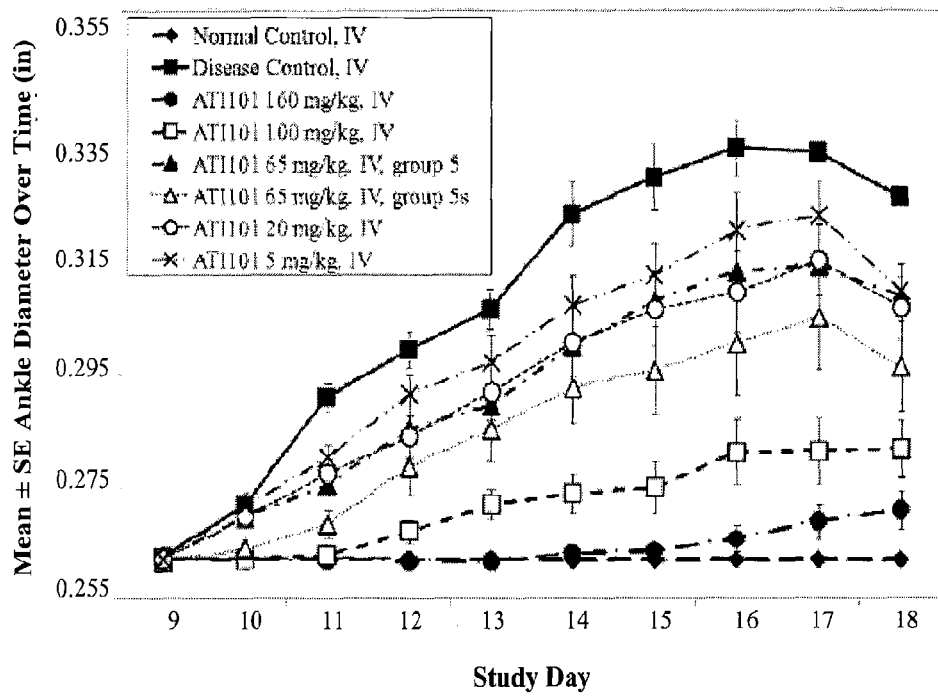
FIG. 7 depicts the dose response over an ATI-101 range from 5 mg/kg through 160 mg/kg.

As shown in FIG. 7, the ankle diameters showed a dose response over the ATI-101 range from 5 mg/kg through 160 mg/kg twice weekly IV dosing with a minimally effective dose shown at 5 mg/kg and almost complete suppression of the arthritic response at 160 mg/kg.

Pharmacokinetics

Figure 8:
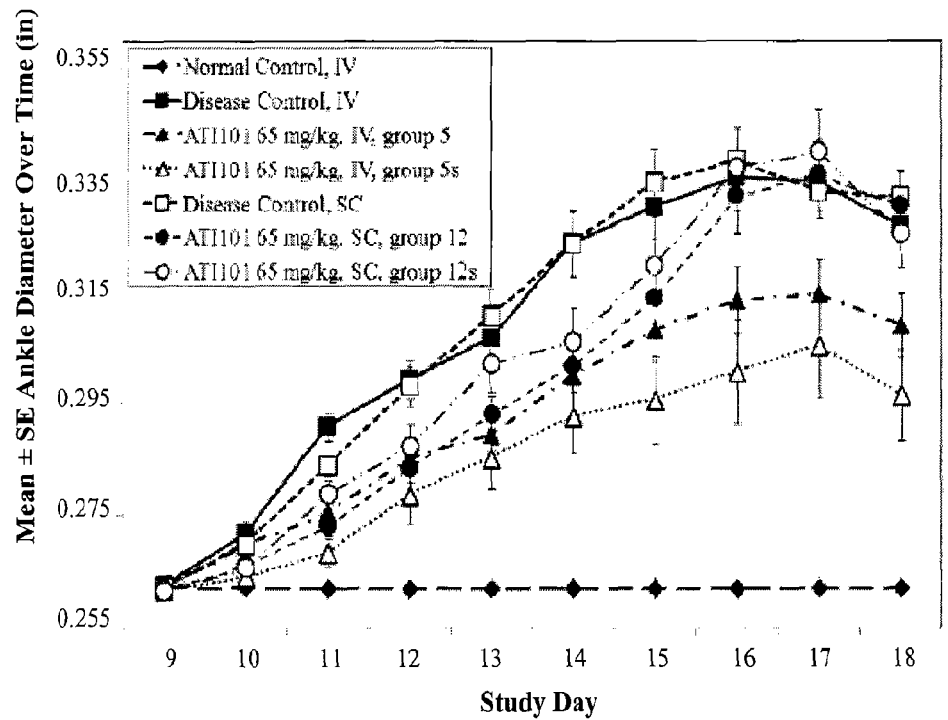
FIG. 8 shows the relative efficacy as measured by ankle diameter in the IV and SC groups.

Samples were taken from the 65 mg/kg IV (group 5s) and 65 mg/kg SC (group 12s) dose groups to determine the pharmacokinetics of ATI-101. The results showed that bioavailability as measured by AUC was about 47% less in the SC groups when compared with the IV dosed groups. This is reflected by the lower efficacy as measured by ankle diameter and paw weight in the corresponding SC-dosed animals. FIG. 8 shows the relative efficacy as measured by ankle diameter in the IV and SC groups.

Drug Levels in Synovial Fluid

Synovial fluid was removed from the knee joints of animals in the 100 mg/kg dose group. The fluid from 2 knees per rat was pooled and analyzed for ATI-101. ATI-101 was able to cross into the synovial capsule as shown by the presence of ATI-101 in the synovial fluid of the treated animals. Drug levels were detected in 9 of 10 animals and were found in concentrations of approximately 0.005 mg/ml.

Therapeutic Index

Complete Blood Counts (CBC) and Clinical Chemistries were evaluated for each group. Over the 18 day duration of the study, the bone marrow was clearly suppressed in rats given the 0.75 mg/kg MTX as indicated by decreased WBC (2 of 10 animals were below the normal range) and neutrophil counts (7 of 10 below the normal range) vs. normal rats. Using the average ED50 value for efficacy (AUC+Final Paw Weight) of 0.25 mg/kg and the 0.75 mg/kg value for life threatening toxicity (bone marrow suppression) results in a therapeutic index of less than 3 for methotrexate. Because evidence of bone marrow suppression was present in rats given 0.5 mg/kg (decreased neutrophil counts), the therapeutic index for MTX may be less than 2. In addition, there was evidence that the high dose preparation of MTX (0.75 mg/kg dose) did not remain completely in solution which may have led an underestimation of the toxicity and possibly reduced efficacy. In contrast, there was no evidence of bone marrow suppression in the ATI groups, and the ATI average ED50 value was 47 mg/kg. No clinically relevant toxicity was seen at 160 mg/kg thus resulting in an approximate therapeutic index of 3.4 or greater.

Example 5

Bovine Type II collagen (Sigma) was diluted with 0.1N acetic acid to a concentration of 4 mg/ml. and emulsified with an equal volume of Freund's incomplete adjuvant (Sigma). Female Lewis rats (Charles River) were randomized by weigh into 10 study groups Table 3 identifies the groups that were used for evaluation of efficacy and Table 4 identifies the groups used for evaluation of toxicity.

TABLE 3

| Treatment groups | | Arthritis + Prophylactic |
|---|---|---|
| Group | N | IV, Treatment, 2X/week Day 0-21, 5 ml/kg Etanercept SC 1 ml/kg, days 9, 12, 15 |
| 1 | 4 | Normal controls + saline vehicle, IV |
| 2 | 10 | Arthritis + saline vehicle, IV |
| 3 | 10 | Arthritis + 65 mg/kg ATI-101, IV |
| 4 | 10 | Arthritis + 20 mg/kg ATI-101, IV |
| 5 | 10 | Arthritis + 5 mg/kg ATI-101, IV |
| 6 | 6 | Arthritis + Saline IV, Etanercept 1 mg/kg SC |
| 7 | 10 | Arthritis + 65 mg/kg ATI-101, IV + Etanercept 1 mg/kg |
| 8 | 10 | Arthritis + 20 mg/kg ATI-101, IV + Etanercept 1 mg/kg |
| 9 | 10 | Arthritis + 5 mg/kg ATI-101, IV + Etanercept 1 mg/kg |
| 10 | 10 | Arthritis + .25 mg/kg MTX, PO, saline IV, Etanercept 1 mg/kg |

TABLE 4

| Treatment groups | | Arthritis + Prophylactic |
|---|---|---|
| Group | N | IV, ATI-101 (5 ml/kg) or Oral MTX (10 ml/kg), 2X/week Day 0-21 |
| 11 | 10 | Arthritis + 250 mg/kg ATI-101 IV |
| 12 | 10 | Arthritis + 1 mg/kg MTX PO, saline IV |
| 13 | 10 | Arthritis + 0.75 mg/kg MTX PO, saline IV |
| 14 | 10 | Arthritis + 0.25 mg/kg MTX PO, saline IV |

Animals were anesthetized and immunized at the base of the tail and two sites on the back on day 0 and day 6. Animals were weighed on days 0, 3, 9-24. Animals were treated 2 times weekly (2×/week) on Monday, and Thursday (dose days 0, 3, 7, 10, 14, 17, 21) either intravenously with vehicle (saline) or ATI-101 (5, 20, 65 or 250 mg/kg) or orally (PO) with Methotrexate (MTX) (0.25, 75 or 1 mg/kg). Treatment was administered either alone or in combination with etanercept, (1 mg/kg) dosed subcutaneously on days 9, 12 and 15. Animals were euthanized on study day 24 beyond the usual 17 days in order to evaluate the toxicity of MTX and ATI-101 for establishment of a therapeutic index." Efficacy evaluation was based on ankle caliper measurements at day 17. Six of 10 rats from the 250 mg/kg ATI-101 group were found dead on or before study day 16. The remaining 4 animals were sacrificed for necropsy on day 16. All other animals survived to study termination. Dosing at 250 mg/ml was expected to be toxic; it was included to determine the therapeutic index for ATI-101.

Dose Response

Figure 9:
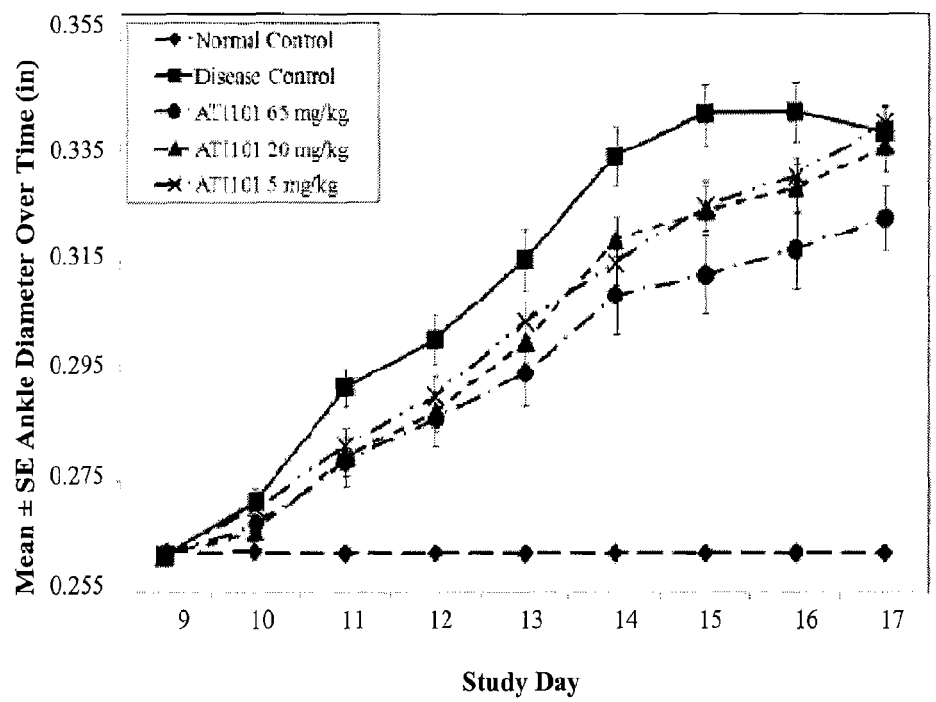
FIG. 9 depicts the dose response over the ATI-101 range from 5 mg/kg through 65 mg/kg.

As shown in FIG. 9, the ankle diameters showed a dose response relationship over the ATI-101 range from 5 mg/kg through 65 mg/kg twice weekly IV dosing with a minimally effective dose shown at 5 mg/kg. Ankle diameter AUC (days 0-17) was significantly decreased toward normal for rats treated with 65 mg/kg ATI-101 (35%), 20 mg/kg ATI-101 (23%), 5 mg/kg ATI-101 (20%) reflecting the dose response shown described for FIG. 9.

Combination of ATI-101 and Entanercept

ATI-101 doses (5, 20 and 65 mg/kg) all showed an additive increase in the ankle diameter efficacy parameter at the 17 day time point when combined with etanercept administration. Significant decreases in ankle diameter (from disease control) were seen for ATI-101 doses (5, 20 and 65 mg/kg) alone or in combination with and for 0.25 mg/kg MTX alone or in combination with etanercept. The results are summarized in Table 5.

TABLE 5

| | Treatment Drug alone | | Treatment Drug in combination with etanercept | |
|---|---|---|---|---|
| drug | | % decrease in ankle diameter verses disease control | | % decrease in ankle diameter verses disease control |
| etanercept 1 mg/kg | | 37 | — | |
| 65 mg/kg ATI-101 | | 35 | 65 mg/kg ATI-101 + etanercept | 62 |
| 20 mg/kg ATI-101 | | 23 | 20 mg/kg ATI-101 + etanercept | 56 |
| 5 mg/kg ATI-101 | | 20 | 5 mg/kg ATI-101 + etanercept | 51 |
| 0.25 mg/kg MTX | | 52 | 0.25 mg/kg MTX + etanercept | 76 |

Figure 10:
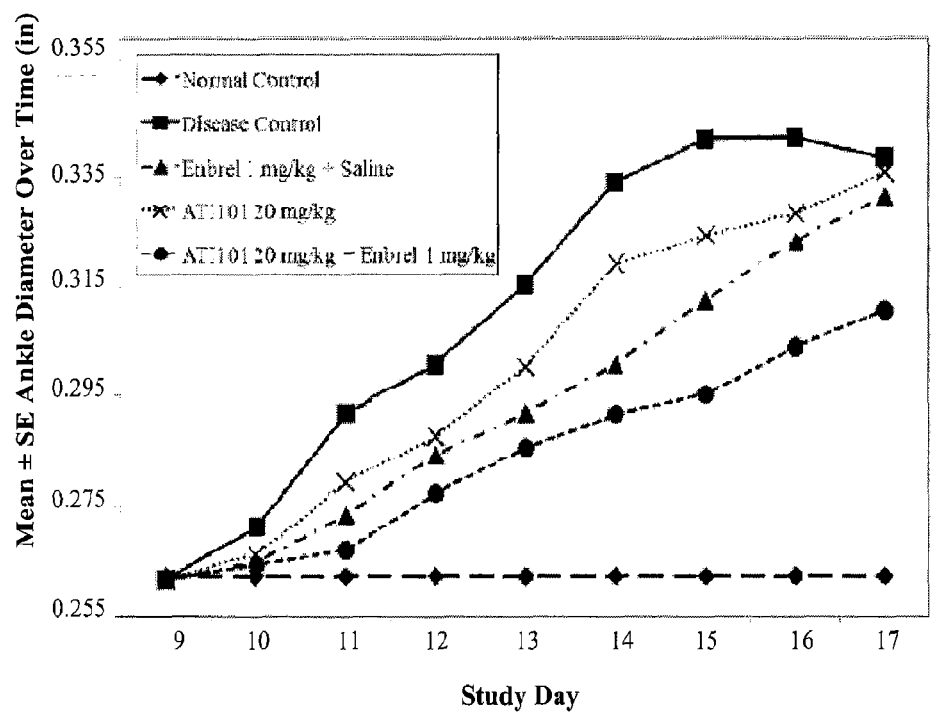
FIG. 10 depicts the decrease in ankle diameter when ATI-101, (20 mg/kg) is administered alone or in combination with etanercept.

FIG. 10 shows in a graphic form, the decrease in ankle diameter when ATI-101, (20mg/kg) was administered alone or in combination with etanercept. The combination showed an additive anti-arthritic effect over the usual 17 day study period compared with either treatment alone.

Example 6

This example shows the dose-dependent increase in binding/uptake of G5-FITC-FA (as measured by mean F11) as compared to G5-FITC very low binding/uptake, which thereby demonstrates the specificity of folate as mediating the binding/uptake of G5-FITC-FA.

Primary peritoneal macrophage isolation. Rats and mice were injected i.p. with Brewer's Thioglycollate Medium (BTM), 4.05 g in 100 ml ddH$_2$O. Rats were injected with ~5-7 ml; mice were injected with ~1-3 ml. After three days, rats and mice were euthanized and their peritoneal cavities were lavaged with 5% FBS in HBSS. The lavages were collected and centrifuged at 2000 rpm for 10 min. Pellets were resuspended in 1 ml of 10% HBSS in ddH$_2$O and vortexed for 15 min to lyse red blood cells. 10 ml HBSS was then added to return isotonicity and cells were centrifuged again at 2000 rpm for 10 min. The cycle of resuspending in 10% HBSS, vortexing, adding excess HBSS, and centrifuging was repeated until no red blood cells were visually observable. Cells were then seeded in macrophage adhesion media (MAM) in plates and dishes that were pre-incubated with MAM for about two hours. Four hours after seeding, MAM was aspirated and RPMI1640 was added and used as the culture media.

Cell culture. Binding studies were performed on KB, Raw264.7, NR8383, and primary rat & mice peritoneal macrophages. For folate-rich supplementation, KB, Raw264.7, and primary cells were grown in RPMI1640 and NR8383 cells were grown in F12K. For folate-deficient supplementation, all cells were grown in RPMI1640 without folate. In all cases, all media was supplemented with 10% fetal bovine serum and 1% penicillin-streptomycin.

In vitro binding/uptake assays. To activate macrophages and induce folate receptor overexpression, cells were grown in folate-deficient media for at least three days, seeded in E-well or 24-well plates, and incubated with 1 μg/ml LPS overnight. Binding and uptake of G3 and G5 conjugates (with FITC) was assessed by incubating cells with conjugates for two hours. To assess competition between conjugates and free folate, free folate was incubated with cells one-half hour before adding conjugates. After incubation, cells were scraped off (except KB cells, which were trypsinized to remove cells from the plates), washed twice with ice-cold PBS, and resuspended in 0.1 wt % BSA in PBS. Mean fluorescence was measured by flow cytometry.

Figure 11:
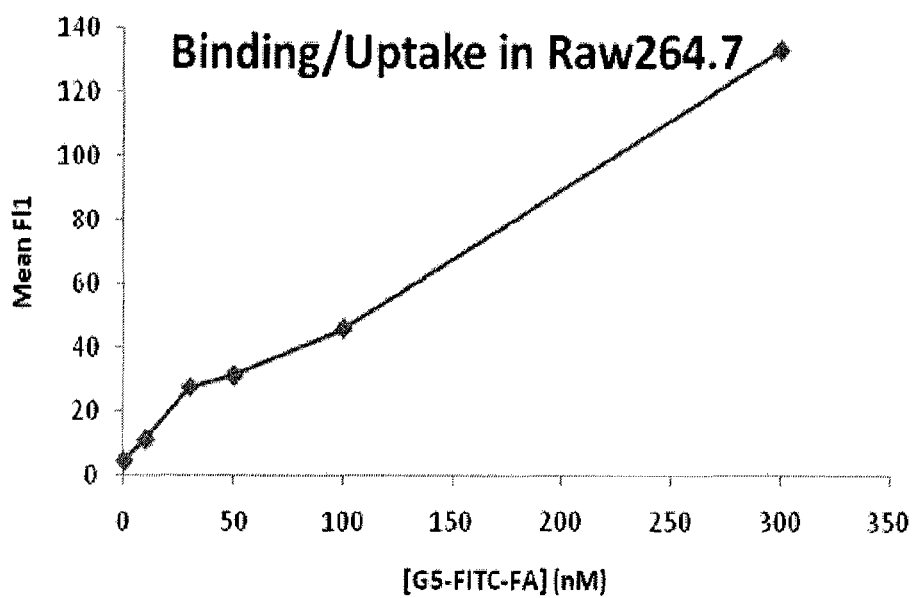
FIG. 11 shows binding/uptake of G5-FITC-FA in Raw264.7 cells.
Figure 12:
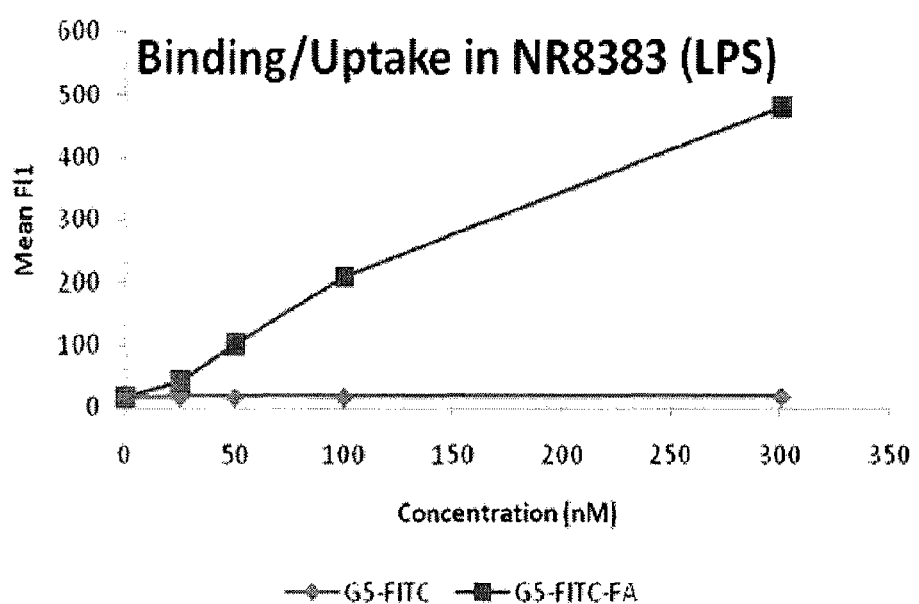
FIG. 12 shows binding/uptake of G5-FITC and G5-FITC-FA in NR8383 (LPS) cells.
Figure 13:
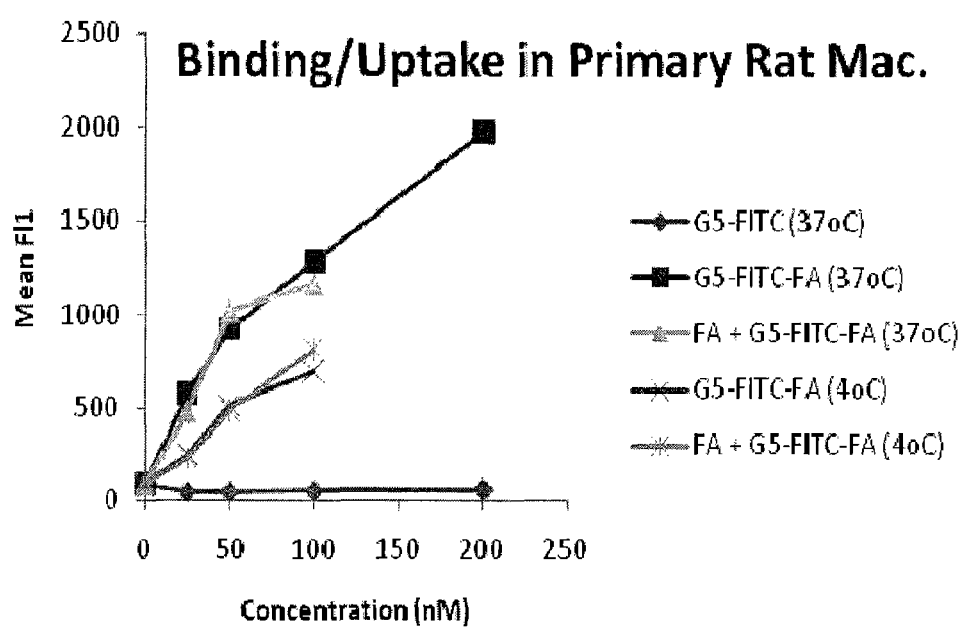
FIG. 13 shows binding uptake of G5-FITC at 37 degrees Celsius, G5-FITC-FA at 37 degrees Celsius, FA+G5-FITC-FA at 37 degrees Celsius, G5-FITC-FA at 40 degrees Celsius, and FA+G5-FITC-FA at 40 degrees Celsius in primary rat macrophages.
Figure 14:
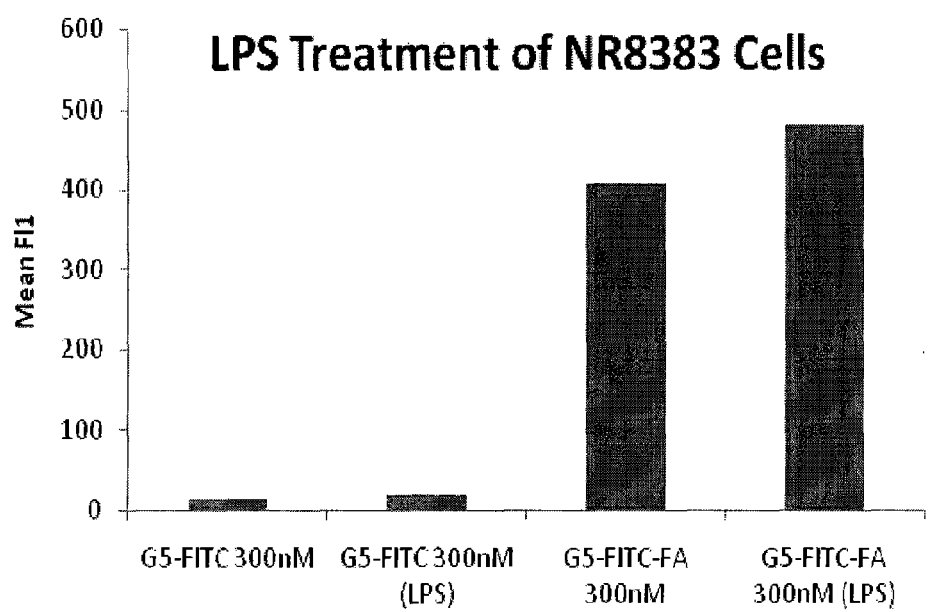
FIG. 14 shows mean fluorescence of G5-FITC 300 nM with and without LPS treatment, and G5-FITC-FA 300 nM with and without LPS treatment.
Figure 15:
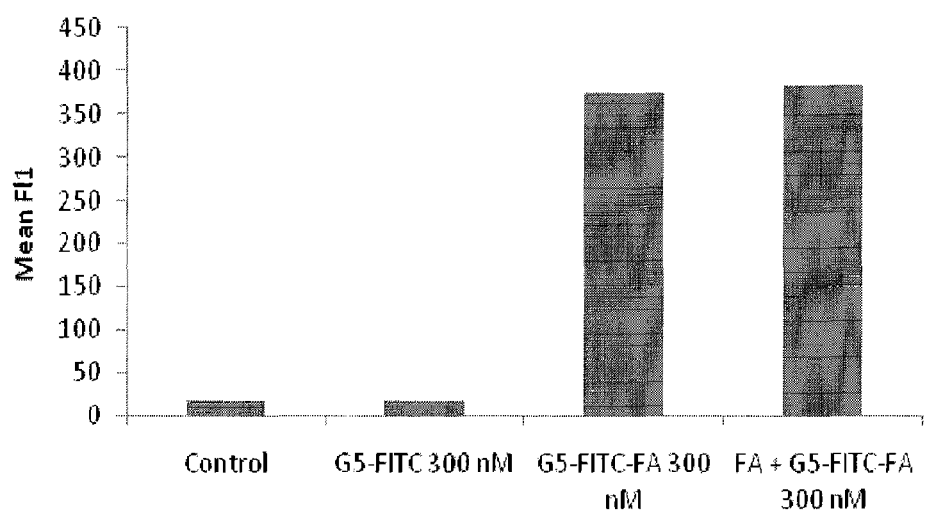
FIG. 15 shows mean fluorescence of control, G5-FITC 300 nM, G5-FITC-FA 300 nM in NR8383 (LPS) cells deficient for folic acid (cells have approximately 10 nanomolar folic acid) compared to the mean fluorescence of G5-FITC-FA 300 nM in NR8383 (LPS) cells with folate media (cells have approximately 20 micromolar folic acid) (indicated as +FM in figure).

FIG. 11 shows binding/uptake of G5-FITC-FA in Raw264.7 cells. FIG. 12 shows binding/uptake of G5-FITC and G5-FITC-FA in NR8383 (LPS) cells. FIG. 13 shows binding uptake of G5-FITC at 37 degrees Celsius, G5-FITC-FA at 37 degrees Celsius, FA+G5-FITC-FA at 37 degrees Celsius, G5-FITC-FA at 40 degrees Celsius, and FA+G5-FITC-FA at 40 degrees Celsius in primary rat macrophages. FIG. 14 shows mean fluorescence of G5-FITC 300 nM with and without LPS treatment, and G5-FITC-FA 300 nM with and without LPS treatment. FIG. 15 shows mean fluorescence of control, G5-FITC 300 nM, G5-FITC-FA 300 nM in NR8383 (LPS) cells deficient for folic acid (cells have approximately 10 nanomolar folic acid) compared to the mean fluorescence of G5-FITC-FA 300 nM in NR8383 (LPS) cells with folate media (cells have approximately 20 micromolar folic acid) (indicated as +FM in figure).

Example 7

Lewis female rats were induced with RA by Freund's complete adjuvant (onset of RA around day 12). Drugs were given three times per week, starting on the same day as induction of RA. Every other day, the degree of arthritis in rats was measured by assigning a clinical score (0-4), and measure the paw volume by caliper and plethysmography.

Figure 16:
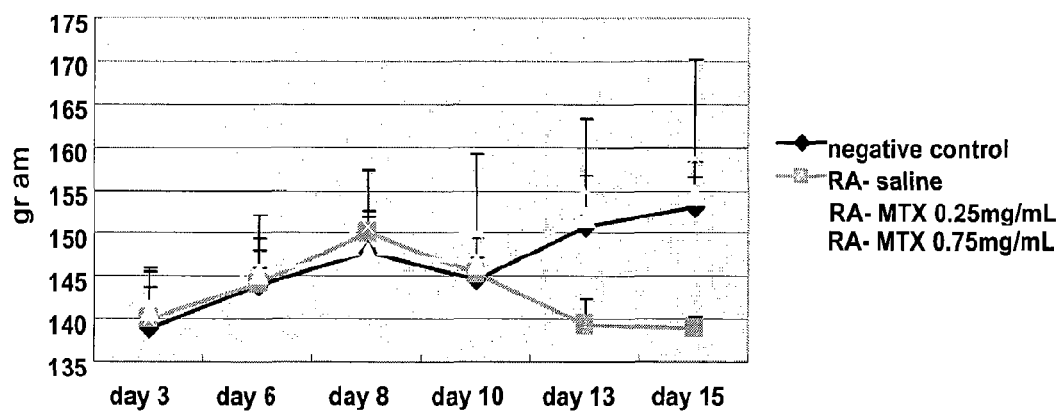
FIG. 16 shows rat body weight changes for rheumatoid arthritis rats treated with saline, rheumatoid arthritis rats treated with methotrexate 0.25 mg/ml, rheumatoid arthritis rats treated with methotrexate 0.75 mg/ml, and a negative control (no induced rheumatoid arthritis).
Figure 18:
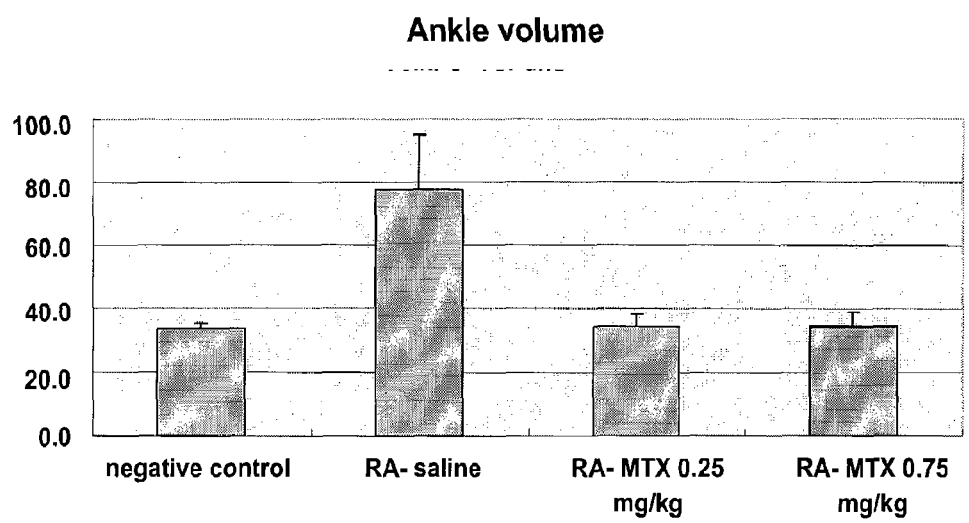
FIG. 18 shows ankle volume for rheumatoid arthritis rats treated with saline, rheumatoid arthritis rats treated with methotrexate 0.25 mg/ml, rheumatoid arthritis rats treated with methotrexate 0.75 mg/ml, and a negative control (no induced rheumatoid arthritis).
Figure 19:
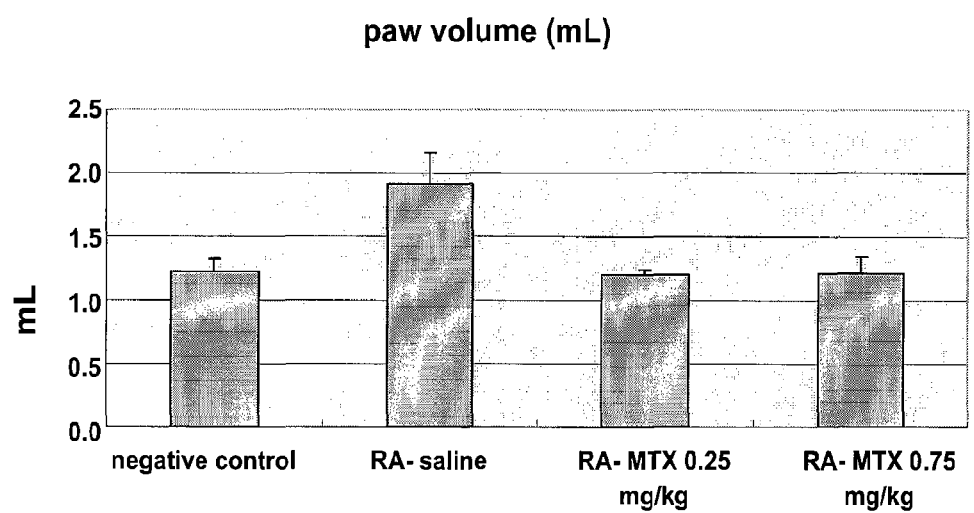
FIG. 19 shows paw volume by plethysmography for rheumatoid arthritis rats treated with saline, rheumatoid arthritis rats treated with methotrexate 0.25 mg/ml, rheumatoid arthritis rats treated with methotrexate 0.75 mg/ml, and a negative control (no induced rheumatoid arthritis).
Figure 20:
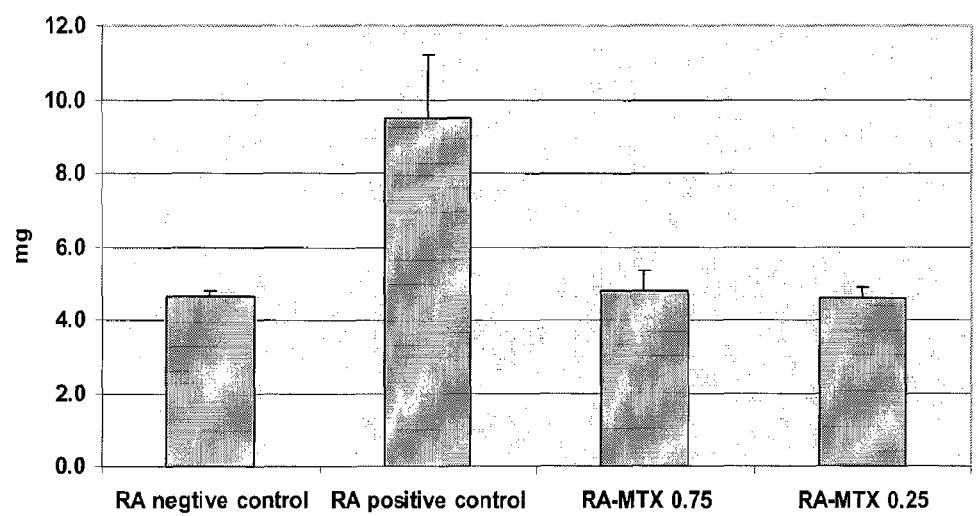
FIG. 20 shows relative ankle joints weight (mg/g BW (body weight)) for rheumatoid arthritis rats treated with saline, rheumatoid arthritis rats treated with methotrexate 0.25 mg/ml, rheumatoid arthritis rats treated with methotrexate 0.75 mg/ml, and a negative control (no induced rheumatoid arthritis).
Figure 21:
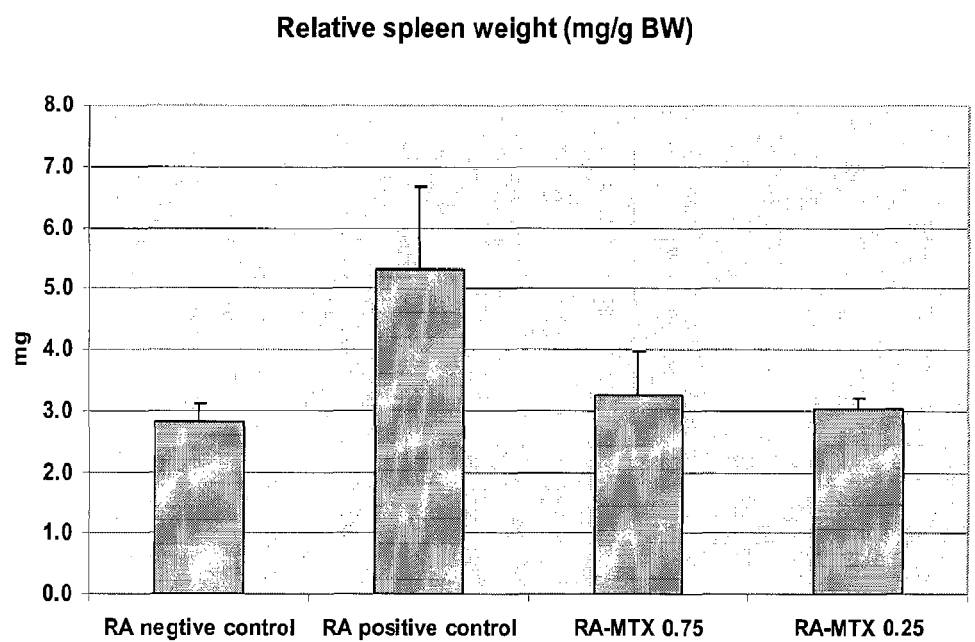
FIG. 21 shows relative speen weight (mg/g BW (body weight)) for rheumatoid arthritis rats treated with saline, rheumatoid arthritis rats treated with methotrexate 0.25 mg/ml, rheumatoid arthritis rats treated with methotrexate 0.75 mg/ml, and a negative control (no induced rheumatoid arthritis).
Figure 22:
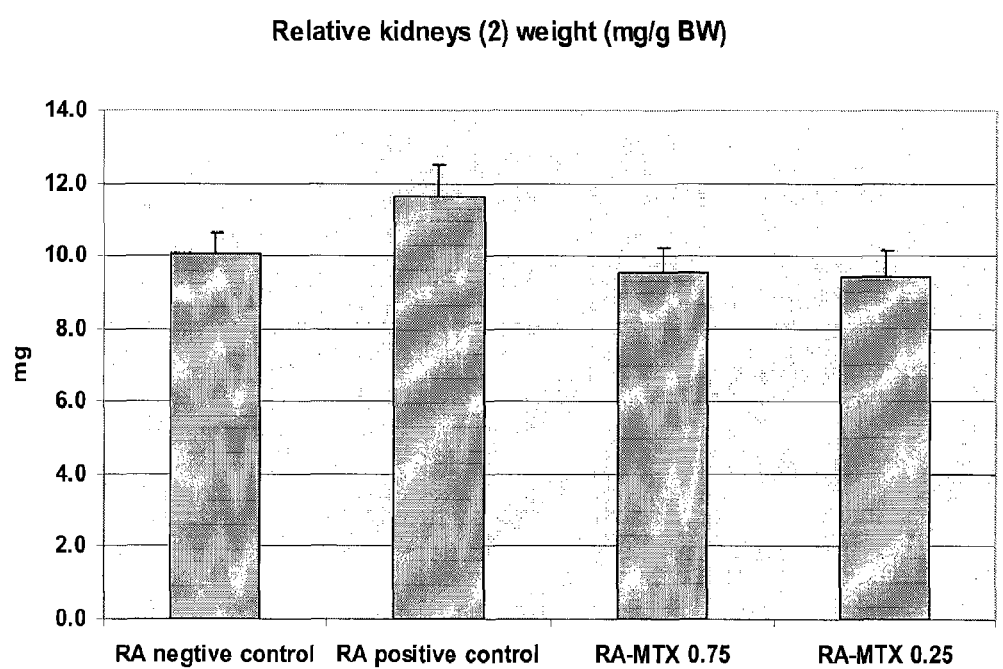
FIG. 22 shows relative kidney weight (two kidneys) (mg/g BW (body weight)) for rheumatoid arthritis rats treated with saline, rheumatoid arthritis rats treated with methotrexate 0.25 mg/ml, rheumatoid arthritis rats treated with methotrexate 0.75 mg/ml, and a negative control (no induced rheumatoid arthritis).
Figure 23:
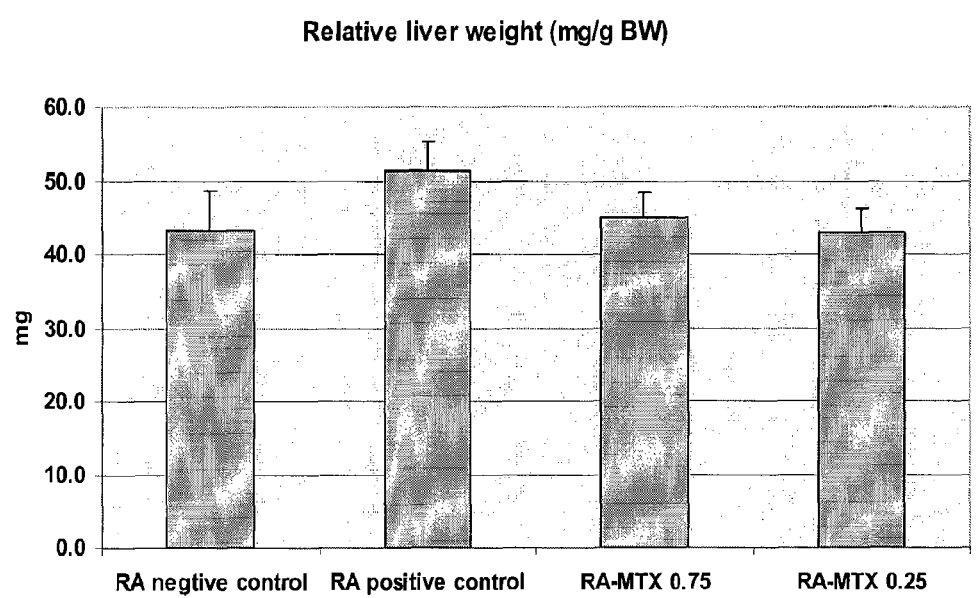
FIG. 23 shows relative liver weight (mg/g BW (body weight)) for rheumatoid arthritis rats treated with saline, rheumatoid arthritis rats treated with methotrexate 0.25 mg/ml, rheumatoid arthritis rats treated with methotrexate 0.75 mg/ml, and a negative control (no induced rheumatoid arthritis).

1$^{st}$ Experiment. 20 rats were divided into four groups. One group of three rats formed the negative control—rats injected with saline and not induced with RA. RA was induced in all other rats. Another group of five rats formed the positive control—arthritic rats treated with saline. The remaining rats were treated with methotrexate (MTX), six at a low dose (0.25 mg/kg), and the other six at a high dose (0.75 mg/kg). FIG. 16 shows rat body weight changes for rheumatoid arthritis rats treated with saline, rheumatoid arthritis rats treated with methotrexate 0.25 mg/ml, rheumatoid arthritis rats treated with methotrexate 0.75 mg/ml, and a negative control (no induced rheumatoid arthritis). FIG. 17 shows blinded arthritis score (e.g., where a score of "0-1" indicates normal, "1-2" indicates mild arthritis; "2-3" indicates moderate arthritis; and "3-4" indicates severe arthritis) for each rat where G2 are the rheumatoid arthritis rats treated with saline, G3 are the rheumatoid arthritis rats treated with methotrexate 0.25 mg/ml, G4 are the rheumatoid arthritis rats treated with methotrexate 0.75 mg/ml, and G1 is the negative control rats (no induced rheumatoid arthritis). FIG. 18 shows ankle volume for rheumatoid arthritis rats treated with saline, rheumatoid arthritis rats treated with methotrexate 0.25 mg/ml, rheumatoid arthritis rats treated with methotrexate 0.75 mg/ml, and a negative control (no induced rheumatoid arthritis). FIG. 19 shows paw volume by plethysmography for rheumatoid arthritis rats treated with saline, rheumatoid arthritis rats treated with methotrexate 0.25 mg/ml, rheumatoid arthritis rats treated with methotrexate 0.75 mg/ml, and a negative control (no induced rheumatoid arthritis). FIG. 20 shows relative ankle joints weight (mg/g BW (body weight)) for rheumatoid arthritis rats treated with saline, rheumatoid arthritis rats treated with methotrexate 0.25 mg/ml, rheumatoid arthritis rats treated with methotrexate 0.75 mg/ml, and a negative control (no induced rheumatoid arthritis). FIG. 21 shows relative speen weight (mg/g BW (body weight)) for rheumatoid arthritis rats treated with saline, rheumatoid arthritis rats treated with methotrexate 0.25 mg/ml, rheumatoid arthritis rats treated with methotrexate 0.75 mg/ml, and a negative control (no induced rheumatoid arthritis). FIG. 22 shows relative kidney weight (two kidneys) (mg/g BW (body weight)) for rheumatoid arthritis rats treated with saline, rheumatoid arthritis rats treated with methotrexate 0.25 mg/ml, rheumatoid arthritis rats treated with methotrexate 0.75 mg/ml, and a negative control (no induced rheumatoid arthritis). FIG. 23 shows relative liver weight (mg/g BW (body weight)) for rheumatoid arthritis rats treated with saline, rheumatoid arthritis rats treated with methotrexate 0.25 mg/ml, rheumatoid arthritis rats treated with methotrexate 0.75 mg/ml, and a negative control (no induced rheumatoid arthritis).

Figure 25:
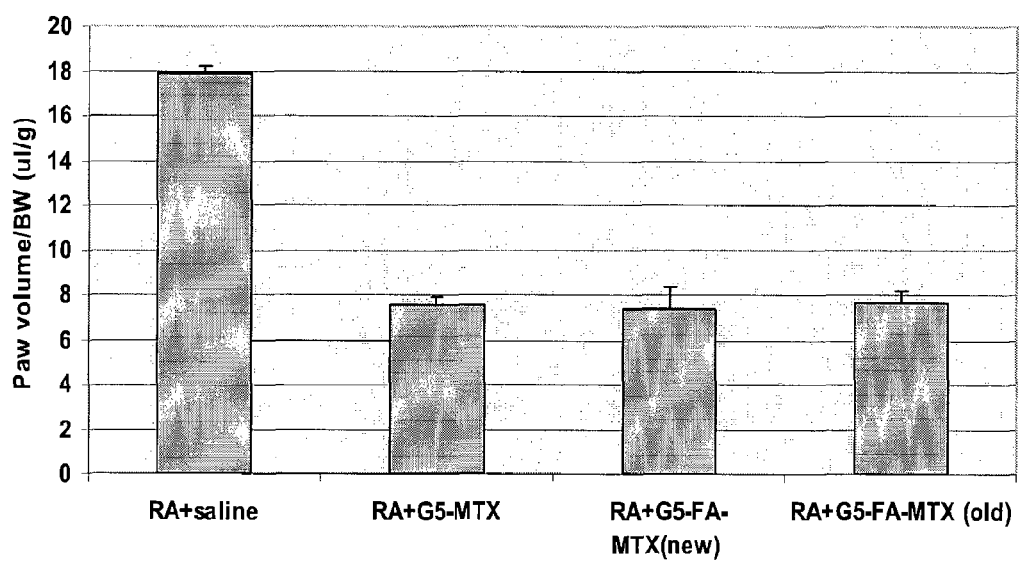
FIG. 25 shows relative paw volume by plethysmography for rheumatoid arthritis rats treated with saline, rheumatoid arthritis rats treated with G5-Ac-gly-MTX, rheumatoid arthritis rats treated with G5-Ac-FA-gly-MTX ("new batch"; less old than the "old batch"), rheumatoid arthritis rats treated with G5-Ac-FA-gly-MTX ("old batch"; older than the "new batch") and a negative control (no induced rheumatoid arthritis).
Figure 26:
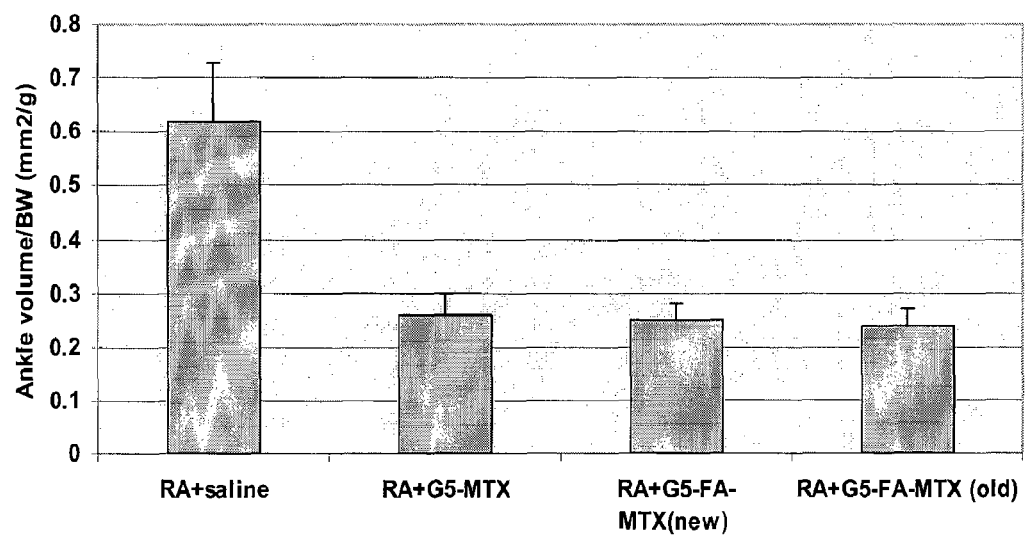
FIG. 26 shows relative ankle volume by caliper for rheumatoid arthritis rats treated with saline, rheumatoid arthritis rats treated with G5-Ac-gly-MTX, rheumatoid arthritis rats treated with G5-Ac-FA-gly-MTX ("new batch"; less old than the "old batch"), rheumatoid arthritis rats treated with G5-Ac-FA-gly-MTX ("old batch"; older than the "new batch") and a negative control (no induced rheumatoid arthritis).
Figure 27:
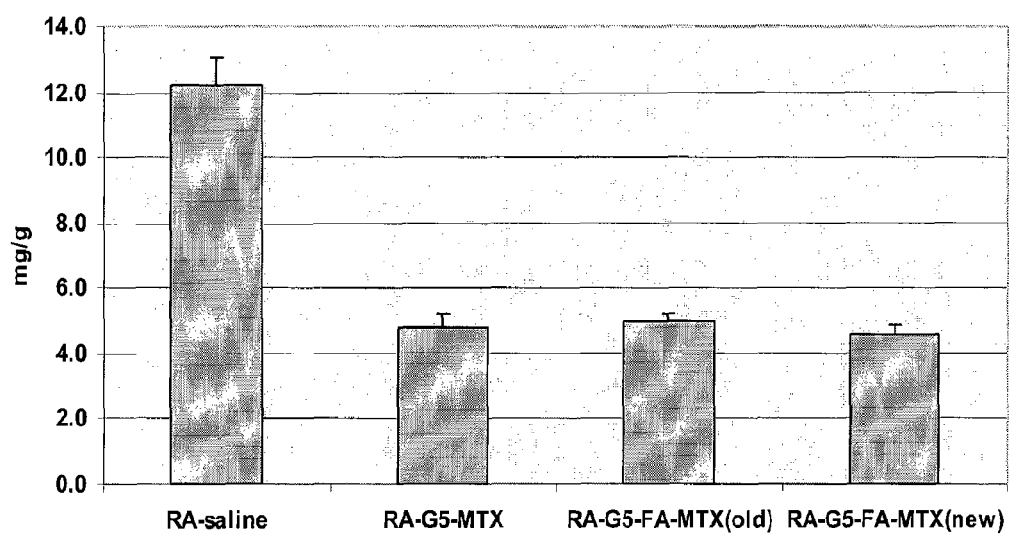
FIG. 27 shows relative ankle weight for rheumatoid arthritis rats treated with saline, rheumatoid arthritis rats treated with G5-Ac-gly-MTX, rheumatoid arthritis rats treated with G5-Ac-FA-gly-MTX ("new batch"; less old than the "old batch"), rheumatoid arthritis rats treated with G5-Ac-FA-gly-MTX ("old batch"; older than the "new batch") and a negative control (no induced rheumatoid arthritis).
Figure 28:
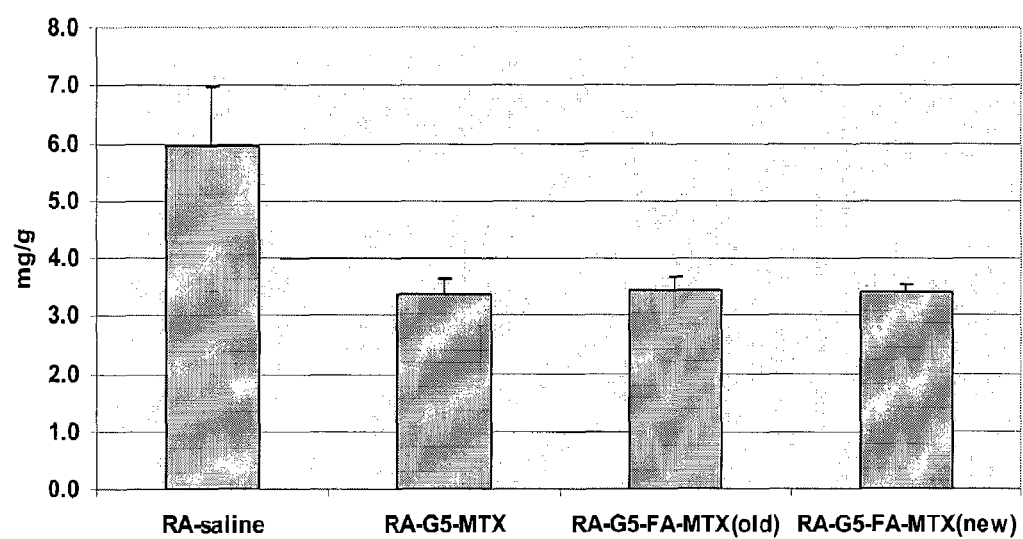
FIG. 28 shows relative spleen weight for rheumatoid arthritis rats treated with saline, rheumatoid arthritis rats treated with G5-Ac-gly-MTX, rheumatoid arthritis rats treated with G5-Ac-FA-gly-MTX ("new batch"; less old than the "old batch"), rheumatoid arthritis rats treated with G5-Ac-FA-gly-MTX ("old batch"; older than the "new batch") and a negative control (no induced rheumatoid arthritis).
Figure 29:
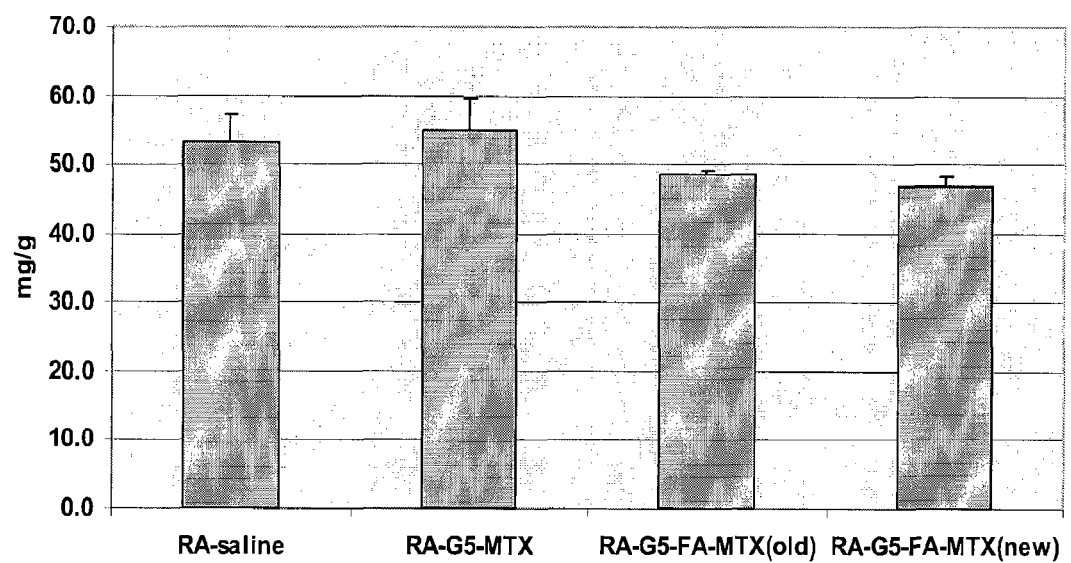
FIG. 29 shows relative liver weight for rheumatoid arthritis rats treated with saline, rheumatoid arthritis rats treated with G5-Ac-gly-MTX, rheumatoid arthritis rats treated with G5-Ac-FA-gly-MTX ("new batch"; less old than the "old batch"), rheumatoid arthritis rats treated with G5-Ac-FA-gly-MTX ("old batch"; older than the "new batch") and a negative control (no induced rheumatoid arthritis).
Figure 30:
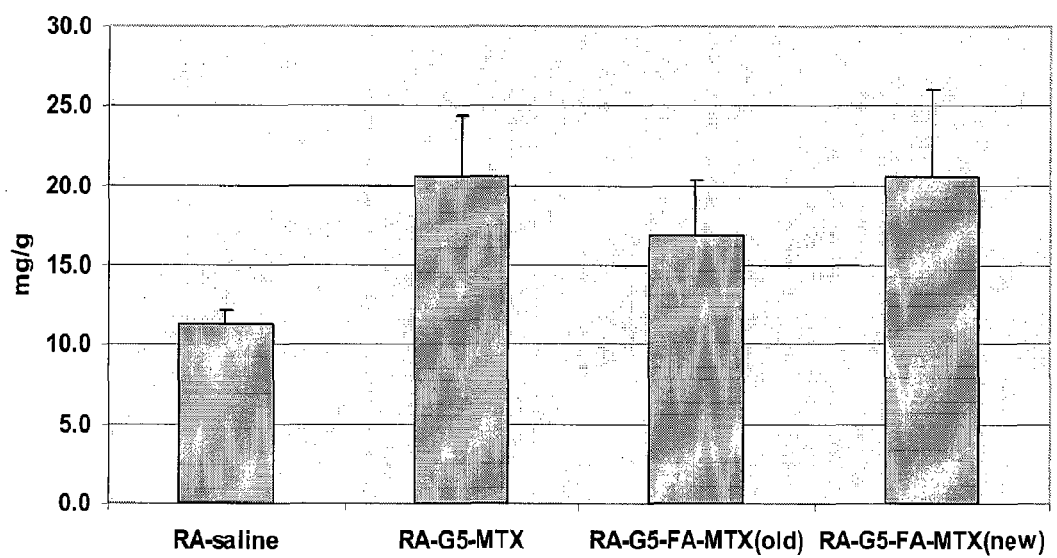
FIG. 30 shows relative kidney weight (two kidneys) for rheumatoid arthritis rats treated with saline, rheumatoid arthritis rats treated with G5-Ac-gly-MTX, rheumatoid arthritis rats treated with G5-Ac-FA-gly-MTX ("new batch"; less old than the "old batch"), rheumatoid arthritis rats treated with G5-Ac-FA-gly-MTX ("old batch"; older than the "new batch") and a negative control (no induced rheumatoid arthritis).

$2^{nd}$ Experiment. 12 rats were divided into four groups of three. One group was a positive control (arthritic rats treated with saline). The other three groups (all arthritic rats) were treated with three corresponding conjugates, RA-G5-Ac-gly-MTX, RA-G5-Ac-FA-gly-MTX (new batch; less old than the "old batch"), and RA-G5-Ac-FA-gly-MTX ("old batch"; older than the "new batch"). The dosage was for all compounds were 100 mg/kg. At the end of both experiments, animals were sacrificed and there organs and ankle joints were removed and weighed. FIG. 24 shows blinded arthritis score (e.g., where a score of "0-1" indicates normal, "1-2" indicates mild arthritis; "2-3" indicates moderate arthritis; and "3-4" indicates severe arthritis) for rheumatoid arthritis rats treated with saline, rheumatoid arthritis rats treated with G5-Ac-gly-MTX (indicated in figure as "RA-G5-MTX"), rheumatoid arthritis rats treated with G5-Ac-FA-gly-MTX (new) (indicated in figure as "RA-G5-FA-MTX (new)"), rheumatoid arthritis rats treated with G5-Ac-FA-gly-MTX (old) (indicated in figure as "RA-G5-FA-MTX (old)"), and a negative control (no induced rheumatoid arthritis). FIG. 25 shows relative paw volume by plethysmography for rheumatoid arthritis rats treated with saline, rheumatoid arthritis rats treated with G5-Ac-gly-MTX (indicated in figure as ", rheumatoid arthritis rats treated with G5-Ac-FA-gly-MTX (new) (indicated in figure as "RA-G5-FA-MTX (new)"), rheumatoid arthritis rats treated with G5-Ac-FA-gly-MTX (old) (indicated in figure as "RA-G5-FA-MTX (old)"), and a negative control (no induced rheumatoid arthritis). FIG. 26 shows relative ankle volume by caliper for rheumatoid arthritis rats treated with saline, rheumatoid arthritis rats treated with G5-Ac-gly-MTX, rheumatoid arthritis rats treated with G5-Ac-FA-gly-MTX (new) (indicated in figure as "RA-G5-FA-MTX (new)"), rheumatoid arthritis rats treated with G5-Ac-FA-gly-MTX (old) (indicated in figure as "RA-G5-FA-MTX (old)"), and a negative control (no induced rheumatoid arthritis). FIG. 27 shows relative ankle weight for rheumatoid arthritis rats treated with saline, rheumatoid arthritis rats treated with G5-Ac-gly-MTX, rheumatoid arthritis rats treated with G5-Ac-FA-gly-MTX (new) (indicated in figure as "RA-G5-FA-MTX (new)"), rheumatoid arthritis rats treated with G5-Ac-FA-gly-MTX (old) (indicated in figure as "RA-G5-FA-MTX (old)"), and a negative control (no induced rheumatoid arthritis). FIG. 28 shows relative spleen weight for rheumatoid arthritis rats treated with saline, rheumatoid arthritis rats treated with G5-Ac-gly-MTX, rheumatoid arthritis rats treated with G5-Ac-FA-gly-MTX (new) (indicated in figure as "RA-G5-FA-MTX (new)"), rheumatoid arthritis rats treated with G5-Ac-FA-gly-MTX (old) (indicated in figure as "RA-G5-FA-MTX (old)"), and a negative control (no induced rheumatoid arthritis). FIG. 29 shows relative liver weight for rheumatoid arthritis rats treated with saline, rheumatoid arthritis rats treated with G5-Ac-gly-MTX, rheumatoid arthritis rats treated with G5-Ac-FA-gly-MTX (new) (indicated in figure as "RA-G5-FA-MTX (new)"), rheumatoid arthritis rats treated with G5-Ac-FA-gly-MTX (old) (indicated in figure as "RA-G5-FA-MTX (old)"), and a negative control (no induced rheumatoid arthritis). FIG. 30 shows relative kidney weight (two kidneys) for rheumatoid arthritis rats treated with saline, rheumatoid arthritis rats treated with G5-Ac-gly-MTX, rheumatoid arthritis rats treated with G5-Ac-FA-gly-MTX (new) (indicated in figure as "RA-G5-FA-MTX (new)"), rheumatoid arthritis rats treated with G5-Ac-FA-gly-MTX (old) (indicated in figure as "RA-G5-FA-MTX (old)"), and a negative control (no induced rheumatoid arthritis).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in molecular biology, in vitro fertilization, development, or related fields are intended to be within the scope of the following claims.

We claim:

1. A method for treating a subject having an autoimmune disorder and/or an inflammatory disorder comprising administering to said subject an effective amount of one or more dendrimers conjugated with one or more functional groups selected from the group consisting of a therapeutic agent, a targeting agent, a trigger agent, and an imaging agent, wherein said one or more dendrimers conjugated with one or more functional groups is represented by formula 1:

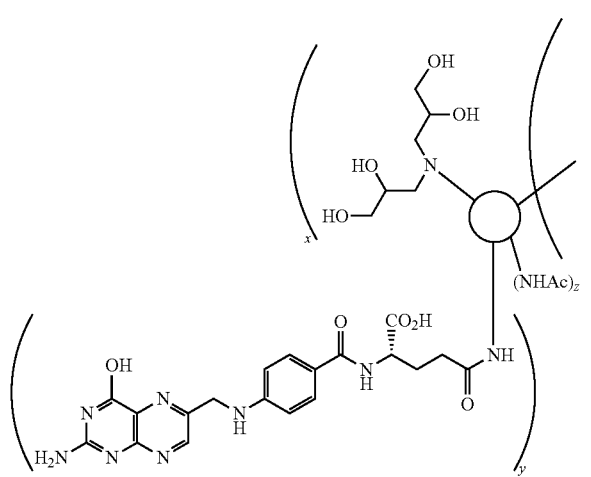

Formula I

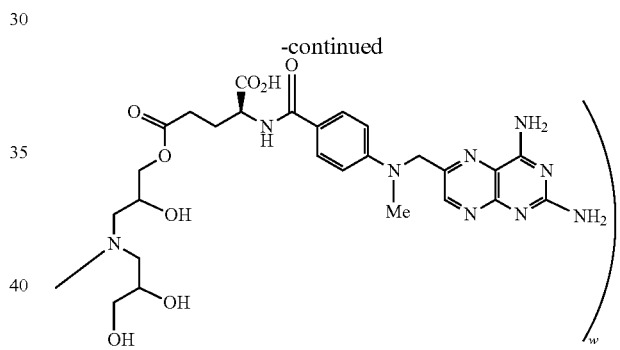

wherein

○ represents a G5 PAMAM dendrimer;
   w is one or more methotrextates;
   x is one or more glycidols;
   y is one or more folates; and
   z is one or more acetyls,
wherein said one or more methotrexates is 10 methotrexates, and said one or more folates is 3 folates.

2. A composition comprising a dendrimer conjugated with one or more functional ligands as represented by formula 1:

Formula I
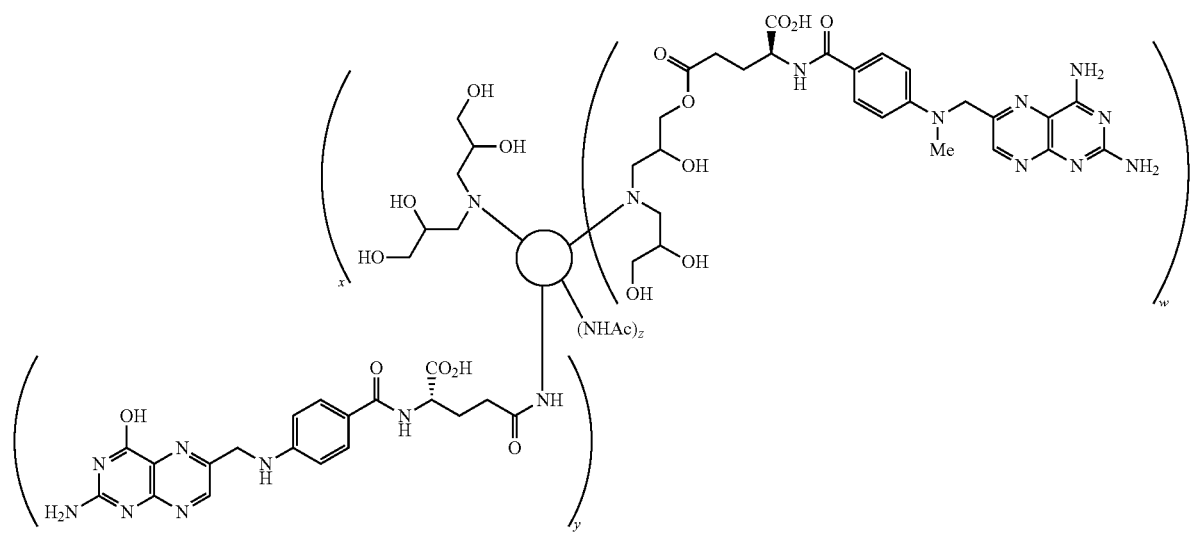
wherein
 represents a G5 PAMAM dendrimer;
w is one or more methotrextates;
x is one or more glycidols;
y is one or more folates; and
z is one or more acetyls,
wherein said one or more methotrexates is 10 methotrexates, and said one or more folates is 3 folates.
* * * * *